United States Patent
Sugihara et al.

(10) Patent No.: US 12,164,229 B2
(45) Date of Patent: Dec. 10, 2024

(54) RESIST COMPOSITION AND METHOD FOR PRODUCING RESIST PATTERN

(71) Applicant: SUMITOMO CHEMICAL COMPANY, LIMITED, Tokyo (JP)

(72) Inventors: Masako Sugihara, Osaka (JP); Mutsuko Higo, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 858 days.

(21) Appl. No.: 16/724,455

(22) Filed: Dec. 23, 2019

(65) Prior Publication Data

US 2020/0209749 A1     Jul. 2, 2020

(30) Foreign Application Priority Data

Dec. 27, 2018 (JP) ................................. 2018-244482

(51) Int. Cl.
    *G03F 7/039*     (2006.01)
    *C07C 49/175*     (2006.01)
    (Continued)

(52) U.S. Cl.
    CPC .......... *G03F 7/0392* (2013.01); *C07C 49/175* (2013.01); *C08L 25/18* (2013.01);
    (Continued)

(58) Field of Classification Search
    CPC . G03F 7/0392; G03F 7/11; G03F 7/45; G03F 7/2004; G03F 7/2053; G03F 7/32;
    (Continued)

(56) References Cited

U.S. PATENT DOCUMENTS 5,326,675 A * 7/1994 Niki .......................... G03F 7/11
                                                                       430/326
2004/0013974 A1    1/2004 Dietliker et al.
(Continued)

FOREIGN PATENT DOCUMENTS

| CN | 1228851 A | 9/1999 |
|---|---|---|
| CN | 1690856 A | 11/2005 |

(Continued)

OTHER PUBLICATIONS

Office Action dated Apr. 14, 2023, by the Taiwanese Patent Office in corresponding Taiwanese Patent Application No. 108147481 with an English translation of the Office Action (13 pages).

(Continued)

*Primary Examiner* — Shane Fang
(74) *Attorney, Agent, or Firm* — Panitch Schwarze Belisario & Nadel LLP

(57) ABSTRACT

A resist composition includes a novolak resin in which a hydroxy group is substituted with a group represented by formula (3), an acid generator, a quencher, and a solvent:

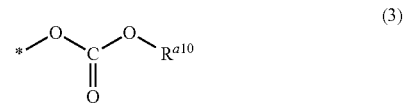

wherein, in formula (3), $R^{a10}$ represents a hydrocarbon group having 1 to 20 carbon atoms (e.g., a chain hydrocarbon group such as an alkyl group, an alkenyl group and an alkynyl group, an alicyclic hydrocarbon group, an aromatic hydrocarbon group, groups formed by combining these groups, etc.) and * represents a bond.

15 Claims, 1 Drawing Sheet

(51) Int. Cl.
*C08L 25/18* (2006.01)
*C08L 61/14* (2006.01)
*G03F 7/004* (2006.01)
*G03F 7/20* (2006.01)
*G03F 7/32* (2006.01)

(52) U.S. Cl.
CPC ............ *C08L 61/14* (2013.01); *G03F 7/0045* (2013.01); *G03F 7/2004* (2013.01); *G03F 7/2053* (2013.01); *G03F 7/32* (2013.01)

(58) Field of Classification Search
CPC ....... G03F 7/094; G03F 7/168; C07C 49/175; C08L 25/18; C08L 61/14; C08G 61/08; C08G 2261/228; C08G 2261/3325; C08G 2261/418; C09D 165/00
See application file for complete search history.

(56) References Cited

U.S. PATENT DOCUMENTS

| | | |
|---|---|---|
| 2008/0153036 A1* | 6/2008 | Suetsugu ............... G03F 7/0392 430/287.1 |
| 2011/0123929 A1 | 5/2011 | Fujita et al. |
| 2015/0086927 A1* | 3/2015 | Sugihara ............... G03F 7/0388 430/287.1 |
| 2016/0017083 A1 | 1/2016 | Imada et al. |
| 2016/0097974 A1 | 4/2016 | Asai et al. |
| 2016/0291464 A1 | 10/2016 | Kawamura et al. |
| 2016/0291465 A1 | 10/2016 | Sugihara et al. |
| 2016/0291466 A1 | 10/2016 | Sugihara et al. |
| 2016/0291467 A1 | 10/2016 | Sugihara et al. |
| 2017/0145142 A1 | 5/2017 | Toida et al. |
| 2017/0277036 A1* | 9/2017 | Toriumi ..................... G03F 7/09 |
| 2018/0134834 A1 | 5/2018 | Imada et al. |
| 2018/0327533 A1 | 11/2018 | Imada et al. |
| 2019/0056657 A1 | 2/2019 | Toida et al. |

FOREIGN PATENT DOCUMENTS

| | | |
|---|---|---|
| CN | 105190439 A | 12/2015 |
| CN | 105487337 A | 4/2016 |
| CN | 106019830 A | 10/2016 |
| CN | 106019831 A | 10/2016 |
| CN | 106019833 A | 10/2016 |
| CN | 106462059 A | 2/2017 |
| CN | 107531858 A | 1/2018 |
| CN | 108137478 A | 6/2018 |
| CN | 108290991 A | 7/2018 |
| JP | H5-216244 A | 8/1993 |
| JP | H9-6003 A | 1/1997 |
| JP | H10-186662 A | 7/1998 |
| JP | H11-38623 A | 2/1999 |
| JP | 2002-014465 A | 1/2002 |
| JP | 2005-308977 A | 11/2005 |
| JP | 2008-197226 A | 8/2008 |
| JP | 2008249857 A | 10/2008 |
| JP | 2010230841 A | 10/2010 |
| TW | 201700585 A | 1/2017 |
| TW | 201701063 A | 1/2017 |

OTHER PUBLICATIONS

Notice of Reasons for Refusal issued on Sep. 20, 2023, by the Japanese Patent Office in corresponding Japanese Patent Application No. 2019-232508, and an English translation of the Office Action (10 pages).

Ofice Action (First Office Action) issued on Nov. 18, 2023, by the China National Intellectual Property Administration in corresponding Chinese Patent Application No. 201911360456.8, and an English translation of the Office Action. (13 pages).

Office Action (Notice of Grounds for Rejection) issued on Apr. 1, 2024, by the Korean Intellectual Property Office in corresponding Korean Patent Application No. 10-2019-0174219, and an English translation of the Office Action. (9 pages).

Commonly used polymer materials, Engineering Materials, first edition, 2023, p. 206. (1 page).

* cited by examiner

RESIST COMPOSITION AND METHOD FOR PRODUCING RESIST PATTERN

TECHNICAL FIELD

The present invention relates to a resist composition and a method for producing a resist pattern using the resist composition.

BACKGROUND ART

Patent Document 1 and Patent Document 2 mention a resist composition including a resin in which a hydroxy group of cresol novolak is protected with a tert-butoxycarbonyl group.

PRIOR ART DOCUMENT

Patent Document

Patent Document 1: JP 5-216244 A
Patent Document 2: JP 9-6003 A

DISCLOSURE OF THE INVENTION

Problems to be Solved by the Invention

An object of the present invention is to provide a resist composition capable of producing a resist pattern with small change over time and satisfactory pattern shape.

Means for Solving the Problems

The present invention includes the following inventions.
[1] A resist composition comprising a novolak resin in which a hydroxy group is substituted with a group represented by formula (3), an acid generator, a quencher, and a solvent:

$$*-O-\underset{\underset{O}{\parallel}}{C}-O-R^{a10} \quad (3)$$

wherein, in formula (3), $R^{a10}$ represents a hydrocarbon group having 1 to 20 carbon atoms and * represents a bond.

[2] The resist composition according to [1], wherein the novolak resin is a phenol novolak resin.

[3] The resist composition according to [1] or [2], further comprising a resin having a group represented by formula (2):

$$*-O-\underset{\underset{R^{a2'}}{|}}{\overset{R^{a1'}}{C}}-O-R^{a3'} \quad (2)$$

wherein, in formula (2), $R^{a1'}$ and $R^{a2'}$ each independently represent a hydrogen atom or a hydrocarbon group having 1 to 12 carbon atoms, and $R^{a3'}$ represents a hydrocarbon group having 1 to 20 carbon atoms, or
$R^{a1'}$ represents a hydrogen atom or a hydrocarbon group having 1 to 12 carbon atoms, $R^{a2'}$ and $R^{a3'}$ are bonded to each other to form a heterocyclic group having 2 to 20 carbon atoms together with carbon atoms and oxygen atoms to which $R^{a2'}$ and $R^{a3'}$ are bonded, a methylene group included in the hydrocarbon group having 1 to 12 carbon atoms, the hydrocarbon group having 1 to 20 carbon atoms, and the heterocyclic group having 2 to 20 carbon atoms may be substituted with an oxygen atom or a sulfur atom, and * represents a bond.

[4] The resist composition according to [3], wherein the resin having a group represented by formula (2) is a resin including a structural unit represented by formula (a1-2):

$$\left[ CH_2 - \underset{\underset{(R^{a6})_m}{\bigcirc}}{\overset{R^{a5}}{\underset{|}{C}}} \right] \quad (a1-2)$$

with pendant $-O-\underset{\underset{R^{a2'}}{|}}{\overset{R^{a1'}}{C}}-O-R^{a3'}$ wherein, in formula (a1-2),
$R^{a1'}$ and $R^{a2'}$ each independently represent a hydrogen atom or a hydrocarbon group having 1 to 12 carbon atoms, $R^{a3'}$ represents a hydrocarbon group having 1 to 20 carbon atoms, or
$R^{a1'}$ represents a hydrogen atom or a hydrocarbon group having 1 to 12 carbon atoms, $R^{a2'}$ and $R^{a3'}$ are bonded to each other to form a divalent heterocyclic group having 2 to 20 carbon atoms together with carbon atoms and oxygen atoms to which $R^{a2'}$ and $R^{a3'}$ are bonded, a methylene group included in the hydrocarbon group having 1 to 12 carbon atoms, the hydrocarbon group having 1 to 20 carbon atoms, and the heterocyclic group having 2 to 20 carbon atoms may be substituted with an oxygen atom or a sulfur atom,
$R^{a5}$ represents a hydrogen atom or a methyl group,
$R^{a6}$ represents an alkyl group having 1 to 6 carbon atoms or an alkoxy group having 1 to 6 carbon atoms, and
m represents an integer of 0 to 4, and when m is 2 or more, a plurality of $R^{a6}$ may be the same or different from each other.

[5] The resist composition according to [3], wherein the resin having a group represented by formula (2) is a novolak resin and a hydroxy group of the novolak resin is substituted with a group represented by formula (2).

[6] A method for producing a resist pattern, which comprises:
(1) a step of applying the resist composition according to any one of [1] to [5] on a substrate,
(2) a step of drying the applied composition to form a composition layer,
(3) a step of exposing the composition layer, and
(4) a step of developing the exposed composition layer.

Effects of the Invention

According to the resist composition of the present invention, it is possible to produce a resist pattern with small change over time and satisfactory pattern shape.

BRIEF DESCRIPTION OF THE DRAWINGS

FIG. 1(a) shows a satisfactory cross section in which a top shape and a hemline shape are close to rectangular, and FIG. 1(b) shows a cross section with unsatisfactory top shape.

MODE FOR CARRYING OUT THE INVENTION

Figures 1A, 1B:
FIGS. 1(a) and 1(b) show a schematic diagram of a cross-sectional shape of a line pattern.

In the present description, unless otherwise specified, "(meth)acrylate" means "at least one selected from the group consisting of acrylate and methacrylate". Terms "(meth)acrylic acid" and "(meth)acryloyl" have the same meaning. When a structural unit having "CH$_2$═C(CH$_3$)—CO—" or "CH$_2$═CH—CO—" is exemplified, a structural unit having both groups shall be similarly exemplified. When stereoisomers exist, all stereoisomers are included.

In the present description, "solid component of resist composition" means the total of components excluding the below-mentioned solvent (D) from the total amount of the resist composition.

[Resist Composition]

The resist composition of the present invention is a resist composition including a resin (hereinafter sometimes referred to as "resin (A)"), an acid generator (hereinafter sometimes referred to as "acid generator (B)"), a quencher (hereinafter sometimes referred to as "quencher (C)"), and a solvent (hereinafter sometimes referred to as "solvent (D)"). The resin (A) includes a novolak resin in which a hydroxy group of the novolak resin is substituted with a group represented by formula (3) (hereinafter sometimes referred to as "resin (A1)").

The resin (A) may further include a resin different from the resin (A1) (hereinafter sometimes referred to as resin (A2) and resin (A3)).

The resist composition of the present invention may further include an adhesion improver (hereinafter sometimes referred to as "adhesion improver (E)").

[Resin (A1)]

The resin (A1) means a novolak resin in which a hydroxy group is substituted with a group represented by formula (3), which is a resin in which a hydroxy group possessed by the novolak resin is partially substituted with a group represented by formula (3):

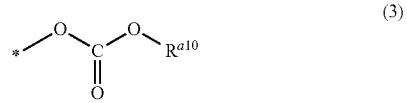
(3)

wherein, in formula (3), $R^{a10}$ represents a hydrocarbon group having 1 to 20 carbon atoms and * represents a bond.

Examples of the hydrocarbon group represented by $R^{a10}$ include a chain hydrocarbon group (an alkyl group, an alkenyl group and an alkynyl group), an alicyclic hydrocarbon group, an aromatic hydrocarbon group, and groups formed by combining these groups.

Examples of the alkyl group include a methyl group, an ethyl group, a propyl group, a butyl group, a pentyl group, a hexyl group, a heptyl group, and an octyl group.

Examples of the alkenyl group include an ethenyl group, a propenyl group, an isopropenyl group, a butenyl group, an isobutenyl group, a tert-butenyl group, a pentenyl group, a hexenyl group, a heptenyl group, an octenyl group, an isooctynyl group, a nonenyl group and the like.

Examples of the alkynyl group include an ethynyl group, a propynyl group, an isopropynyl group, a butynyl group, an isobutynyl group, a tert-butynyl group, a pentynyl group, a hexynyl group, an octynyl group, a nonynyl group and the like.

The alicyclic hydrocarbon group may be either monocyclic or polycyclic. Examples of the monocyclic alicyclic hydrocarbon group include cycloalkyl groups such as a cyclopentyl group, a cyclohexyl group, a cycloheptyl group, and a cyclooctyl group. Examples of the polycyclic alicyclic hydrocarbon group include a decahydronaphthyl group, an adamantyl group, a norbornyl group, and the following groups (* represents a bond). The number of carbon atoms of the alicyclic hydrocarbon group in $R^{a10}$ is preferably 3 to 16.

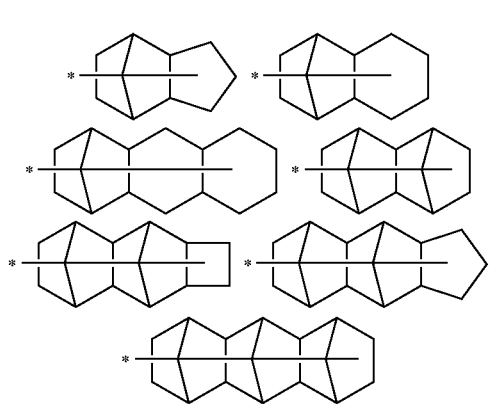

Examples of the aromatic hydrocarbon group include aryl groups such as a phenyl group, a naphthyl group, an anthryl group, a biphenyl group, and a phenanthryl group.

Examples of the group formed by combination include a group obtained by combining an alkyl group with an alicyclic hydrocarbon group, a group obtained by combining an alkyl group with an aromatic hydrocarbon group, and a group obtained by combining an aromatic hydrocarbon group with an alicyclic hydrocarbon group.

Examples of the group obtained by combining an alkyl group with an alicyclic hydrocarbon group include alkylcycloalkyl groups such as a methylcyclohexyl group, a dimethylcyclohexyl group, and a methylnorbornyl group; and cycloalkylalkyl groups such as a cyclohexylmethyl group, an adamantylmethyl group, an adamantylethyl group, and a norbornylethyl group.

Examples of the group obtained by combining an alkyl group with an aromatic hydrocarbon group include aralkyl groups such as a benzyl group, a phenethyl group, a phenylpropyl group, a trityl group, a naphthylmethyl group, a naphthylethyl group, a p-methylphenyl group, a p-tert-butylphenyl group, a tolyl group, a xylyl group, a cumenyl group, a mesityl group, a 2,6-diethylphenyl group, and a 2-methyl-6-ethylphenyl group.

Examples of the group obtained by combining an aromatic hydrocarbon group with an alicyclic hydrocarbon group include aryl-cycloalkyl groups such as a phenylcyclohexyl group; and aromatic hydrocarbon groups having an alicyclic hydrocarbon group, such as a p-adamantylphenyl group.

The group represented by formula (3) is preferably an acid-labile group.

The acid-labile group means a group having a leaving group which is eliminated by contact with an acid, thus forming a hydrophilic group (e.g. a hydroxy group or a carboxy group).

When the group represented by formula (3) is an acid-labile group, the group represented by formula (3) is preferably a group represented by formula (3A):

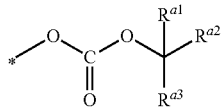
(3A)

wherein, in formula (3A), $R^{a1}$, $R^{a2}$, and $R^{a3}$ each independently represent an alkyl group having 1 to 8 carbon atoms or an alicyclic hydrocarbon group having 3 to 20 carbon atoms, or
$R^{a1}$ and $R^{a2}$ may be bonded to each other to form an alicyclic hydrocarbon group having 3 to 20 carbon atoms together with carbon atoms to which $R^{a1}$ and $R^{a2}$ are bonded, $R^{a3}$ represents an alkyl group having 1 to 8 carbon atoms or an alicyclic hydrocarbon group having 3 to 20 carbon atoms, and * represents a bond.

Examples of the alkyl group of $R^{a1}$, $R^{a2}$, and $R^{a3}$ include a methyl group, an ethyl group, a propyl group, a butyl group, a pentyl group, a hexyl group, a heptyl group, an octyl group and the like.

The alicyclic hydrocarbon group of $R^{a1}$, $R^{a2}$, and $R^{a3}$ may be either monocyclic or polycyclic. Examples of the monocyclic alicyclic hydrocarbon group include cycloalkyl groups such as a cyclopentyl group, a cyclohexyl group, a cycloheptyl group, and a cyclooctyl group. Examples of the polycyclic alicyclic hydrocarbon group include a decahydronaphthyl group, an adamantyl group, a norbornyl group, the following groups (* represents a bond) and the like.

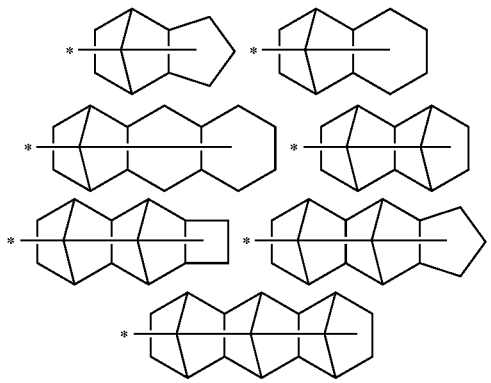

The alicyclic hydrocarbon group of $R^{a1}$, $R^{a2}$, and $R^{a3}$ preferably has 3 to 16 carbon atoms.

When Rai and $R^{a2}$ are bonded to each other to form an alicyclic hydrocarbon group, examples of $-C(R^{a1})(R^{a2})(R^{a3})$ include the following groups. The alicyclic hydrocarbon group preferably has 3 to 12 carbon atoms. * represents a bond to —O—.

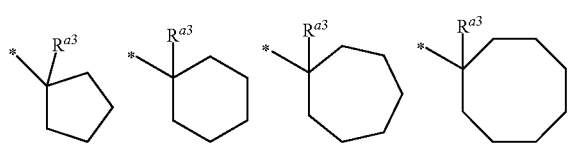

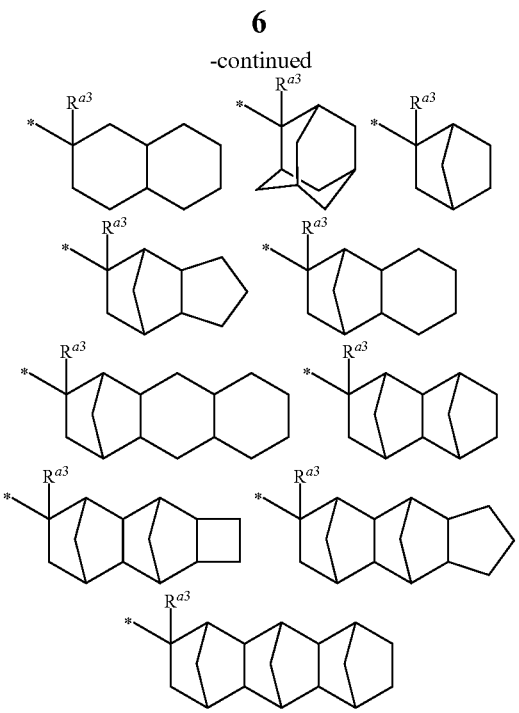

Examples of the group represented by formula (3A) include an alkoxycarbonyloxy group (a group in which, in formula (3A), all of $R^{a1}$, $R^{a2}$ and $R^{a3}$ are an alkyl group, and preferably a tert-butoxycarbonyloxy group), a 1-alkylcyclopentan-1-yloxycarbonyloxy group and a 1-alkylcyclohexan-1-yloxycarbonyloxy group (groups in which, in formula (3A), Rai and $R^{a2}$ are bonded to form a cyclopentyl group or a cyclohexyl group, and $R^{a3}$ is an alkyl group), and a 1-(cyclopentan-1-yl)-1-alkylalkoxycarbonyloxy group and a 1-(cyclohexan-1-yl)-1-alkylalkoxycarbonyloxy group (groups in which, in formula (3A), $R^{a1}$ and $R^{a2}$ are an alkyl group and $R^{a3}$ is a cyclopentyl group or a cyclohexyl group).

Specific examples of the group represented by formula (3A) include the following groups.

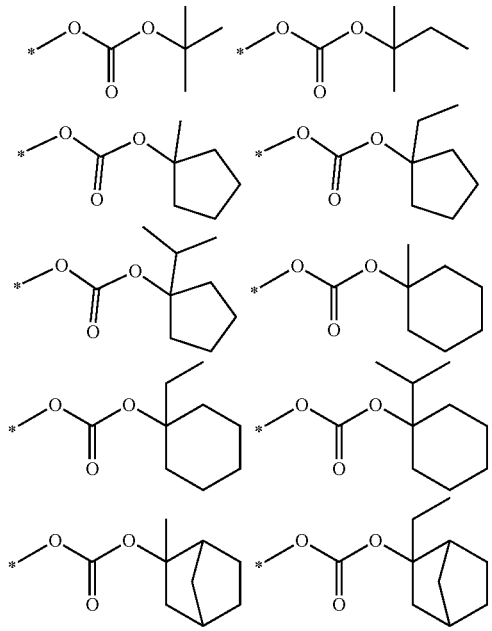

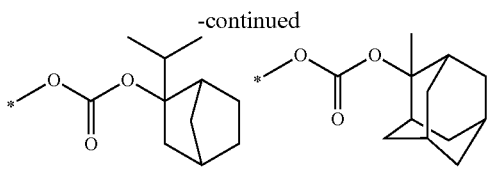
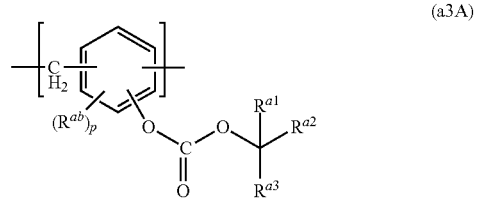
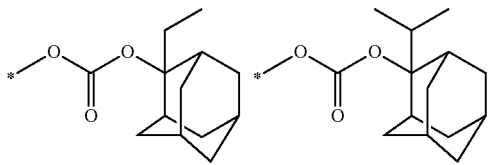

Examples of the novolak resin in which a hydroxy group is substituted with a group represented by formula (3) include a resin including a structural unit represented by formula (a3) (hereinafter sometimes referred to as "structural unit (a3)"):

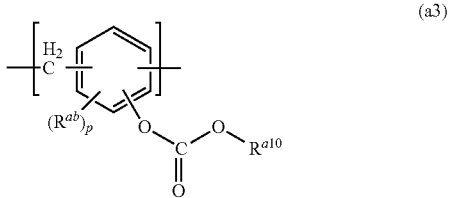

wherein, in formula (a3), $R^{a10}$ represents a hydrocarbon group having 1 to 20 carbon atoms, $R^{ab}$ represents a hydroxy group, an alkyl group having 1 to 6 carbon atoms or an alkoxy group having 1 to 6 carbon atoms, and p represents an integer of 0 to 3, and when p is 2 or more, a plurality of $R^{ab}$ may be the same or different from each other.

Examples of the hydrocarbon group of $R^{a10}$ include the same groups as the groups mentioned above.

Examples of the alkyl group of $R^{ab}$ include a methyl group, an ethyl group, a propyl group, a butyl group, a pentyl group, a hexyl group and the like. The alkyl group having 1 to 6 carbon atoms of $R^{ab}$ is preferably an alkyl group having 1 to 3 carbon atoms, and more preferably a methyl group.

Examples of the alkoxy group of $R^{ab}$ include a methoxy group, an ethoxy group, a propoxy group, a butoxy group, a pentyloxy group, a hexyloxy group and the like. The alkoxy group having 1 to 6 carbon atoms of $R^{ab}$ is preferably an alkoxy group having 1 to 3 carbon atoms, and more preferably a methoxy group.

p is preferably 0 or 1.

Examples of the novolak resin in which a hydroxy group is substituted with a group represented by formula (3A) include a resin including a structural unit represented by formula (a3A) (hereinafter sometimes referred to as "structural unit (a3A)"):

wherein, in formula (a3A), $R^{a1}$, $R^{a2}$, and $R^{a3}$ each independently represent an alkyl group having 1 to 8 carbon atoms or an alicyclic hydrocarbon group having 3 to 20 carbon atoms, or $R^{a1}$ and $R^{a2}$ may be bonded to each other to form an alicyclic hydrocarbon group having 3 to 20 carbon atoms together with carbon atoms to which $R^{a1}$ and $R^{a2}$ are bonded, $R^{a3}$ represents an alkyl group having 1 to 8 carbon atoms or an alicyclic hydrocarbon group having 3 to 20 carbon atoms, $R^{ab}$ represents a hydroxy group, an alkyl group having 1 to 6 carbon atoms or an alkoxy group having 1 to 6 carbon atoms, and p represents an integer of 0 to 3, and when p is 2 or more, a plurality of $R^{ab}$ may be the same or different from each other.

Examples of the alkyl group and the alicyclic hydrocarbon group of $R^{a1}$, $R^{a2}$, and $R^{a3}$ include the same groups as the groups mentioned above.

When Rai and $R^{a2}$ are bonded to each other to form an alicyclic hydrocarbon group, examples of —C($R^{a1}$) ($R^{a2}$) ($R^{a3}$) include the same groups as the groups mentioned above.

Examples of the alkyl group and the alkoxy group of $R^{ab}$ include the same groups as the groups mentioned above.

The ratio of the hydroxy group in the novolak resin to be substituted with a group represented by formula (3) is usually 3 to 80%, preferably 5 to 70%, and more preferably 8 to 60%.

The novolak resin is a resin obtained by condensing a phenol compound with aldehyde in the presence of a catalyst. Examples of the phenol compound include phenol; o-, m- or p-cresol; 2,3-, 2,5-, 3,4-, or 3,5-xylenol; 2,3,5-trimethylphenol; 2-, 3-, or 4-tert-butylphenol; 2-tert-butyl-4- or 5-methylphenol; 2-, 4-, or 5-methylresorcinol; 2-, 3-, or 4-methoxyphenol; 2,3-, 2,5-, or 3,5-dimethoxyphenol; 2-methoxyresorcinol; 4-tert-butylcatechol; 2-, 3-, or 4-ethylphenol; 2,5- or 3,5-diethylphenol; 2,3,5-triethylphenol; 2-naphthol; 1,3-, 1,5-, or 1,7-dihydroxynaphthalene; and a polyhydroxytriphenylmethane-based compound obtained by condensation of xylenol with hydroxybenzaldehyde. These phenol compounds can be used alone, or two or more phenol compounds can be used in combination. Of these, the phenol compound to be used in the resin (A1) is preferably phenol, o-cresol, m-cresol, or p-cresol, and more preferably phenol.

Examples of the aldehyde include aliphatic aldehydes such as formaldehyde, acetaldehyde, propionaldehyde, n-butylaldehyde, isobutylaldehyde, acrolein, or crotonaldehyde; alicyclic aldehydes such as cyclohexanealdehyde, cyclopentanealdehyde, or furylacrolein; aromatic aldehydes such as furfural, benzaldehyde, o-, m-, or p-methylbenzaldehyde, p-ethylbenzaldehyde, 2,4-, 2,5-, 3,4-, or 3,5-dimethylbenzaldehyde, or o-, m-, or p-hydroxybenzaldehyde; and araliphatic aldehydes such as phenylacetaldehyde or cinnamaldehyde. These aldehydes can be used alone, or two or more aldehydes can be used in combination. Of these aldehydes, formaldehyde is preferable since it is industrially available.

Examples of the catalyst to be used for condensation of a phenol compound with aldehyde include inorganic acids such as hydrochloric acid, sulfuric acid, perchloric acid, or phosphoric acid; organic acids such as formic acid, acetic acid, oxalic acid, trichloroacetic acid, or p-toluenesulfonic acid; and divalent metal salts such as zinc acetate, zinc chloride, or magnesium acetate. These catalysts can be used alone, or two or more catalysts can be used in combination. The amount of the catalyst to be used is, for example, 0.01 to 1 mol based on 1 mol of the aldehyde.

A condensation reaction of a phenol compound with aldehyde can be performed according to a conventional method. The condensation reaction can be performed, for example, by mixing a phenol compound with aldehyde, followed by a reaction at a temperature of 60 to 120° C. for about 2 to 30 hours. The condensation reaction may be performed in the presence of a solvent. Examples of the solvent in the condensation reaction include methyl ethyl ketone, methyl isobutyl ketone, acetone and the like. After completion of the reaction, for example, a solvent insoluble in water is added to the reaction mixture and the reaction mixture is washed with water and then concentrated, as needed, thus making it possible to extract a novolak resin.

Specific examples of the novolak resin in which a hydroxy group is substituted with a group represented by formula (3) include resins including structural units represented by formula (A1-1) to formula (A1-6).

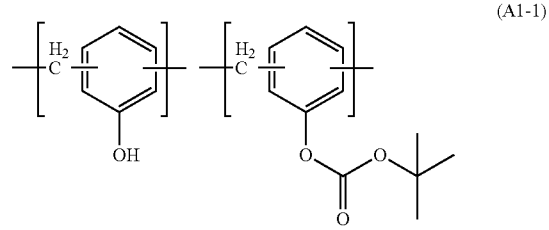

(A1-1)

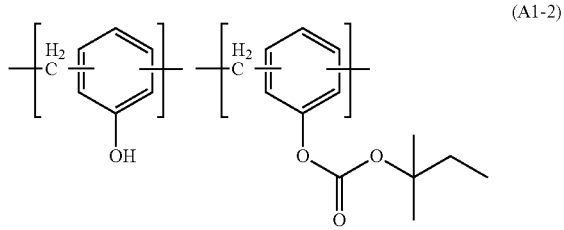

(A1-2)

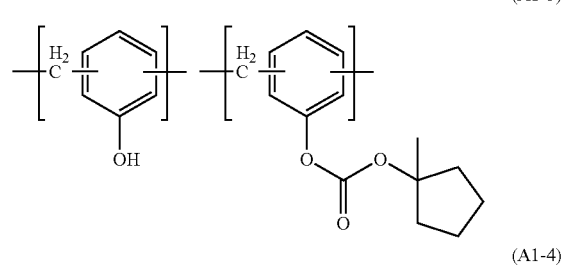

(A1-3)

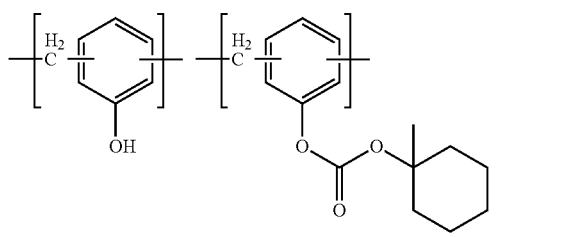

(A1-4)

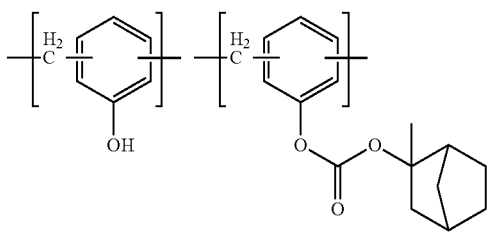

(A1-5)

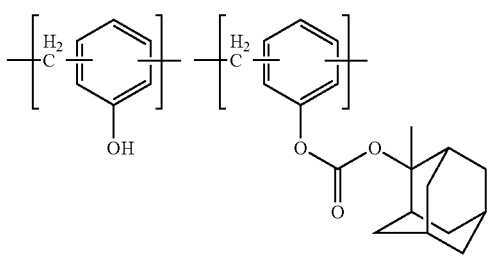

(A1-6)

The resin (A1) has a mass-average molecular weight of 3,000 to 12,000, preferably 4,000 to 11,000, and more preferably 5,000 to 10,000.

The content of the resin (A1) is preferably 1% by mass or more, more preferably 2% by mass or more, and still more preferably 3% by mass or more, and is preferably 80% by mass or less, more preferably 70% by mass or less, and still more preferably 60% by mass or less, based on the total amount of the resin included in the resist composition.

[Resin (A2)]

The resin (A2) is a resin having a group represented by formula (2):

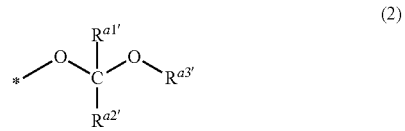

(2)

wherein, in formula (2), $R^{a1'}$ and $R^{a2'}$ each independently represent a hydrogen atom or a hydrocarbon group having 1 to 12 carbon atoms, and $R^{a3'}$ represents a hydrocarbon group having 1 to 20 carbon atoms, or $R^{a1'}$ represents a hydrogen atom or a hydrocarbon group having 1 to 12 carbon atoms, and $R^{a2'}$ and $R^{a3'}$ are bonded to each other to form a heterocyclic group having 2 to 20 carbon atoms together with carbon atoms and oxygen atoms to which $R^{a2'}$ and $R^{a3'}$ are bonded, a methylene group included in the hydrocarbon group having 1 to 12 carbon atoms, the hydrocarbon group having 1 to 20 carbon atoms, and the heterocyclic group having 2 to 20 carbon atoms may be substituted with an oxygen atom or a sulfur atom, and * represents a bond.

The group represented by formula (2) acts as an acid-labile group.

Examples of the hydrocarbon group represented by $R^{a1'}$, $R^{a2'}$, and $R^{a3'}$ include a chain hydrocarbon group (an alkyl group, an alkenyl group, and an alkynyl group), an alicyclic hydrocarbon group, and an aromatic hydrocarbon group, and groups formed by combining these groups.

Examples of the alkyl group include a methyl group, an ethyl group, a propyl group, a butyl group, a pentyl group, a hexyl group, a heptyl group, an octyl group, a decyl group, and a dodecyl group.

Examples of the alkenyl group include an ethenyl group, a propenyl group, an isopropenyl group, a butenyl group, an isobutenyl group, a tert-butenyl group, a pentenyl group, a hexenyl group, a heptenyl group, an octynyl group, an isooctynyl group, and a nonenyl group.

Examples of the alkynyl group include an ethynyl group, a propynyl group, an isopropynyl group, a butynyl group, an isobutynyl group, a tert-butynyl group, a pentynyl group, a hexynyl group, an octynyl group, a nonynyl group and the like.

Examples of the alicyclic hydrocarbon group include cycloalkyl groups such as a cyclopentyl group, a cyclohexyl group, a cycloheptyl group, and a cyclooctyl group; and polycyclic alicyclic hydrocarbon groups such as a decahydronaphthyl group, an adamantyl group, and a norbornyl group.

Examples of the aromatic hydrocarbon group include aryl groups such as a phenyl group, a naphthyl group, an anthryl group, a biphenyl group, and a phenanthryl group.

Examples of the group formed by combination include a group obtained by combining an alkyl group with an alicyclic hydrocarbon group, a group obtained by combining an alkyl group with an aromatic hydrocarbon group, and a group obtained by combining an aromatic hydrocarbon group with an alicyclic hydrocarbon group.

Examples of the group obtained by combining an alkyl group with an alicyclic hydrocarbon group include a methylcyclohexyl group, a dimethylcyclohexyl group, a methylnorbornyl group, an isobornyl group, and a 2-alkyladamantan-2-yl group.

The group obtained by combining an alkyl group with an aromatic hydrocarbon group is, for example, an aralkyl group, and specific examples thereof include a benzyl group, a phenethyl group, a phenylpropyl group, a trityl group, a naphthylmethyl group, a naphthylethyl group, a p-methylphenyl group, a p-tert-butylphenyl group, a tolyl group, a xylyl group, a cumenyl group, a mesityl group, a 2,6-diethylphenyl group, a 2-methyl-6-ethylphenyl group and the like.

Examples of the group obtained by combining an aromatic hydrocarbon group with an alicyclic hydrocarbon group include aryl-cycloalkyl groups such as a phenylcyclohexyl group; and aromatic hydrocarbon groups having an alicyclic hydrocarbon group, such as a p-adamantylphenyl group.

When $R^{a2'}$ and $R^{a3'}$ are bonded to each other to form an heterocyclic group together with carbon atoms and oxygen atoms to which $R^{a2'}$ and $R^{a3'}$ are bonded, examples of —C($R^{a1'}$)($R^{a2'}$)—O—$R^{a3'}$ include the following groups and the like. * represents a bond.

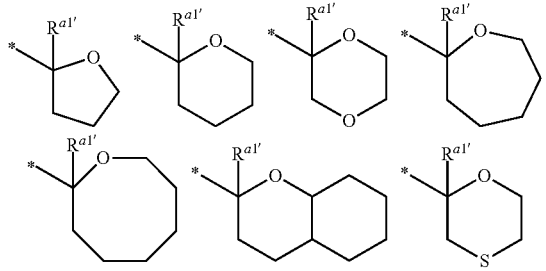

$R^{a1'}$ is preferably a hydrogen atom.

$R^{a2'}$ is preferably a hydrocarbon group having 1 to 12 carbon atoms, and more preferably a methyl group and an ethyl group.

The hydrocarbon group of $R^{a3'}$ is preferably an alkyl group having 1 to 18 carbon atoms, an alicyclic hydrocarbon group having 3 to 18 carbon atoms, an aromatic hydrocarbon group having 6 to 18 carbon atoms, or groups obtained by combining these groups, and more preferably an alkyl group having 1 to 18 carbon atoms, an alicyclic aliphatic hydrocarbon group having 3 to 18 carbon atoms, or an aralkyl group having 7 to 18 carbon atoms. The alkyl group and the alicyclic hydrocarbon group are preferably unsubstituted. When the aromatic hydrocarbon group has a substituent, the substituent is preferably an aryloxy group having 6 to 10 carbon atoms.

Specific examples of the group represented by formula (2) include the following groups.

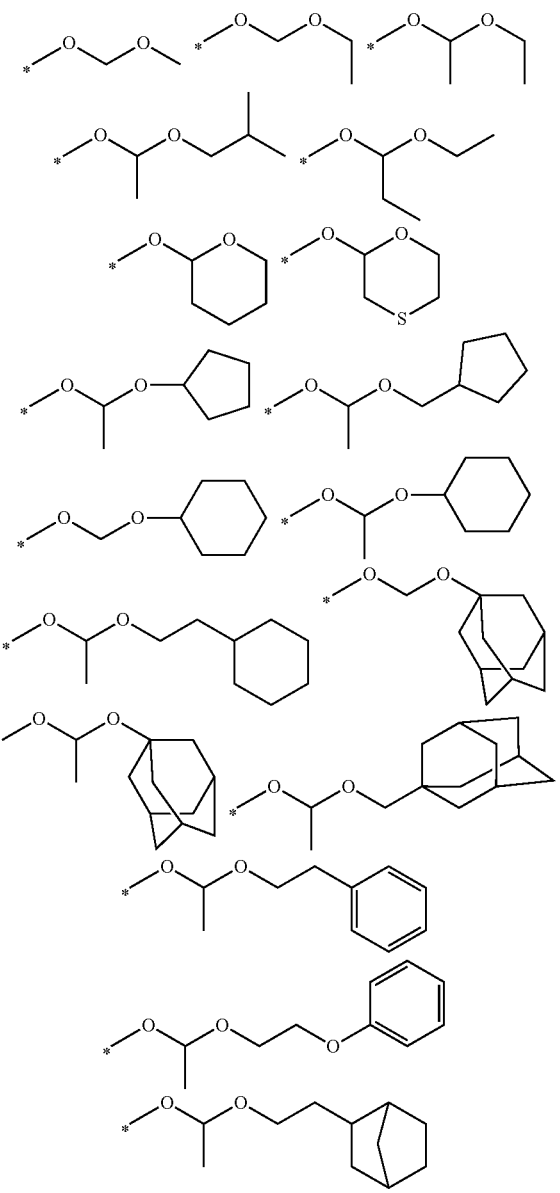

-continued

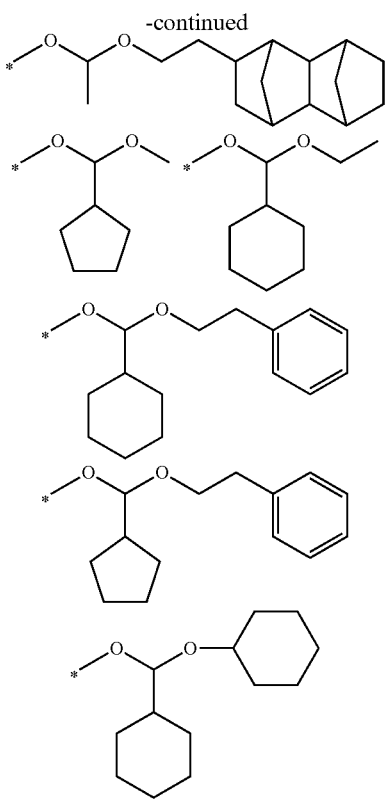

Examples of the resin having a group represented by formula (2) include a resin including a structural unit represented by formula (a1-2) (hereinafter sometimes referred to as "structural unit (a1-2)"):

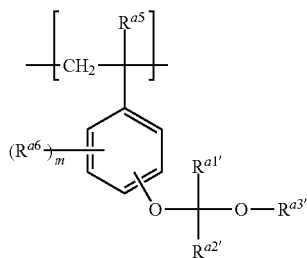

wherein, in formula (a1-2), $R^{a1'}$ and $R^{a2'}$ each independently represent a hydrogen atom or a hydrocarbon group having 1 to 12 carbon atoms, and $R^{a3'}$ represents a hydrocarbon group having 1 to 20 carbon atoms, or
$R^{a1'}$ represents a hydrogen atom or a hydrocarbon group having 1 to 12 carbon atoms, and $R^{a2'}$ and $R^{a3'}$ are bonded to each other to form a divalent heterocyclic group having 2 to 20 carbon atoms together with carbon atoms and oxygen atoms to which $R^{a2'}$ and $R^{a3'}$ are bonded, a methylene group included in the hydrocarbon group having 1 to 12 carbon atoms, the hydrocarbon group having 1 to 20 carbon atoms, and the heterocyclic group having 2 to 20 carbon atoms may be substituted with an oxygen atom or a sulfur atom, $R^{a5}$ represents a hydrogen atom or a methyl group, $R^{a6}$ represents an alkyl group having 1 to 6 carbon atoms or an alkoxy group having 1 to 6 carbon atoms, and m represents an integer of 0 to 4, and when m is 2 or more, a plurality of $R^{a6}$ may be the same or different from each other.

In formula (a1-2), $R^{a1'}$ is preferably a hydrogen atom. $R^{a2'}$ is preferably a hydrocarbon group having 1 to 12 carbon atoms, and more preferably a methyl group and an ethyl group.

The hydrocarbon group of $R^{a3'}$ is preferably an alkyl group having 1 to 18 carbon atoms, an alicyclic hydrocarbon group having 3 to 18 carbon atoms, an aromatic hydrocarbon group having 6 to 18 carbon atoms, or groups obtained by combining these groups, and more preferably an alkyl group having 1 to 18 carbon atoms, an alicyclic aliphatic hydrocarbon group having 3 to 18 carbon atoms, or an aralkyl group having 7 to 18 carbon atoms. The alkyl group and the alicyclic hydrocarbon group are preferably unsubstituted. When the aromatic hydrocarbon group has a substituent, the substituent is preferably an aryloxy group having 6 to 10 carbon atoms.

$R^{a5}$ is preferably a hydrogen atom.

$R^{a6}$ is preferably an alkoxy group having 1 to 4 carbon atoms, more preferably a methoxy group and an ethoxy group, and still more preferably a methoxy group.

m is preferably 0 or 1, and more preferably 0.

Examples of the monomer from which the structural unit (a1-2) is derived include a monomer represented by any one of formula (a1-2-1) to formula (a1-2-14).

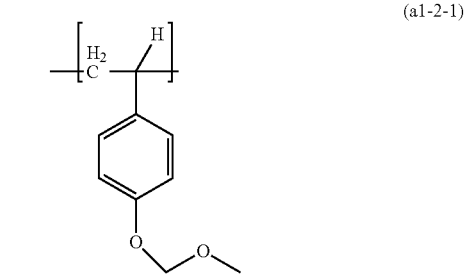

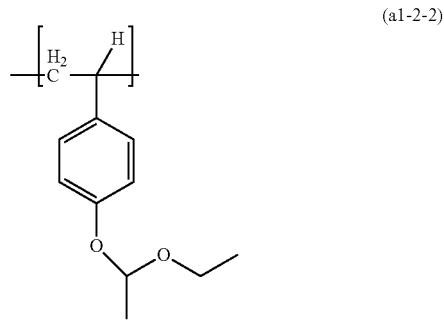

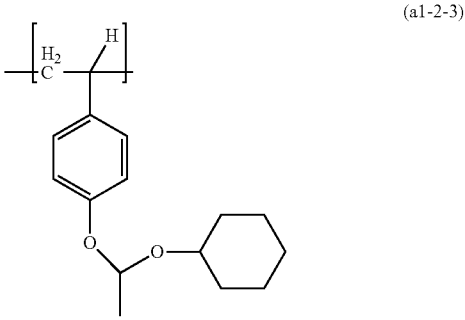

-continued
(a1-2-4)
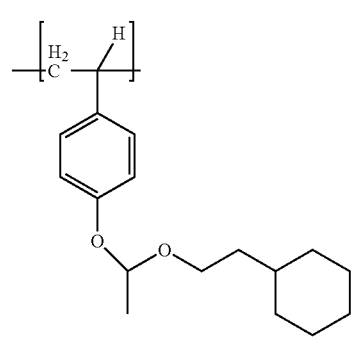
(a1-2-5)
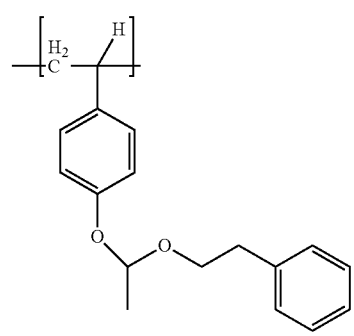
(a1-2-6)
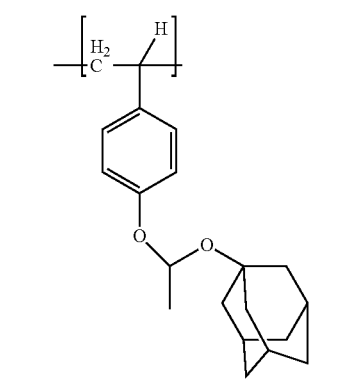
(a1-2-7)
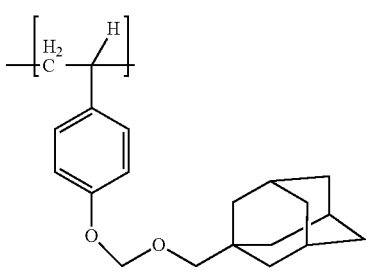
(a1-2-8)
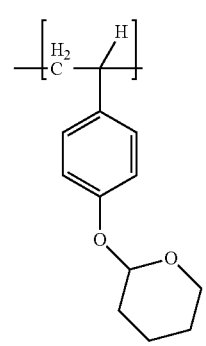
-continued
(a1-2-9)
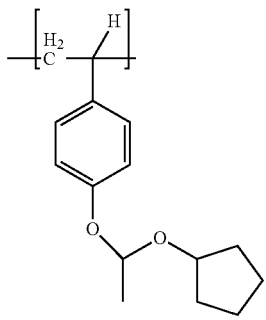
(a1-2-10)
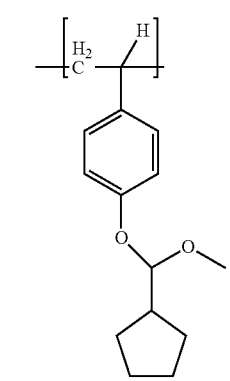
(a1-2-11)
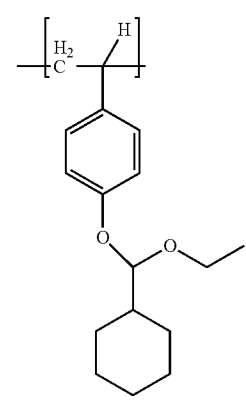
(a1-2-12)
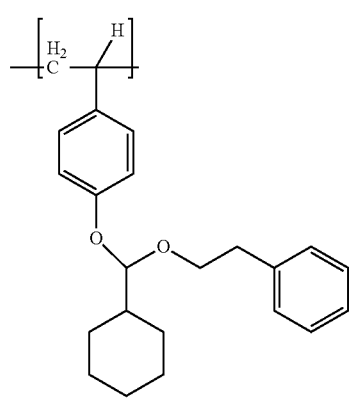

(a1-2-13)

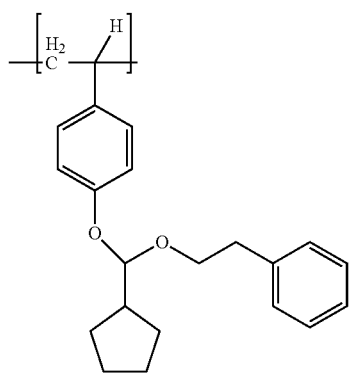

(a1-2-14)

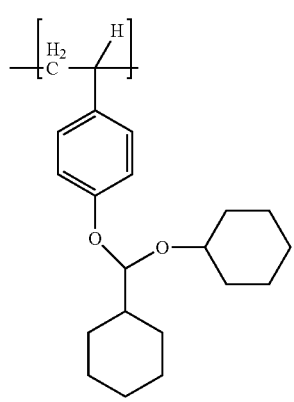

It is also possible to exemplify, as specific examples of the monomer, a monomer in which hydrogen atoms corresponding to $R^{a4}$ and $R^{a5}$ are substituted with a methyl group in the monomers.

Of these, structural units derived from monomers represented by formulas (a1-2-2), formula (a1-2-3), (a1-2-4), (a1-2-9), and (a1-2-14) are preferable, and structural units derived from monomers represented by formula (a1-2-2), (a1-2-3), (a1-2-4), and (a1-2-9) are more preferable.

In the resin including a structural unit (a1-2), the content of the structural unit (a1-2) is preferably 10 to 80 mol %, more preferably 20 to 70 mol %, and still more preferably 30 to 60 mol %, based on all structural units of the resin (A2).

The resin including a structural unit (a1-2) may include, in addition to the structural unit (a1-2), structural units known in the art, such as a structural unit having no acid-labile group (hereinafter sometimes referred to as "structural unit (a2)").

In the resin including a structural unit (a1-2), only one structural unit (a2) having no acid-labile group may be included, or a plurality of structural units (a2) may be included.

Examples of the structural unit (a2) include a structural unit represented by any one of formula (a2-1) to formula (a2-3) (hereinafter sometimes referred to as "structural unit (a2-1)" according to the formula number):

(a2-1)

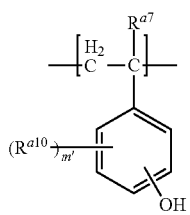

(a2-2)

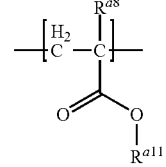

(a2-3)

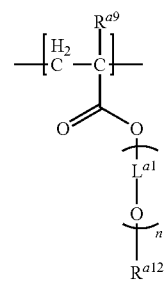

wherein, in formula (a2-1), formula (a2-2), and formula (a2-3), $R^{a7}$, $R^{a8}$, and $R^{a9}$ each independently represent a hydrogen atom or a methyl group, $R^{a10}$ represents an alkyl group having 1 to 6 carbon atoms or an alkoxy group having 1 to 6 carbon atoms, m' represents an integer of 0 to 4, and when m' is 2 or more, a plurality of $R^{a10}$ may be the same or different from each other, $R^{a11}$ represents a hydrogen atom or a primary or secondary hydrocarbon group having 1 to 10 carbon atoms, $R^{a12}$ represents a primary or secondary alkyl group having 1 to 6 carbon atoms, $L^{a1}$ represents an alkanediyl group having 2 to 6 carbon atoms, in which a carbon atom to be bonded to an oxygen atom is a primary or secondary carbon atom, and n represents an integer of 1 to 30, and when n is 2 or more, a plurality of $L^{a1}$ may be the same or different from each other.

Examples of the alkyl group represented by $R^{a10}$ or $R^{a12}$ include a methyl group, an ethyl group, a propyl group, a butyl group, a pentyl group, a hexyl group and the like.

Examples of the alkoxy group represented by $R^{a10}$ include a methoxy group, an ethoxy group, a propoxy group, a butoxy group, a pentyloxy group, a hexyloxy group and the like.

Examples of the hydrocarbon group represented by $R^{a11}$ include an alkyl group, an alicyclic hydrocarbon group, an aromatic hydrocarbon group, and groups formed by combining these groups.

Examples of the alkyl group include a methyl group, an ethyl group, a propyl group, a butyl group, a pentyl group, a hexyl group, a heptyl group, an octyl group, a nonyl group, a decyl group and the like.

The alicyclic hydrocarbon group may be either monocyclic or polycyclic. Examples of the monocyclic alicyclic hydrocarbon group include cycloalkyl groups such as a cyclopentyl group, a cyclohexyl group, a cycloheptyl group, a cyclooctyl group and the like. Examples of the polycyclic alicyclic hydrocarbon group include a decahydronaphthyl group, an adamantyl group, a norbornyl group, and the following groups (* represents a bond).

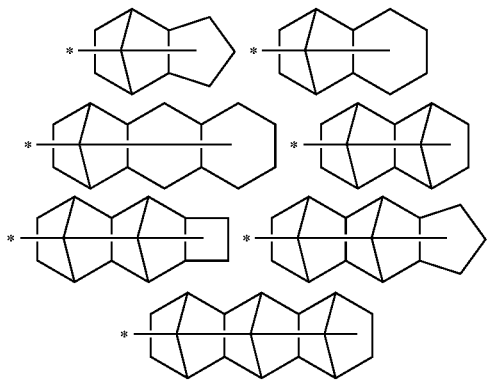

Examples of the group obtained by combining an alkyl group with an alicyclic hydrocarbon group include a methylcyclohexyl group, a dimethylcyclohexyl group, a methylnorbornyl group, a cyclohexylmethyl group, an adamantylmethyl group, a norbornylethyl group and the like.

Examples of the aromatic hydrocarbon group include a phenyl group and a naphthyl group.

Examples of the group obtained by combining an alkyl group with an aromatic hydrocarbon group include aralkyl groups such as a benzyl group.

Examples of the alkanediyl group of $L^{a1}$ include an ethylene group, a propane-1,3-diyl group, a propane-1,2-diyl group, a butane-1,4-diyl group, a pentane-1,5-diyl group, a hexane-1,6-diyl group, an ethane-1,1-diyl group, a propane-1,1-diyl group, and a propane-2,2-diyl group; and branched alkanediyl groups such as a propane-1,2-diyl group, a pentane-2,4-diyl group, a 2-methylpropane-1,3-diyl group, a pentane-1,4-diyl group, and a 2-methylbutane-1,4-diyl group.

$R^{a7}$ is preferably a hydrogen atom.

Preferably, $R^{a8}$ and $R^{a9}$ each independently represent a methyl group.

$R^{a10}$ is preferably an alkoxy group having 1 to 4 carbon atoms, more preferably a methoxy group or an ethoxy group, and still more preferably a methoxy group.

m' is preferably 0 or 1, and more preferably 0.

$R^{a11}$ is preferably a primary or secondary alkyl group having 1 to 6 carbon atoms.

$L^{a1}$ is preferably alkanediyl group having 2 to 4 carbon atoms, more preferably an ethane-1,2-diyl group, a propane-1,3-diyl group, a propane-1,2-diyl group, or a butane-1,4-diyl group, and still more preferably an ethane-1,2-diyl group.

n is preferably an integer of 1 to 10.

$R^{a12}$ is preferably a primary or secondary alkyl group having 1 to 3 carbon atoms.

The structural unit (a2-1) is preferably a structural unit represented by formula (a2-1-1), formula (a2-1-2), formula (a2-1-3), or formula (a2-1-4). Examples of the monomer from which the structural unit (a2-1) is derived include monomers mentioned in JP 2010-204634 A.

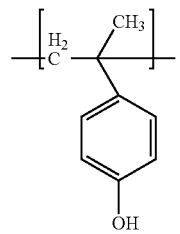

(a2-1-1)

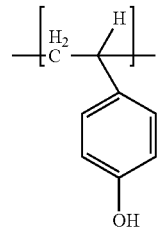

(a2-1-2)

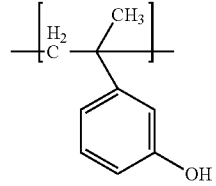

(a2-1-3)

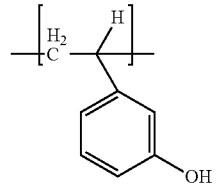

(a2-1-4)

Examples of the monomer from which the structural unit (a2-2) is derived include (meth)acrylic acid alkyl esters such as methyl (meth)acrylate, ethyl (meth)acrylate, propyl (meth)acrylate, butyl (meth)acrylate, and hexyl (meth) acrylate;

(meth)acrylic acid cycloalkyl esters such as cyclopentyl (meth)acrylate and cyclohexyl (meth)acrylate;

polycyclic (meth)acrylic acid esters such as adamantyl (meth)acrylate; and (meth)acrylic acid aryl esters such as phenyl (meth) acrylate and benzyl (meth)acrylate.

Examples of the monomer from which the structural unit (a2-3) is derived include (meth)acrylates such as ethylene glycol monomethyl ether (meth)acrylate, ethylene glycol monoethyl ether (meth)acrylate, ethylene glycol monopropyl ether (meth)acrylate, ethylene glycol monobutyl ether (meth)acrylate, diethylene glycol monomethyl ether (meth) acrylate, triethylene glycol monomethyl ether (meth)acrylate, tetraethylene glycol monomethyl ether (meth)acrylate, pentaethylene glycol monomethyl ether (meth)acrylate, hexaethylene glycol monomethyl ether (meth)acrylate, nonaethylene glycol monomethyl ether (meth)acrylate, and octaethylene glycol monomethyl ether (meth) acrylate.

Examples of the monomer from which the structural unit (a2) is derived include acrylic acid, methacrylic acid, crotonic acid, 2-hydroxyethyl (meth)acrylate, 2-hydroxypropyl (meth)acrylate, styrene, a-methylstyrene, 4-methylstyrene, 2-methylstyrene, 3-methylstyrene, 4-methoxystyrene, 4-isopropoxystyrenen and the like.

The structural unit (a2) may be, for example, a structural unit represented by formula (a2-4):

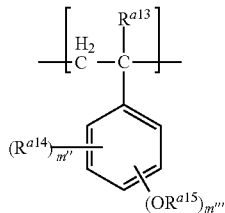

(a2-4)

wherein, in formula (a2-4), $R^{a13}$ represents a hydrogen atom or a methyl group, $R^{a14}$ represents an alkyl group having 1 to 6 carbon atoms or an alkoxy group having 1 to 6 carbon atoms, $R^{a15}$ represents a primary or secondary hydrocarbon group having 1 to 12 carbon atoms, and a methylene group included in the hydrocarbon group may be substituted with an oxygen atom or a carbonyl group, in which a methylene group bonded to an oxygen atom is not substituted with the oxygen atom, m" represents an integer of 0 to 4, and when m" is 2 or more, a plurality of $R^{a14}$ may be the same or different from each other, m'" represents an integer of 0 to 4, and when m'" is 2 or more, a plurality of $R^{a15}$ may be the same or different from each other, and the total of m" and m'" is 5 or less.

Examples of the hydrocarbon group in $R^{a15}$ include a group in which a bond to an oxygen atom is not a tertiary carbon atom, that is, a group in which one or more atoms other than the carbon atoms is bonded to the bonded carbon.

Therefore, the structural unit represented by formula (a2-4) does not include a structural unit (I) and a structural unit (a1-2).

Examples of the alkyl group and the alkoxy group of $R^{a14}$ include the same groups as for $R^{a10}$.

Examples of the hydrocarbon group of $R^{a15}$ include the same groups as for $R^{a11}$.

Of these, $R^{a15}$ is preferably a linear or branched alkyl group having 1 to 5 carbon atoms, an alicyclic hydrocarbon group having 5 to 10 carbon atoms, a phenyl group, or a group formed by combining these groups, or a group in which a carbon atom adjacent to an oxygen atom of these groups is substituted with a carbonyl group.

Examples of the structural unit (a2-4) include structural units represented by formula (a2-4-1) to formula (a2-4-10).

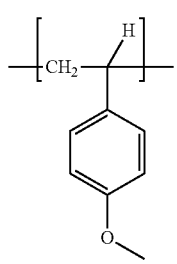

(a2-4-1)

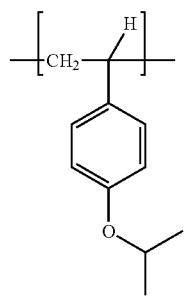

(a2-4-2)

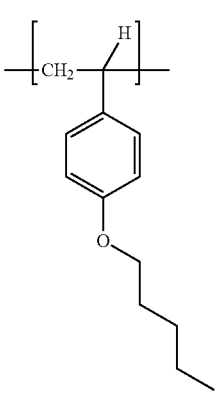

(a2-4-3)

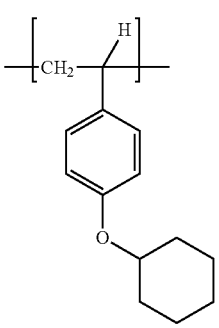

(a2-4-4)

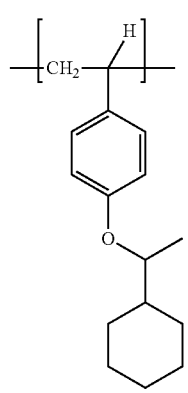

(a2-4-5)

(a2-4-6)
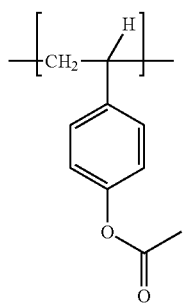

(a2-4-7)
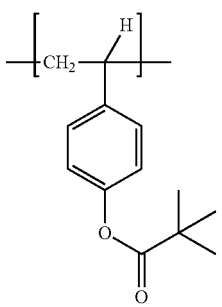

(a2-4-8)
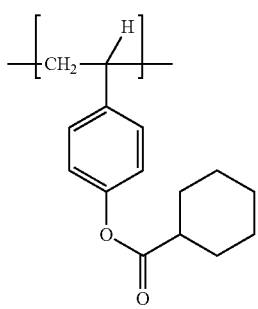

(a2-4-9)
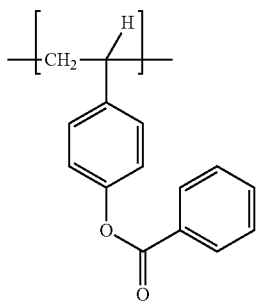

(a2-4-10)
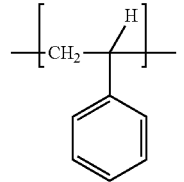

It is also possible to exemplify, as specific examples of the structural unit (a2-4), a structural unit in which a hydrogen atom corresponding to $R^{a13}$ is substituted with a methyl group in the structural units each represented by formula (a2-4-1) to formula (a2-4-10).

When the resin including a structural unit (a1-2) includes a structural unit (a2-1), a structural unit (a2-2), a structural unit (a2-3), and a structural unit (a2-4), the total content of these structural units is preferably 20 to 90 mol %, more preferably 30 to 80 mol %, and still more preferably 40 to 60 mol %, based on all structural units of the resin (A2).

When the resin including a structural unit (a1-2) include a structural unit (a2), the content ratio of the structural unit (a1-2) to the structural unit (a2) [structural unit (a1-2): structural unit (a2)] is preferably 10:90 to 80:20, more preferably 20:80 to 70:30, and still more preferably 30:70 to 60:40, on a molar basis.

Examples of the resin including a structural unit (a1-2) include resins including structural units represented by formula (A2-1) to formula (A2-22).

(A2-1)
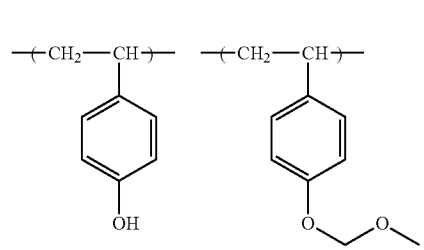

(A2-2)
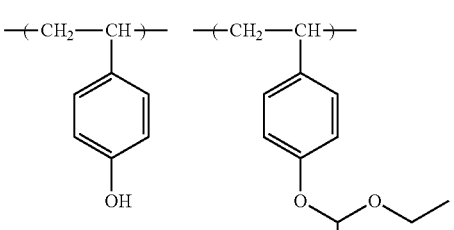

(A2-3)
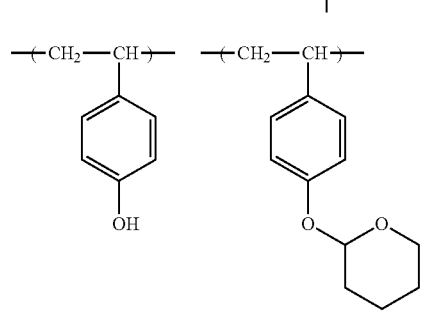

(A2-4)
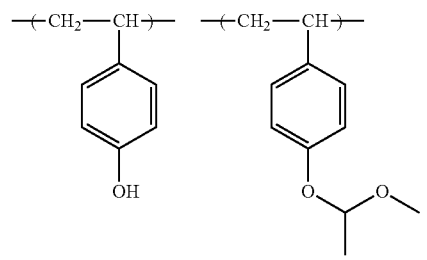

(A2-5)
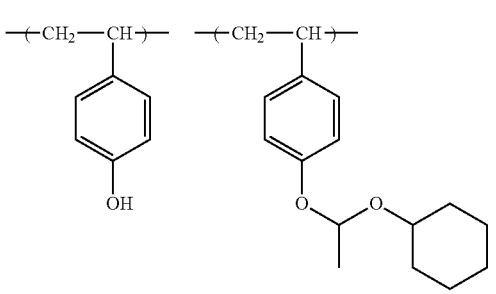

-continued
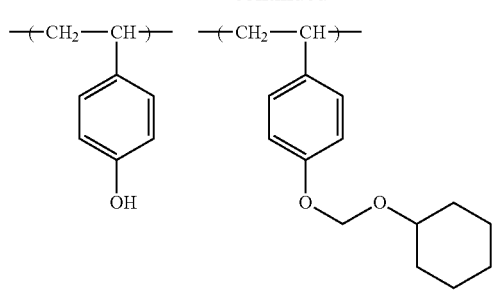 (A2-6)
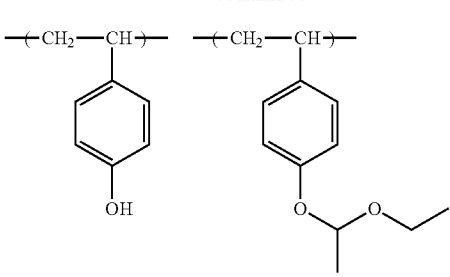 (A2-10)
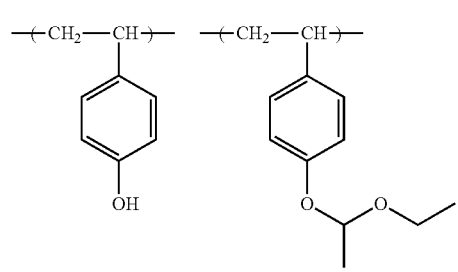 (A2-7)
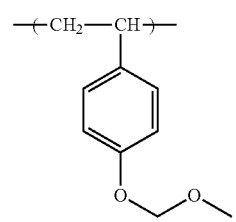 
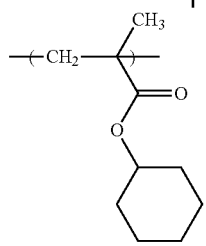
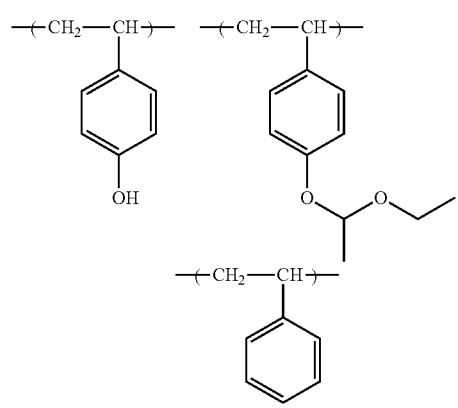 (A2-8)
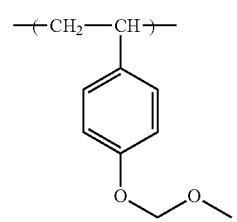 (A2-11)
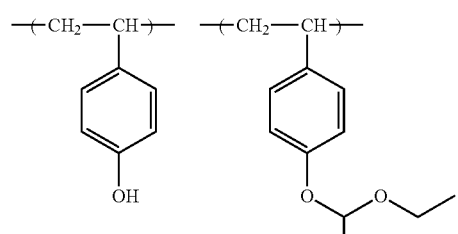 (A2-9)
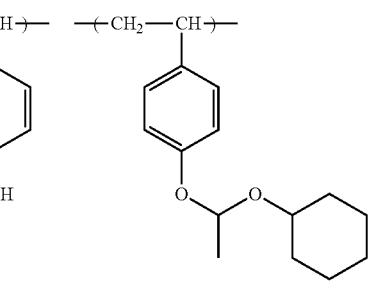
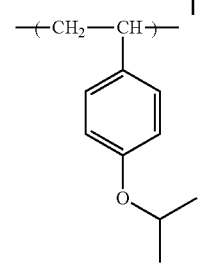
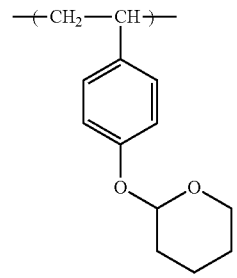 (A2-12)

(A2-13)
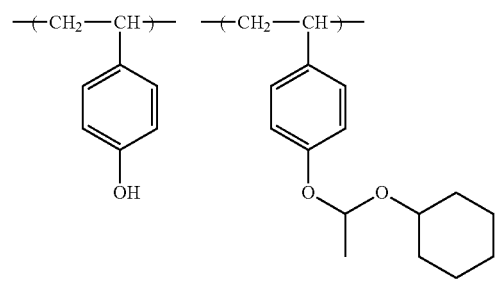
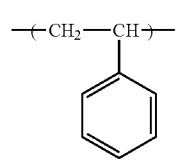
(A2-14)
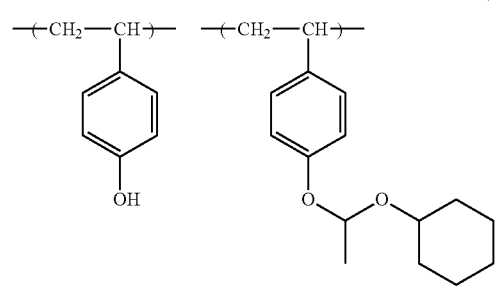
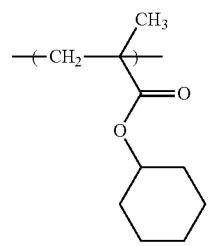
(A2-15)
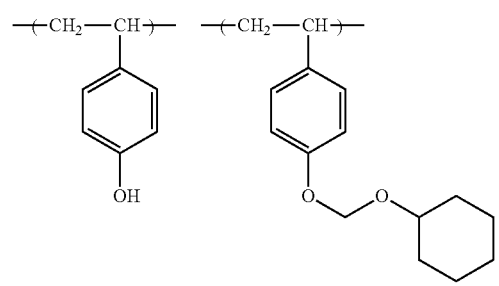
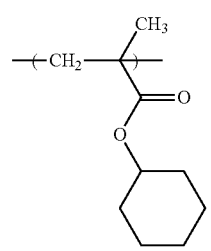
(A2-16)
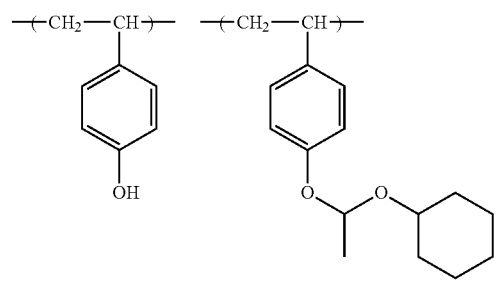
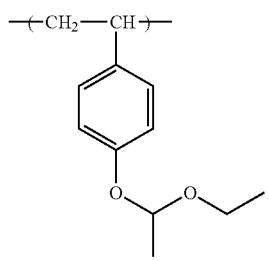
(A2-17)
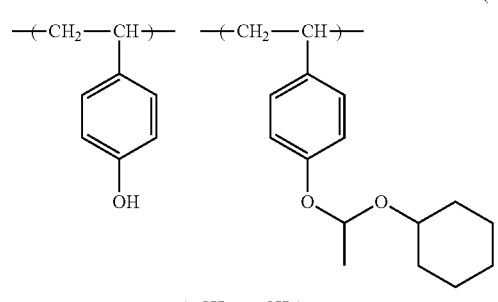
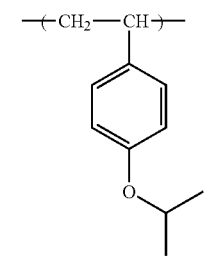
(A2-18)
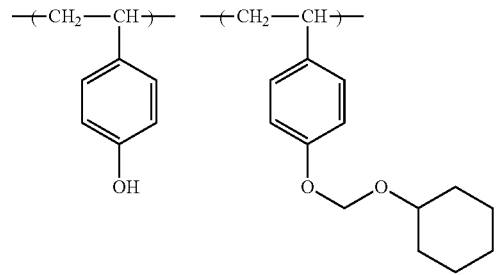
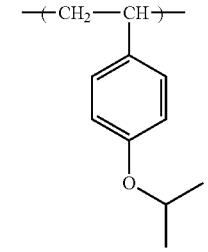

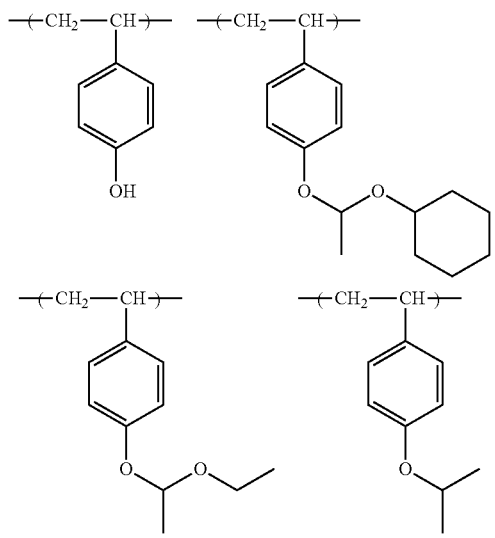

(A2-19)

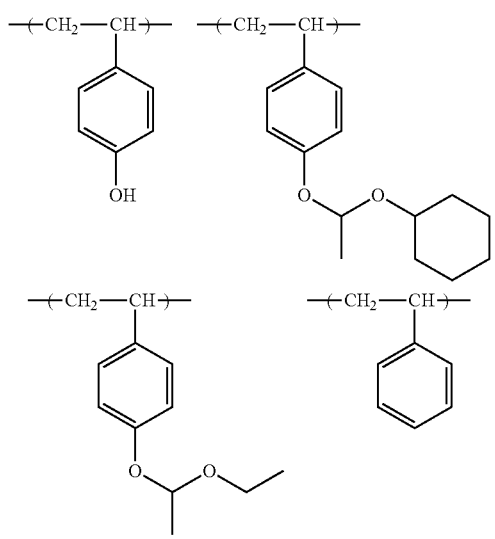

(A2-20)

(A2-21)

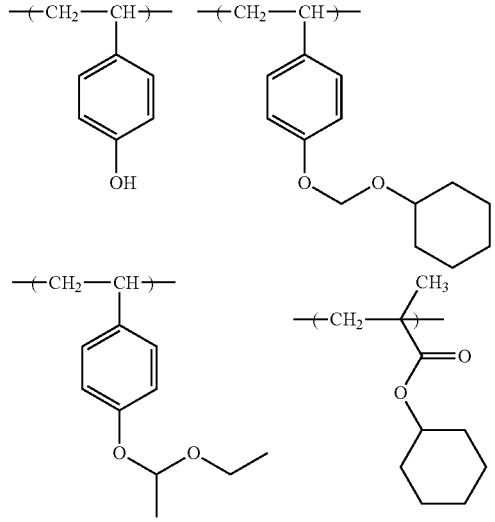

(A2-22)

It is also possible to exemplify, as specific examples of the above structural unit, a structural unit in which a hydrogen atom corresponding to $R^{a5}$ or the like is substituted with a methyl group, or a methyl group is substituted with a hydrogen atom in the above structural formulas. In one resin, a structural unit having a hydrogen atom and a methyl group may coexist.

The resin including a structural unit (a1-2) is preferably a resin including a structural unit (a1-2) and a structural unit (a2), and more preferably a resin including a structural unit (a1-2) and a structural unit (a2-1).

Examples of the resin having a group represented by formula (2) include a resin in which a hydroxy group of a novolak resin is substituted with a group represented by formula (2).

In the resin in which a hydroxy group of a novolak resin is substituted with a group represented by formula (2), examples of the novolak resin include the same novolak resins as exemplified in the above resin (A1).

Examples of the resin in which a hydroxy group of a novolak resin is substituted with a group represented by formula (2) include a resin including a structural unit represented by formula (a4) (hereinafter sometimes referred to as "structural unit (a4)"):

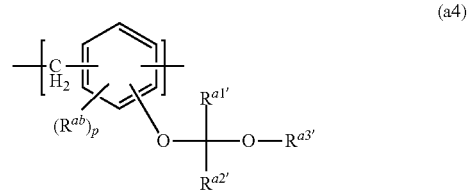

(a4)

wherein, in formula (a4), $R^{a1'}$ and $R^{a2'}$ each independently represent a hydrogen atom or a hydrocarbon group having 1 to 12 carbon atoms, and $R^{a3'}$ represents a hydrocarbon group having 1 to 20 carbon atoms, or $R^{a1'}$ represents a hydrogen atom or a hydrocarbon group having 1 to 12 carbon atoms, and $R^{a2'}$ and $R^{a3'}$ are bonded to each other to form a divalent heterocyclic group having 2 to 20 carbon atoms together with carbon atoms and oxygen atoms to which R$^{a2'}$ and R$^{a3'}$ are bonded, a methylene group included in the hydrocarbon group having 1 to 12 carbon atoms, the hydrocarbon group having 1 to 20 carbon atoms, and the heterocyclic group having 2 to 20 carbon atoms may be substituted with an oxygen atom or a sulfur atom, R$^{ab}$ represents a hydroxy group, an alkyl group having 1 to 6 carbon atoms or an alkoxy group having 1 to 6 carbon atoms, and p represents an integer of 0 to 3, and when p is 2 or more, a plurality of R$^{ab}$ may be the same or different from each other.

Examples of the hydrocarbon group of R$^{a1'}$ R$^{a2'}$, and R$^{a3'}$ include the same groups as the groups mentioned above.

When R$^{a2'}$ and R$^{a3'}$ are bonded to each other to form an heterocyclic group together with carbon atoms and oxygen atoms to which R$^{a2'}$ and R$^{a3'}$ are bonded, examples of —C(R$^{a1'}$) (R$^{a2'}$)—O—R$^{a3'}$ include the same groups as the groups mentioned above.

Examples of the alkyl group of R$^{ab}$ include a methyl group, an ethyl group, a propyl group, a butyl group, a pentyl group, a hexyl group and the like. The alkyl group having 1 to 6 carbon atoms of R$^{ab}$ is preferably an alkyl group having 1 to 3 carbon atoms, and more preferably a methyl group.

Examples of the alkoxy group of R$^{ab}$ include a methoxy group, an ethoxy group, a propoxy group, a butoxy group, a pentyloxy group, a hexyloxy group and the like. The alkoxy group having 1 to 6 carbon atoms of R$^{ab}$ is preferably an alkoxy group having 1 to 3 carbon atoms, and more preferably a methoxy group.

p is preferably 0 or 1.

Examples of the resin in which a hydroxy group of a novolak resin is substituted with a group represented by formula (2) include resins including structural units represented by formula (A2-23) to formula (A2-28).

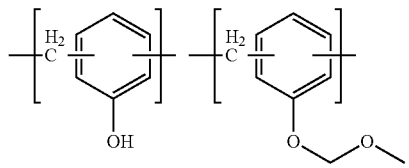
(A2-23)

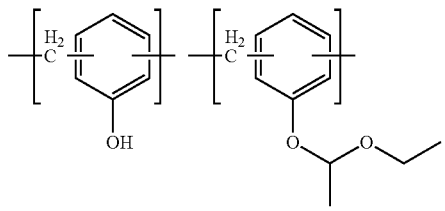
(A2-24)

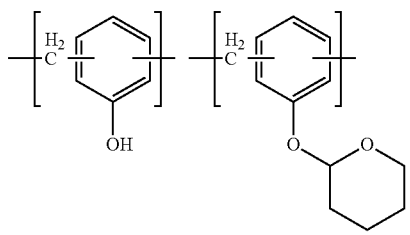
(A2-25)

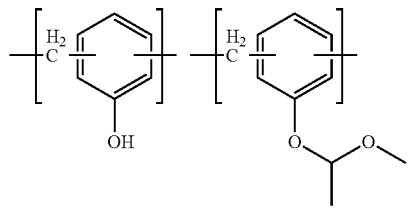
(A2-26)

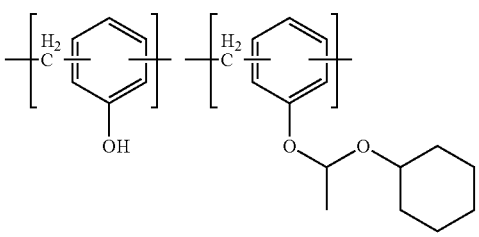
(A2-27)

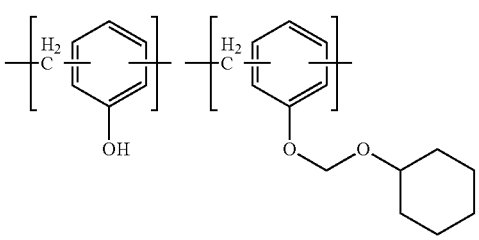
(A2-28)

Specific examples of the resin having a group represented by formula (2) include a resin in which a hydroxy group of polyhydroxystyrene is substituted with a group represented by formula (2), or a resin in which a hydroxy group of a novolak resin is substituted with a group represented by formula (2).

The ratio of the hydroxy group in polyhydroxystyrene to be substituted with the group represented by formula (2) is usually 10 to 80%, preferably 20 to 70%, and more preferably 30 to 60%.

The ratio of the group represented by formula (2) to be introduced into the hydroxy group of the novolak resin is usually 10 to 80%, preferably 20 to 70%, and more preferably 30 to 60%.

The resin (A2) has a mass-average molecular weight of 3,000 to 80,000, preferably 4,000 to 50,000, and more preferably 5,000 to 20,000.

When the resin (A) includes the resin (A2), the content is preferably 5% by mass or more, and more preferably 10% by mass or more, and is preferably 70% by mass or less, and more preferably 65% by mass or less, based on the total amount of resins included in the resist composition.

[Resin (A3)]

The resin (A3) is preferably an alkali-soluble resin. The alkali-soluble resin means a resin which has an acidic group and is soluble in an alkali developing solution. The acidic group is, for example, a carboxy group, a sulfo group, or a phenolic hydroxy group.

Examples of the alkali-soluble resin include an alkali-soluble resin known in the resist field, and examples thereof include a novolak resin, a resin including a polymerization unit derived from hydroxystyrene, a resin including a polymerization unit derived from a (meth)acrylic acid ester, and a polyalkylene glycol. The alkali-soluble resin is preferably a novolak resin. These alkali-soluble resins may be used alone, or two or more alkali-soluble resins may be used in combination.

As described above, the novolak resin means a resin obtained by condensing a phenol compound with aldehyde in the presence of a catalyst. Examples of the phenol compound include phenol; o-, m-, or p-cresol; 2,3-, 2,5-, 3,4-, or 3,5-xylenol; 2,3,5-trimethylphenol; 2-, 3-, or 4-tert-butylphenol; 2-tert-butyl-4- or 5-methylphenol; 2-, 4-, or 5-methylresorcinol; 2-, 3-, or 4-methoxyphenol; 2,3-, 2,5-, or 3,5-dimethoxyphenol; 2-methoxyresorcinol; 4-tert-butylcatechol; 2-, 3-, or 4-ethylphenol; 2,5- or 3,5-diethylphenol; 2,3,5-triethylphenol; 2-naphthol; 1,3-, 1,5-, or 1,7-dihydroxynaphthalene; and a polyhydroxytriphenylmethane-based compound obtained by condensation of xylenol with hydroxybenzaldehyde. These phenol compounds can be used alone, or two or more phenol compounds can be used in combination. Of these, the phenol compound used in the resin (A3) is preferably o-cresol, m-cresol, p-cresol, 2,3-xylenol, 2,5-xylenol, 3,4-xylenol, 3,5-xylenol, 2,3,5-trimethylphenol, 2-tert-butylphenol, 3-tert-butylphenol, 4-tert-butylphenol, 2-tert-butyl-4-methylphenol, or 2-tert-butyl-5-methylphenol.

Examples of the aldehyde include aliphatic aldehydes such as formaldehyde, acetaldehyde, propionaldehyde, n-butylaldehyde, isobutylaldehyde, acrolein, or crotonaldehyde; alicyclic aldehydes such as cyclohexanealdehyde, cyclopentanealdehyde, or furylacrolein; aromatic aldehydes such as furfural, benzaldehyde, o-, m- or p-methylbenzaldehyde, p-ethylbenzaldehyde, 2,4-, 2,5-, 3,4-, or 3,5-dimethylbenzaldehyde, or o-, m-, or p-hydroxybenzaldehyde; and araliphatic aldehydes such as phenylacetaldehyde or cinnamaldehyde. These aldehydes can be used alone, or two or more aldehydes can be used in combination. Of these aldehydes, formaldehyde is preferable since it is industrially available.

Examples of the catalyst to be used for condensation of a phenol compound with aldehyde include inorganic acids such as hydrochloric acid, sulfuric acid, perchloric acid, or phosphoric acid; organic acids such as formic acid, acetic acid, oxalic acid, trichloroacetic acid, or p-toluenesulfonic acid; and divalent metal salts such as zinc acetate, zinc chloride, or magnesium acetate. These catalysts can be used alone, or two or more catalysts can be used in combination. The amount of the catalyst to be used is, for example, 0.01 to 1 mol based on 1 mol of the aldehyde.

A condensation reaction of a phenol compound with aldehyde can be performed according to a conventional method. The condensation reaction can be performed, for example, by mixing a phenol compound with aldehyde, followed by a reaction at a temperature of 60 to 120° C. for about 2 to 30 hours. The condensation reaction may be performed in the presence of a solvent. Examples of the solvent in the condensation reaction include methyl ethyl ketone, methyl isobutyl ketone, acetone and the like. After completion of the reaction, for example, a solvent insoluble in water is added to the reaction mixture and the reaction mixture is washed with water and then concentrated, as needed, thus making it possible to extract a novolak resin.

The resin (A3) has a mass-average molecular weight of 3,000 to 10,000, preferably 4,000 to 9,000, and more preferably 5,000 to 8,000. By adjusting the mass-average molecular weight in this range, it is possible to effectively prevent thinning of a film and remaining of residues after development.

The resin including a polymerization unit derived from hydroxystyrene is typically polyhydroxystyrene, and preferably poly-p-hydroxystyrene. The polyhydroxystyrene can be obtained, for example, by polymerizing monomers mentioned in JP 2010-204634 A.

Examples of the resin including a polymerization unit derived from a (meth)acrylic acid ester include those obtained by polymerizing the following compounds as monomers, which are used alone or in combination, using a conventional method:

compounds having a carboxy group, such as (meth)acrylic acid;

compounds having a hydroxy group, such as 2-hydroxyethyl (meth)acrylate and 2-hydroxypropyl (meth)acrylate; and compounds having a plurality of ether bonds, i.e., polyethylene glycol monomethyl ether (meth)acrylates such as diethylene glycol monomethyl ether (meth)acrylate, triethylene glycol monomethyl ether (meth)acrylate, tetraethylene glycol monomethyl ether (meth)acrylate, pentaethylene glycol monomethyl ether (meth)acrylate, hexaethylene glycol monomethyl ether (meth)acrylate, heptaethylene glycol monomethyl ether (meth)acrylate, octaethylene glycol monomethyl ether (meth)acrylate, and nonaethylene glycol monomethyl ether (meth)acrylate.

The above monomers may be used in combination with (meth)acrylic acid alkyl esters such as methyl (meth)acrylate, ethyl (meth)acrylate, and tert-butyl (meth)acrylate; (meth)acrylic acid cycloalkyl esters such as cyclopentyl (meth)acrylate and cyclohexyl (meth)acrylate; polycyclic (meth)acrylic acid esters such as adamantyl (meth)acrylate; ethylene glycol monomethyl ether (meth)acrylate, ethylene glycol monoethyl ether (meth)acrylate, ethylene glycol monopropyl ether (meth)acrylate, ethylene glycol monobutyl ether (meth)acrylate, ethylene glycol monoalkyl ether (meth)acrylates and the like.

When the resin (A) includes the resin (A3), the content is preferably 10% by mass or more, and more preferably 20% by mass or more, and is preferably 70% by mass or less, and more preferably 65% by mass or less, based on the total amount of resins included in the resist composition.

The content of the resin (A) in the resist composition is preferably 80% by mass or more and 99% by mass or less, and more preferably 90 to 99% by mass, based on the solid content of the resist composition. The solid content of the resist composition and the content of the resin based on the resist composition can be measured by known analytical means such as liquid chromatography or gas chromatography.

<Acid Generator (B)>

Either nonionic or ionic acid generator may be used as the acid generator (B). Examples of the nonionic acid generator include sulfonate esters (e.g., 2-nitrobenzyl ester, aromatic sulfonate, oxime sulfonate, N-sulfonyloxyimide, sulfonyloxy ketone, diazonaphthoquinone 4-sulfonate), sulfones (e.g., disulfone, ketosulfone, sulfonyldiazomethane) and the like. Typical examples of the ionic acid generator include onium salts containing an onium cation (e.g., diazonium salt, phosphonium salt, sulfonium salt, iodonium salt). Examples of the anion of the onium salt include sulfonic acid anion, sulfonylimide anion, sulfonylmethide anion and the like.

Specific examples of the acid generator (B) include compounds generating an acid upon exposure to radiation mentioned in JP 63-26653 A, JP 55-164824 A, JP 62-69263 A, JP 63-146038 A, JP 63-163452 A, JP 62-153853 A, JP 63-146029 A, U.S. Pat. Nos. 3,779,778, 3,849,137, DE Patent No. 3914407 and EP Patent No. 126,712. Compounds produced by a known method may also be used. Two or more acid generators (B) may also be used in combination.

The nonionic acid generator is preferably a compound having a group represented by formula (B1) (* represents a bond):

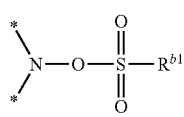
(B1)

wherein, in formula (B1), $R^{b1}$ represents a hydrocarbon group having 1 to 18 carbon atoms which may have a fluorine atom, and a methylene group included in the hydrocarbon group may be substituted with an oxygen atom or a carbonyl group.

A nitrogen atom may have a double bond.

Examples of the hydrocarbon group having 1 to 18 carbon atoms include a chain hydrocarbon group, an alicyclic hydrocarbon group, an aromatic hydrocarbon group, and a group obtained by combining these groups.

The chain hydrocarbon group is preferably an alkyl group, and examples thereof include a methyl group, an ethyl group, a propyl group, a butyl group, a pentyl group, a hexyl group, a heptyl group, an octyl group, a nonyl group, and a decyl group.

Examples of the alicyclic hydrocarbon group include a cyclopropyl group, a cyclobutyl group, a cyclopentyl group, a cyclohexyl group, a cycloheptyl group, a cyclooctyl group, and an adamantyl group.

The aromatic hydrocarbon group is preferably an aryl group having 6 to 18 carbon atoms, and examples thereof include aryl groups such as a phenyl group, a naphthyl group, an anthryl group, a biphenyl group, and a phenanthryl group.

Examples of the group combined include a group obtained by combining a chain hydrocarbon group and an alicyclic hydrocarbon group (e.g., a cycloalkylalkyl group), an aralkyl group such as a benzyl group, an aromatic hydrocarbon group having an alkyl group (a p-methylphenyl group, a p-tert-butylphenyl group, a tolyl group, a xylyl group, a cumenyl group, a mesityl group, a 2,6-diethylphenyl group, a 2-methyl-6-ethylphenyl group, etc.), an aromatic hydrocarbon group having an alicyclic hydrocarbon group (a p-cyclohexylphenyl group, a p-adamantylphenyl group, etc.), an aryl-cycloalkyl group such as a phenylcyclohexyl group and the like.

The hydrocarbon group represented by $R^{b1}$ is preferably an alkyl group having 1 to 10 carbon atoms or an aromatic hydrocarbon group having 6 to 10 carbon atoms, more preferably an alkyl group having 1 to 8 carbon atoms, and still more preferably an alkyl group having 1 to 4 carbon atoms.

When $R^{b1}$ is an alicyclic hydrocarbon group or an alicyclic hydrocarbon group having an alkyl group, examples of the group in which a methylene group included in the alicyclic hydrocarbon group in $R^{b1}$ is substituted with an oxygen atom or a carbonyl group include groups represented by formula (Y1) to formula (Y12). The group is preferably groups represented by formula (Y7) to formula (Y9), and more preferably a group represented by formula (Y9).

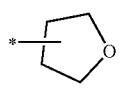
(Y1)

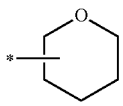
(Y2)

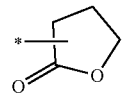
(Y3)

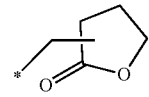
(Y4)

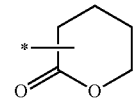
(Y5)

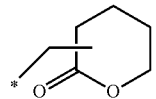
(Y6)

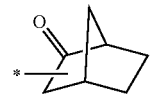
(Y7)

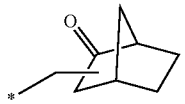
(Y8)

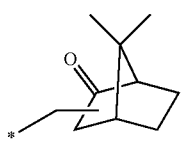
(Y9)

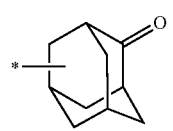
(Y10)

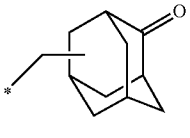
(Y11)

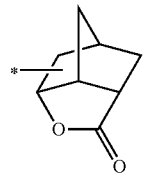
(Y12)

Examples of the hydrocarbon group having a fluorine atom include fluoroalkyl groups such as a fluoromethyl group, a fluoroethyl group, a fluoropropyl group, a fluorobutyl group, a fluoropentyl group, a fluorohexyl group, a fluoroheptyl group, a fluorooctyl group, a fluorononyl group, and a fluorodecyl group; fluorocycloalkyl groups such as a fluorocyclopropyl group, a fluorocyclobutyl group, a fluorocyclopentyl group, a fluorocyclohexyl group, fluorocycloheptyl group, a fluorocyclooctyl group, and a fluoroadamantyl group; and fluoroaryl groups such as a fluorophenyl group, a fluoronaphthyl group, and a fluoroanthryl group.

The hydrocarbon group having a fluorine atom is preferably an alkyl group having 1 to 10 carbon atoms which has a fluorine atom, or an aromatic hydrocarbon group having 6 to 10 carbon atoms which has a fluorine atom, more preferably a perfluoroalkyl group having 1 to 8 carbon atoms, and still more preferably a perfluoroalkyl group having 1 to 4 carbon atoms.

Examples of the compound having a group represented by formula (B1) include compounds represented by formula (b1) to formula (b3). The compound is preferably a compound represented by formula (b1) or formula (b2), and more preferably a compound represented by formula (b1):

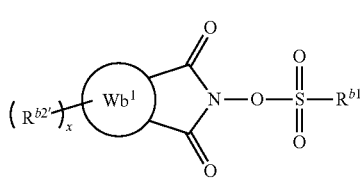
(b1)

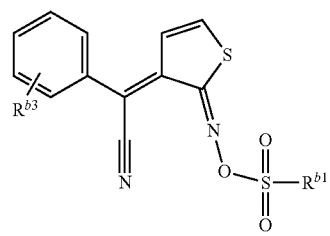
(b2)

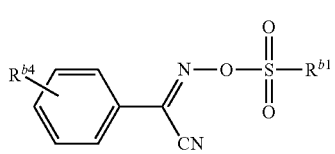
(b3)

wherein, in formula (b1) to formula (b3), $R^{b1}$ is the same as defined above, $R^{b2'}$, $R^{b3}$, and $R^{b4}$ each independently represent a hydrogen atom, an alkyl group having 1 to 8 carbon atoms, or an alkoxy group having 1 to 8 carbon atoms, ring $W^{b1}$ represents an aromatic hydrocarbon ring having 6 to 14 carbon atoms or an aromatic heterocyclic ring having 6 to 14 carbon atoms, and x represents an integer of 0 to 2, and when x is 2, a plurality of $R^{b2'}$ may be the same or different.

Examples of the alkyl group include a methyl group, an ethyl group, a propyl group, a butyl group, and a pentyl group, and a methyl group is preferable.

Examples of the alkoxy group include a methoxy group, an ethoxy group, a propoxy group, a butoxy group, and a pentyloxy group, and a methoxy group is preferable.

Examples of the aromatic hydrocarbon ring include a benzene ring, a naphthalene ring, and an anthracene ring.

Examples of the aromatic heterocyclic ring include a ring having 6 to 14 ring-constituting atoms, and the following rings are preferable.

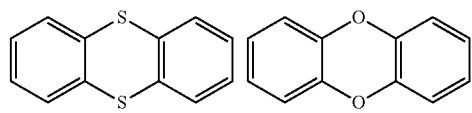

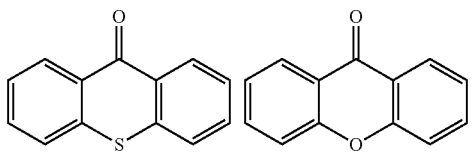

Examples of the substituent which may be possessed by the ring $W^{b1}$ include an alkyl group having 1 to 5 carbon atoms and the like.

The ring $W^{b1}$ is preferably a naphthalene ring.

The compound represented by formula (b1) is preferably a compound represented by any one of formula (b4) to formula (b7), and more preferably, a compound represented by formula (b4):

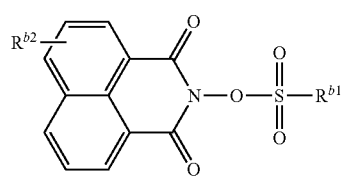
(b4)

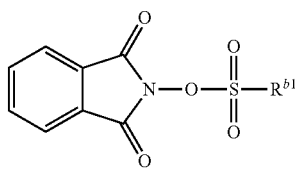
(b5)

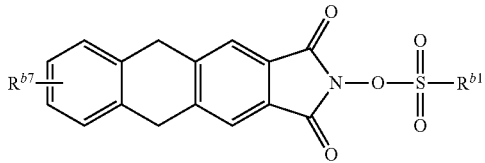
(b6)

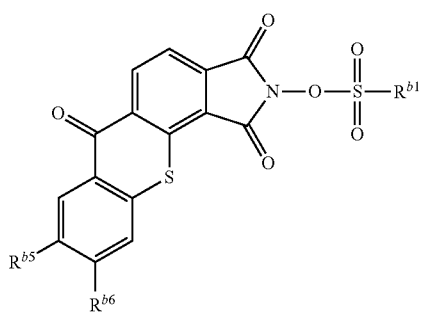
(b7)

wherein, in formula (b4) to formula (b7), $R^{b1}$ is the same as defined above, and $R^{b2}$, $R^{b5}$, $R^{b6}$, and $R^{b7}$ each independently represent a hydrogen atom or an alkyl group having 1 to 8 carbon atoms.

Examples of the compound represented by formula (b1) include compounds represented by formula (b1-1) to formula (b1-14) and the like. A compound represented by formula (b1-6) or formula (b1-7) is preferable.

(b1-1) 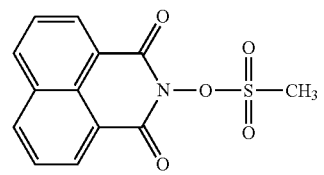
(b1-2) 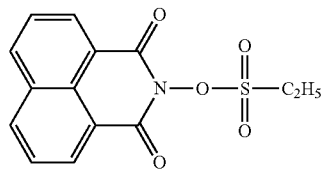
(b1-3) 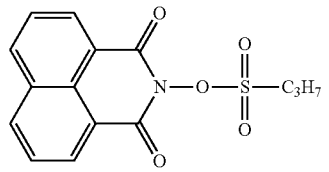
(b1-4) 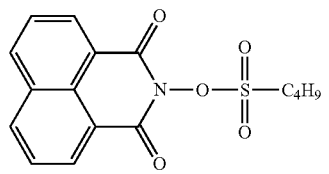
(b1-5) 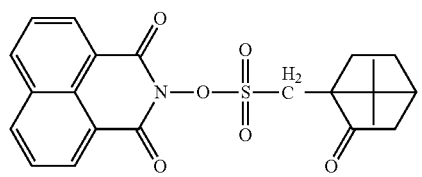
(b1-6) 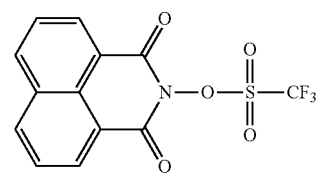
(b1-7) 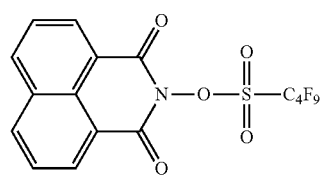
(b1-8) 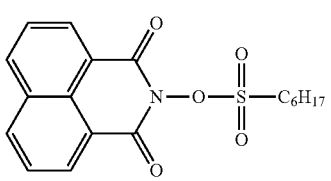
(b1-9) 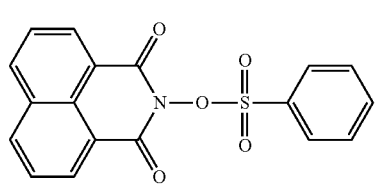
(b1-10) 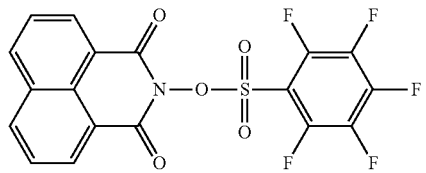
(b1-11) 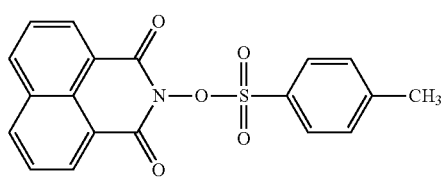
(b1-12) 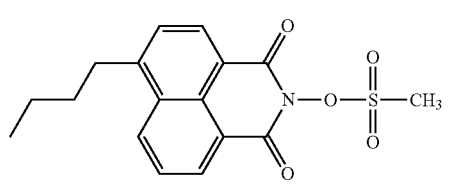
(b1-13) 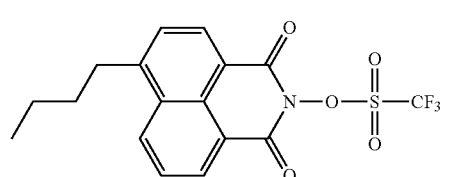
(b1-14) 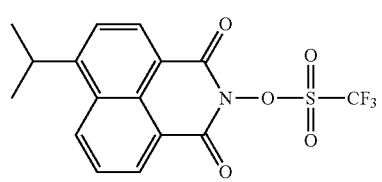
Examples of the compound represented by formula (b2) include compounds represented by the following formulas.
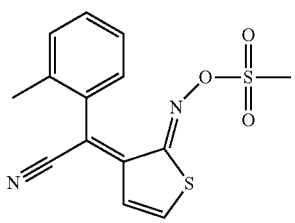
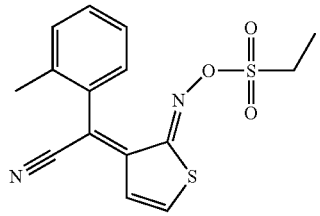

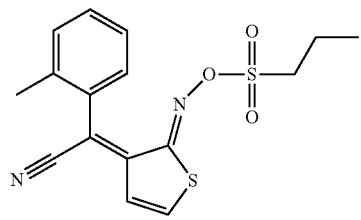
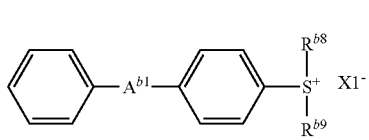

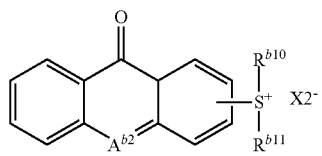

wherein, in formula (b8) and formula (b9), $A^{b1}$ and $A^{b2}$ each independently represent an oxygen atom or a sulfur atom, $R^{b8}$, $R^{b9}$, $R^{b10}$ and $R^{b11}$ each independently represent an alkyl group having 1 to 10 carbon atoms or an aromatic hydrocarbon group having 6 to 12 carbon atoms, and $X1^-$ and $X2^-$ represent an organic anion.

Examples of the alkyl group include a methyl group, an ethyl group, a propyl group, a butyl group, a pentyl group, a hexyl group, a heptyl group, and an octyl group.

Examples of the aromatic hydrocarbon group include aryl groups such as a phenyl group, a naphthyl group, an anthryl group, a p-methylphenyl group, a p-tert-butylphenyl group, a p-adamantylphenyl group, a tolyl group, a xylyl group, a cumenyl group, a mesityl group, a biphenyl group, a phenanthryl group, a 2,6-diethylphenyl group, and 2-methyl-6-ethylphenyl group.

$R^{b8}$, $R^{b9}$, $R^{b10}$, and $R^{b11}$ are each preferably an aromatic compound having 6 to 12 carbon atoms, and more preferably a phenyl group.

Examples of the organic anion represented by $X1^-$ and $X2^-$ include a sulfonic acid anion, a bis(alkylsulfonyl)amide anion, and a tris(alkylsulfonyl)methide anion, and a sulfonic acid anion is preferable, and a sulfonic acid anion represented by formula (b10) is more preferable:

Examples of the compound represented by formula (b3) include compounds represented by the following formulas and the like.

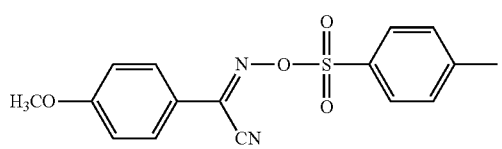
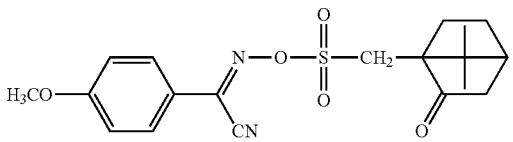
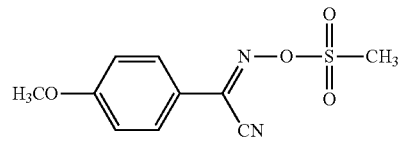

The ionic acid generator is preferably a compound represented by formula (b8) or formula (b9):

(b10)

wherein, in formula (b10), $R^{b12}$ represents a hydrocarbon group having 1 to 18 carbon atoms which may have a fluorine atom, and a methylene group included in the hydrocarbon group may be substituted with an oxygen atom or a carbonyl group.

Examples of the $R^{b12}$ include the same groups as for $R^{b1}$ in formula (B1).

Examples of the compound represented by formula (b8) include the following compounds and the like.

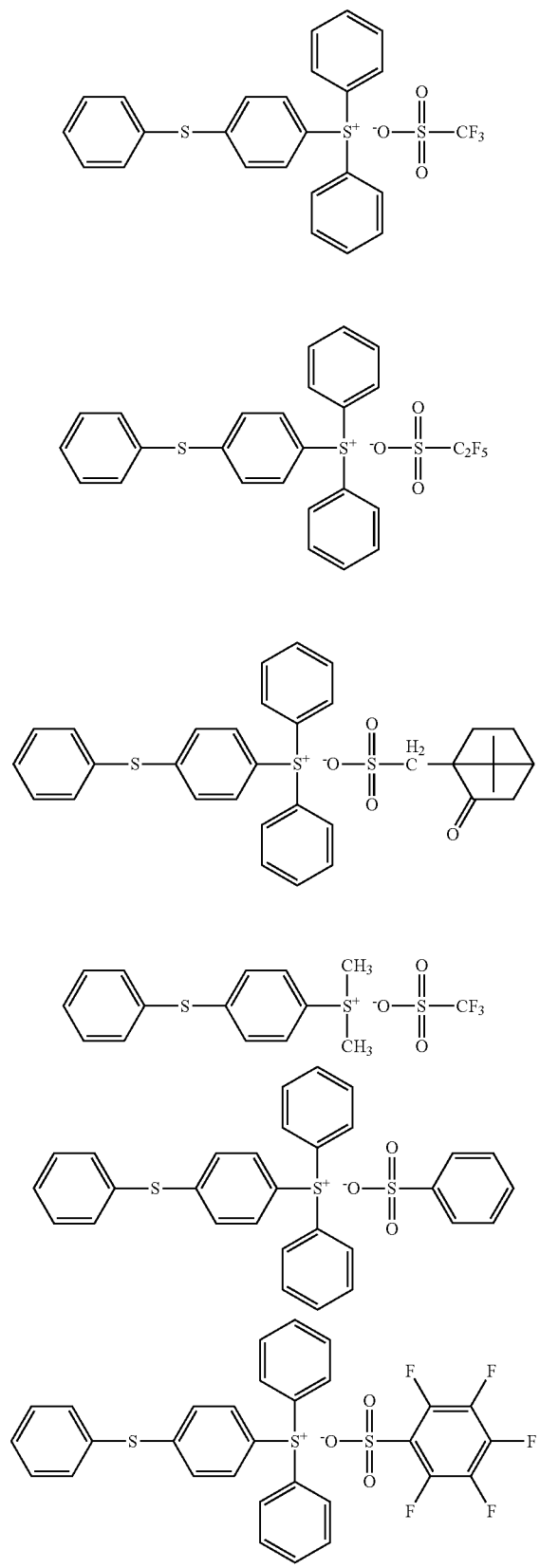
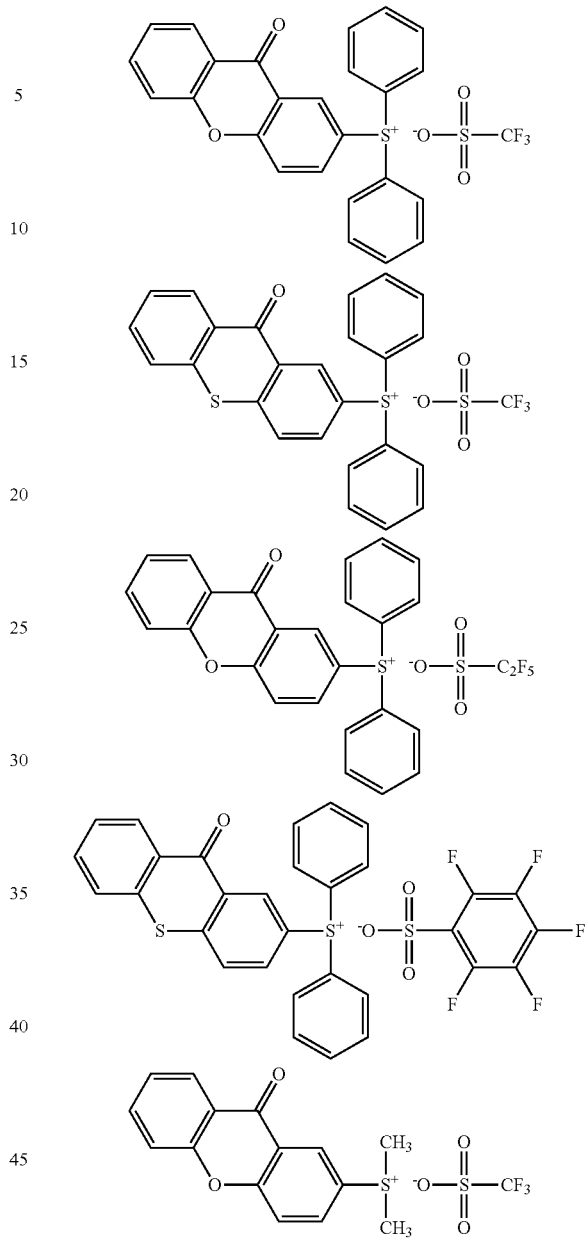

Examples of the compound represented by formula (b9) include the following compounds and the like.

In the resist composition of the present invention, the content of the acid generator is preferably 0.5 part by mass or more and 30 parts by mass or less, more preferably 1 part by mass or more and 20 parts by mass or less, and still more preferably 1 part by mass or more and 5 parts by mass or less, based on 100 parts by mass of the resin (A). The resist composition of the present invention may include the acid generator (B) alone, or a plurality of the acid generators.

<Quencher (C)>

The quencher (C) is a compound having an effect of trapping an acid generated from the acid generator upon exposure to radiation. Examples of the quencher (C) include a basic nitrogen-containing organic compound.

Examples of the basic nitrogen-containing organic compound include amine and an ammonium salt. Examples of the amine include an aliphatic amine and an aromatic amine; a primary amine, a secondary amine, and a tertiary amine.

Examples of the amine include a compound represented by formula (C1) or formula (C2):

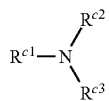
(C1)

wherein, in formula (C1), $R^{c1}$, $R^{c2}$ and $R^{c3}$ each independently represent a hydrogen atom, an alkyl group having 1 to 6 carbon atoms, an alicyclic hydrocarbon group having 5 to 10 carbon atoms, or an aromatic hydrocarbon group having 6 to 10 carbon atoms, a hydrogen atom included in the alkyl group and the alicyclic hydrocarbon group may be substituted with a hydroxy group, an amino group, or an alkoxy group having 1 to 6 carbon atoms, and a hydrogen atom included in the aromatic hydrocarbon group may be substituted with an alkyl group having 1 to 6 carbon atoms, an alkoxy group having 1 to 6 carbon atoms, or an alicyclic hydrocarbon group having 5 to 10 carbon atoms.

Examples of the alkyl group, the alicyclic hydrocarbon group, the aromatic hydrocarbon group, the alkoxy group, and the alkanediyl group in formula (C1) include those which are the same as mentioned above.

Examples of the compound represented by formula (C1) include 1-naphthylamine, 2-naphthylamine, aniline, diisopropylaniline, 2-, 3-, or 4-methylaniline, 4-nitroaniline, N-methylaniline, N,N-dimethylaniline, diphenylamine, hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, dibutylmethylamine, methyldipentylamine, dihexylmethylamine, dicyclohexylmethylamine, diheptylmethylamine, methyldioctylamine, methyldinonylamine, didecylmethylamine, ethyldibutylamine, ethyldipentylamine, ethyldihexylamine, ethyldiheptylamine, ethyldioctylamine, ethyldinonylamine, ethyldidecylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenylmethane and the like, preferably diisopropylaniline, and particularly preferably 2,6-diisopropylaniline:

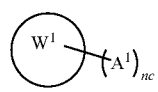
(C2)

wherein, in formula (C2),
ring $W^1$ represents a heterocyclic ring having a nitrogen atom as a ring-constituting atom, or a benzene ring having a substituted or unsubstituted amino group, and the heterocyclic ring and the benzene ring may have at least one selected from the group consisting of a hydroxy group and an alkyl group having 1 to 4 carbon atoms,
$A^1$ represents a phenyl group or a naphthyl group, and
nc represents 2 or 3 and a plurality of $A^1$ may be the same or different.

The substituted or unsubstituted amino group is represented by $-N(R^4)(R^5)$, and $R^4$ and $R^5$ each independently represent a hydrogen atom, a chain hydrocarbon group having 1 to 10 carbon atoms, an alicyclic hydrocarbon group having 3 to 10 carbon atoms, or an aromatic hydrocarbon group having 6 to 14 carbon atoms.

Examples of the chain hydrocarbon group include alkyl groups such as a methyl group, an ethyl group, a propyl group, a butyl group, a pentyl group, a hexyl group, a heptyl group, and an octyl group.

Examples of the alicyclic hydrocarbon group include the same groups as for $R^{a1}$ to $R^{a3}$ in formula (1). Examples of the aromatic hydrocarbon group include the same groups as for $R^{a1'}$ to $R^{a3'}$ in formula (2).

The heterocyclic ring having a nitrogen atom as a ring-constituting atom may be either an aromatic ring or a non-aromatic ring, and may have other hetero atoms (e.g., an oxygen atom, a sulfur atom), together with a nitrogen atom. The heterocyclic ring has, for example, 1 to 3 nitrogen atoms. Examples of the heterocyclic ring include a ring represented by any one of formula (Y13) to formula (Y28). One of hydrogen atoms included in the ring is removed to form a bond to $A^1$.

(Y13)

(Y14)

(Y15)

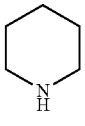
(Y16)

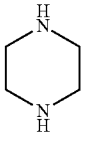
(Y17)

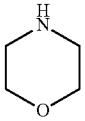
(Y18)

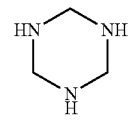
(Y19)

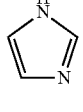
(Y20)

(Y21)

(Y22) 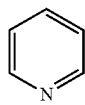

(Y23) 

(Y24) 

(Y25) 

(Y26) 

(Y27) 

(Y28) 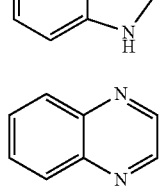

The ring $W^1$ is preferably a heterocyclic ring having a nitrogen atom as a ring-constituting atom, more preferably a 5- or 6-membered ring aromatic heterocyclic ring having a nitrogen atom as a ring-constituting atom, and still more preferably a ring represented by any one of formula (Y20) to formula (Y25).

Examples of the compound represented by formula (C2) include a compound represented by any one of formula (C2-1) to formula (C2-11). A compound represented by any one of formula (C2-2) to formula (C2-8) is preferable.

(C2-1) 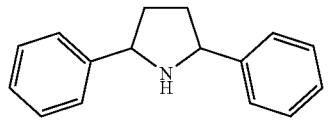

(C2-2) 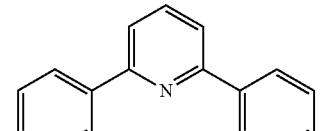

(C2-3) 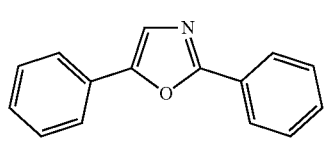

(C2-4) 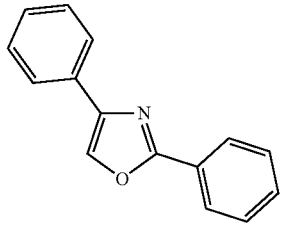

(C2-5) 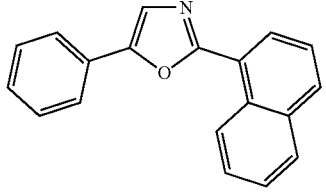

(C2-6) 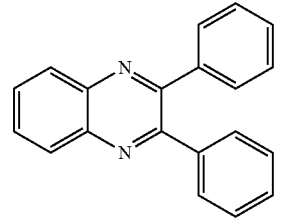

(C2-7) 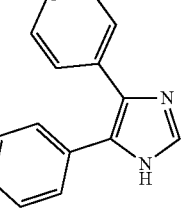

(C2-8) 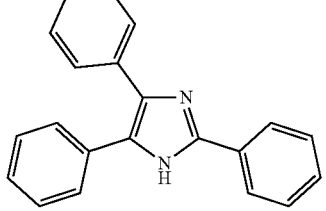

(C2-9) 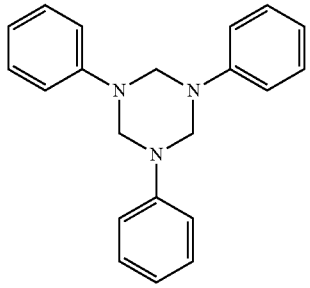

(C2-10)

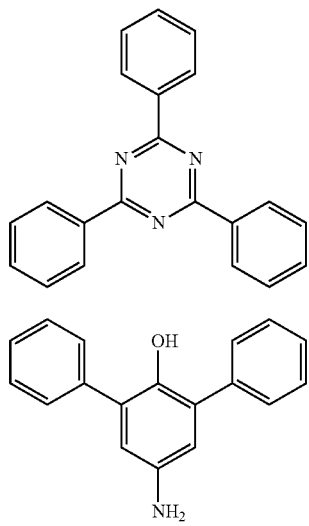

(C2-11)

The content of the quencher (C) in the solid component of the resist composition is preferably 0.0001 to 5% by mass, more preferably 0.0001 to 4% by mass, still more preferably 0.001 to 3% by mass, yet more preferably 0.01 to 1.0% by mass, and particularly preferably 0.1 to 0.7% by mass.

<Solvent (D)>

The content of the solvent (D) in the resist composition is usually 45% by mass or more and 99.9% by mass or less, preferably 50% by mass or more and 99% by mass or less, and more preferably 55% by mass or more and 90% by mass or less. The content of the solvent (D) can be measured, for example, by known analytical means such as liquid chromatography or gas chromatography.

Examples of the solvent (D) include glycol ether esters such as ethyl cellosolve acetate, methyl cellosolve acetate, and propylene glycol monomethyl ether acetate; glycol ethers such as propylene glycol monomethyl ether; esters such as ethyl lactate, butyl acetate, amyl acetate, and ethyl pyruvate; ketones such as acetone, methyl isobutyl ketone, 2-heptanone, and cyclohexanone; and cyclic esters such as γ-butyrolactone. These solvent (D) may be used alone, or two or more solvents may be used.

<Adhesion Improver (E)>

The adhesion improver (E) is not particularly limited as long as it is possible to prevent corrosion of metal used in a substrate, wiring or the like and/or to improve adhesion. A rust-preventive effect is exhibited by preventing corrosion of the metal. In addition to the effect, it is possible to improve the adhesion between the substrate or the metal and the resist composition.

Examples of the adhesion improver (E) include a sulfur-containing compound, an aromatic hydroxy compound, a benzotriazole-based compound, a triazine-based compound, and a silicon-containing compound. These compounds can be used alone, or two or more compounds can be used in combination.

The sulfur-containing compound may be, for example, a compound having a sulfide bond and/or a mercapto group. The sulfur-containing compound may be either a chain compound or a compound having a cyclic structure.

Examples of the chain compound include dithiodiglycerol [S(CH$_2$CH(OH)CH$_2$ (OH))$_2$], bis(2,3-dihydroxypropylthio) ethylene [CH$_2$CH$_2$ (SCH$_2$CH(OH) CH$_2$ (OH))$_2$], sodium 3-(2,3-dihydroxypropylthio)-2-methyl-propylsulfonate [CH$_2$ (OH)CH(OH)CH$_2$SCH$_2$CH(CH$_3$)CH$_2$SO$_3$Na], 1-thioglycerol [HSCH$_2$CH(OH)CH$_2$ (OH)], sodium 3-mercapto-1-propanesulfonate [HSCH$_2$CH$_2$CH$_2$SO$_3$Na], 2-mercaptoethanol [HSCH$_2$CH$_2$ (OH)], thioglycolic acid [HSCH$_2$CO$_2$H], 3-mercapto-1-propanol [HSCH$_2$CH$_2$CH$_2$] and the like.

The sulfur-containing compound is preferably a compound having a sulfide bond and a mercapto group, and more preferably a heterocyclic compound having a sulfide bond and a mercapto group. The heterocyclic compound is more preferably a heterocyclic compound having a sulfide bond in ring constitution. In the sulfur-containing compound, the number of the sulfide bond and the mercapto group is not particularly limited and may be 1 or more.

The heterocyclic compound having a sulfide bond in ring constitution may be either monocyclic or polycyclic, or may be either saturated or unsaturated cyclic. It is preferable that the heterocyclic compound having a sulfide bond in ring constitution further has a hetero atom other than a sulfur atom. Examples of the hetero atom include an oxygen atom and a nitrogen atom, and a nitrogen atom is preferable.

The heterocyclic compound having a sulfide bond in ring constitution is preferably a heterocyclic compound having 2 to 12 carbon atoms, and more preferably a heterocyclic compound having 2 to 6 carbon atoms. The heterocyclic compound is preferably monocyclic. The heterocyclic compound having a sulfide bond in ring constitution is preferably unsaturated. The heterocyclic compound having a sulfide bond in ring constitution is preferably unsaturated and monocyclic.

Examples of the heterocyclic compound having a sulfide bond in ring constitution include the following heterocyclic compounds.

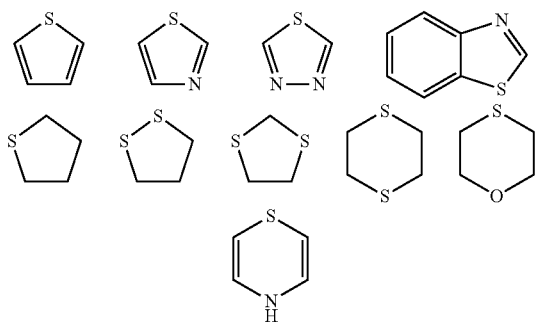

The sulfur-containing compound may be a polymer. This polymer preferably has a structure having a sulfide bond and a mercapto group in a side chain. A structure having a sulfide bond and a mercapto group (hereinafter sometimes referred to as unit (1)) and a main chain are preferably bonded together with a linking group such as an amide bond, an ether bond, a thio-ether bond, and an ester bond.

The polymer may be either a homopolymer or a copolymer.

When the polymer is a copolymer, the copolymer may include the above structural unit having an acid-labile group and the above structural unit having no acid-labile group.

The weight-average molecular weight of the homopolymer and the copolymer is usually 3,000 or more, and preferably 5,000 or more, and is usually 100,000 or less, and preferably 50,000 or less.

When the sulfur-containing compound is a polymer, the content of the structural unit having a sulfide bond and a mercapto group is usually 0.1 to 50 mol %, preferably 0.5 to 30 mol %, and more preferably 1 to 20 mol %, based on all structural units of the polymer of the sulfur-containing compound.

The sulfur-containing compound is preferably, for example, a compound represented by formula (IA) or a polymer having a structural unit represented by formula (IB):

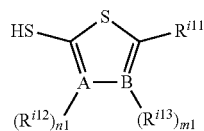

(IA)

wherein, in formula (IA), $R^{i11}$ represents a hydrogen atom, a chain hydrocarbon group having 1 to 10 carbon atoms, an aromatic hydrocarbon group having 6 to 14 carbon atoms, an alicyclic hydrocarbon group having 3 to 18 carbon atoms, a group represented by $—SR^{11}$, or a group represented by $—NR^{12}R^{13}$, $R^{11}$, $R^{12}$ and $R^{13}$ each independently represent a hydrogen atom, a chain hydrocarbon group having 1 to 10 carbon atoms, an alicyclic hydrocarbon group having 3 to 10 carbon atoms, an aromatic hydrocarbon group having 6 to 14 carbon atoms, or an alkylcarbonyl group having 1 to 12 carbon atoms, and a hydrogen atom of the chain hydrocarbon group, the alicyclic hydrocarbon group, the aromatic hydrocarbon group, and the alkylcarbonyl group may be substituted with a hydroxy group, $R^{i12}$ and $R^{i13}$ each independently represent a hydrogen atom, a chain hydrocarbon group having 1 to 10 carbon atoms, an aromatic hydrocarbon group having 6 to 14 carbon atoms, or an alicyclic hydrocarbon group having 3 to 18 carbon atoms, A and B each independently represent a nitrogen atom or a carbon atom, and n1 and m1 each independently represent 0 or 1, when A is a nitrogen atom, n1 represents 0, when A is a carbon atom, n1 represents 1, when B is a nitrogen atom, m1 represents 0, and when B is a carbon atom, m1 represents 1.

Examples of the chain hydrocarbon group include alkyl groups such as a methyl group, an ethyl group, a propyl group, a butyl group, a pentyl group, a hexyl group, a heptyl group, and an octyl group.

Examples of the aromatic hydrocarbon group include aryl groups such as a phenyl group, a naphthyl group, an anthryl group, a p-methylphenyl group, a p-tert-butylphenyl group, a p-adamantylphenyl group, a tolyl group, a xylyl group, a cumenyl group, a mesityl group, a biphenyl group, a phenanthryl group, a 2,6-diethylphenyl group, and 2-methyl-6-ethylphenyl group.

Examples of the alicyclic hydrocarbon group include monocyclic alicyclic hydrocarbon groups, i.e., cycloalkyl groups such as a cyclopentyl group, a cyclohexyl group, a cycloheptyl group, and a cyclooctyl group; and polycyclic alicyclic hydrocarbon groups such as a decahydronaphthyl group, an adamantyl group, and a norbornyl group.

$R^{11}$ is preferably a chain hydrocarbon group or an alkylcarbonyl group, and it is preferable that $R^{12}$ and $R^{13}$ each independently represent a hydrogen atom, a chain hydrocarbon group, an aromatic hydrocarbon group, and an alkylcarbonyl group.

Examples of the alkylcarbonyl group include an acetyl group, a propionyl group, a butyryl group, a valeryl group, a hexylcarbonyl group, a heptylcarbonyl group, an octylcarbonyl group, a decylcarbonyl group and a dodecylcarbonyl group, and a benzoyl group.

$R^{i11}$ is more preferably a hydrogen atom or a mercapto group.

Preferably, $R^{i12}$ and $R^{i13}$ each independently represent a hydrogen atom or an alkyl group having 1 to 4 carbon atoms, and more preferably a hydrogen atom.

At least one of A and B is preferably a nitrogen atom, and both of them are more preferably a nitrogen atom:

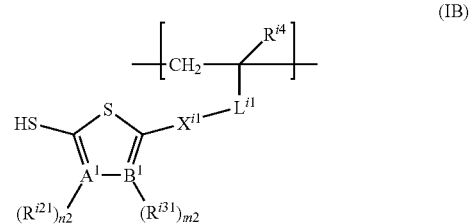

(IB)

wherein, in formula (IB), $R^{i21}$ and $R^{i31}$ each independently represent a hydrogen atom, a chain hydrocarbon group having 1 to 10 carbon atoms, an aromatic hydrocarbon group having 6 to 14 carbon atoms, or an alicyclic hydrocarbon group having 3 to 18 carbon atoms, $A^1$ and $B^1$ each independently represent a nitrogen atom or a carbon atom, n2 and m2 each independently represent 0 or 1, when $A^1$ is a nitrogen atom, n2 represents 0, when $A^1$ is a carbon atom, n2 represents 1, when $B^1$ is a nitrogen atom, m2 represents 0, and when $B^1$ is a carbon atom, m2 represents 1, $R^{i4}$ represents a hydrogen atom or a methyl group, $X^{i1}$ represents a sulfur atom or an NH group, and $L^{i1}$ represents a divalent hydrocarbon group having 1 to 20 carbon atoms, and a methylene group included in the hydrocarbon group may be substituted with an oxygen atom or a carbonyl group.

Examples of the chain hydrocarbon group of $R^{i21}$ and $R^{i31}$ include alkyl groups such as a methyl group, an ethyl group, a propyl group, a butyl group, a pentyl group, a hexyl group, a heptyl group, and an octyl group, and preferably an alkyl group having 1 to 4 carbon atoms.

Examples of the aromatic hydrocarbon group of $R^{i21}$ and $R^{i31}$ include aryl groups such as a phenyl group, a naphthyl group, an anthryl group, a p-methylphenyl group, a p-tert-butylphenyl group, a p-adamantylphenyl group, a tolyl group, a xylyl group, a cumenyl group, a mesityl group, a biphenyl group, a phenanthryl group, a 2,6-diethylphenyl group, and 2-methyl-6-ethylphenyl group, and preferably an aryl group having 6 to 10 carbon atoms.

Examples of the alicyclic hydrocarbon group of $R^{i21}$ and $R^{i31}$ include monocyclic alicyclic hydrocarbon groups, i.e., cycloalkyl groups such as a cyclopentyl group, a cyclohexyl group, a cycloheptyl group, and a cyclooctyl group; and polycyclic alicyclic hydrocarbon groups such as a decahydronaphthyl group, an adamantyl group, and a norbornyl group, and preferably an alicyclic hydrocarbon group having 5 to 10 carbon atoms.

Preferably, $R^{i21}$ and $R^{i31}$ each independently represent a hydrogen atom or an alkyl group having 1 to 4 carbon atoms.

Examples of the divalent hydrocarbon group represented by $L^{i1}$ include alkanediyl groups such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group, an ethane-1,1-diyl group, a propane-1,1-diyl group, a propane-1,2-diyl group, a propane-2,2-diyl group, a pentane-2,4-diyl group, a 2-methylpropane-1,3-diyl group, a 2-methylpropane-1,2-diyl group, a pentane-1,4-diyl group, and a 2-methylbutane-1,4-diyl group;

monocyclic divalent alicyclic saturated hydrocarbon groups which are cycloalkanediyl groups such as a cyclobutane-1,3-diyl group, a cyclopentane-1,3-diyl group, a cyclohexane-1,4-diyl group, and a cyclooctane-1,5-diyl group;

polycyclic divalent alicyclic saturated hydrocarbon groups such as a norbornane-1,4-diyl group, a norbornane-2,5-diyl group, an adamantane-1,5-diyl group, and an adamantane-2,6-diyl group; and arylene groups such as a phenylene group, a tolylene group, and a naphthylene group.

$L^{i1}$ is preferably a group obtained by combining an alkanediyl group having 2 to 14 carbon atoms having an ester bond or an arylene group having 6 to 10 carbon atoms with an alkanediyl group having 1 to 11 carbon atoms.

The structural unit represented by formula (IB) is preferably a structural unit represented by formula (IB-1) or a structural unit represented by formula (IB-2):

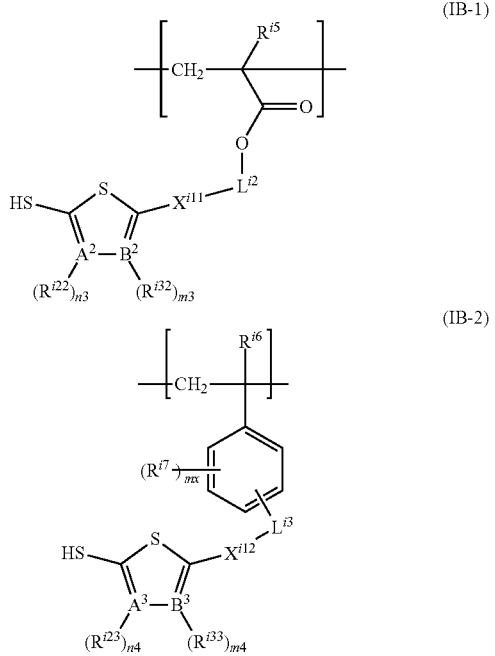

wherein, in formula (IB-1), $R^{i22}$ and $R^{i32}$ each independently represent a hydrogen atom, a chain hydrocarbon group having 1 to 10 carbon atoms, an aromatic hydrocarbon group having 6 to 14 carbon atoms, or an alicyclic hydrocarbon group having 3 to 18 carbon atoms, $A^2$ and $B^2$ each independently represent a nitrogen atom or a carbon atom, n3 and m3 each independently represent 0 or 1, when $A^2$ is a nitrogen atom, n3 represents 0, when $A^2$ is a carbon atom, n3 represents 1, when $B^2$ is a nitrogen atom, m3 represents 0, and when $B^2$ is a carbon atom, m3 represents 1, $X^{i11}$ represents a sulfur atom or an NH group, and $L^{i2}$ represents a divalent hydrocarbon group having 1 to 18 carbon atoms, and a methylene group included in the hydrocarbon group may be substituted with an oxygen atom or a carbonyl group, $R^{i5}$ represents a hydrogen atom or a methyl group, and wherein, in formula (IB-2), $R^{i23}$ and $R^{i33}$ each independently represent a hydrogen atom, a chain hydrocarbon group having 1 to 10 carbon atoms, an aromatic hydrocarbon group having 6 to 14 carbon atoms, or an alicyclic hydrocarbon group having 3 to 18 carbon atoms, $A^3$ and $B^3$ each independently represent a nitrogen atom or a carbon atom, n4 and m4 each independently represent 0 or 1, when $A^3$ is a nitrogen atom, n4 represents 0, when $A^3$ is a carbon atom, n4 represents 1, when $B^3$ is a nitrogen atom, m4 represents 0, and when $B^3$ is a carbon atom, m4 represents 1, $X^{i12}$ represents a sulfur atom or an NH group, $L^{i3}$ represents a divalent hydrocarbon group having 1 to 14 carbon atoms, and a methylene group included in the hydrocarbon group may be substituted with an oxygen atom or a carbonyl group, $R^{i7}$ represents an alkyl group having 1 to 6 carbon atoms or an alkoxy group having 1 to 6 carbon atoms, $R^{i6}$ represents a hydrogen atom or a methyl group, and mx represents an integer of 0 to 4.

Examples of the chain hydrocarbon group having 1 to 10 carbon atoms represented by $R^{i22}$, $R^{i32}$, $R^{i23}$, and $R^{i33}$ include those which are the same as chain hydrocarbon groups having 1 to 10 carbon atoms represented by $R^{i21}$ and $R^{i31}$ Examples of the aromatic hydrocarbon group having 6 to 14 carbon atoms represented by $R^{i22}$, $R^{i32}$, $R^{i23}$, and $R^{i33}$ include those which are the same as aromatic hydrocarbon groups having 6 to 14 carbon atoms represented by $R^{i21}$ and $R^{i31}$.

Examples of the alicyclic hydrocarbon group having 3 to 18 carbon atoms represented by $R^{i22}$, $R^{i32}$, $R^{i23}$, and $R^{i33}$ include those which are the same as alicyclic hydrocarbon groups having 3 to 18 carbon atoms represented by $R^{i21}$ and $R^{i31}$.

Examples of the divalent hydrocarbon group having 1 to 18 carbon atoms represented by $L^{i2}$ include alkanediyl groups such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group, an ethane-1,1-diyl group, a propane-1,1-diyl group, a propane-1,2-diyl group, a propane-2,2-diyl group, a pentane-2,4-diyl group, a 2-methylpropane-1,3-diyl group, a 2-methylpropane-1,2-diyl group, a pentane-1,4-diyl group, and a 2-methylbutane-1,4-diyl group;

monocyclic divalent alicyclic saturated hydrocarbon groups which are cycloalkanediyl groups such as a cyclobutane-1,3-diyl group, a cyclopentane-1,3-diyl group, a cyclohexane-1,4-diyl group, and a cyclooctane-1,5-diyl group; and polycyclic divalent alicyclic saturated hydrocarbon groups such as a norbornane-1,4-diyl group, a norbornane-2,5-diyl group, an adamantane-1,5-diyl group, and an adamantane-2,6-diyl group.

$L^{i2}$ is preferably an alkanediyl group having 1 to 14 carbon atoms, and more preferably an alkanediyl group having 1 to 11 carbon atoms.

Examples of the divalent hydrocarbon group having 1 to 14 carbon atoms represented by $L^{i3}$ include alkanediyl groups such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, an ethane-1,1-diyl group, a propane-1,1-diyl group, a propane-1,2-diyl group, a propane-2,2-diyl group, a pentane-2,4-diyl group, a 2-methylpropane-1,3-diyl group, a 2-methylpropane-1,2-diyl group, a pentane-1,4-diyl group, and a 2-methylbutane-1,4-diyl group;

monocyclic divalent alicyclic saturated hydrocarbon groups which are cycloalkanediyl groups such as a cyclobutane-1,3-diyl group, a cyclopentane-1,3-diyl group, a cyclohexane-1,4-diyl group, and a cyclooctane-1,5-diyl group; and polycyclic divalent alicyclic saturated hydrocarbon groups such as a norbornane-1,4-diyl group, a norbornane-2,5-diyl group, an adamantane-1,5-diyl group, and an adamantane-2,6-diyl group.

$L^{i3}$ is preferably an alkanediyl group having 1 to 14 carbon atoms, and more preferably an alkanediyl group having 1 to 11 carbon atoms.

$L^{i3}$ is preferably bonded to the p-position of a main chain bonded to a phenyl group.

Examples of the sulfur-containing compound include any one of a compound represented by formula (I-1) to a compound represented by formula (I-26). Of these, a compound represented by formula (I-1) to a compound represented by formula (I-13) are preferable, and a compound represented by formula (I-1), a compound represented by formula (I-4), and a compound represented by formula (I-11) are more preferable.

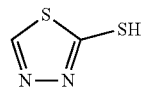

(I-1)

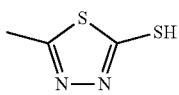

(I-2)

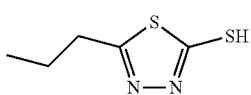

(I-3)

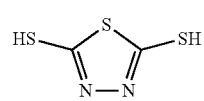

(I-4)

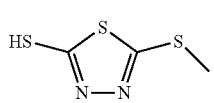

(I-5)

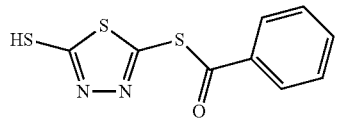

(I-6)

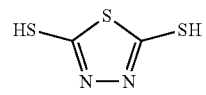

(I-7)

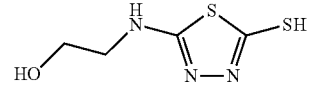

(I-8)

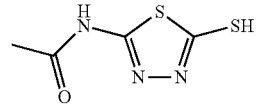

(I-9)

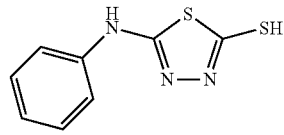

(I-10)

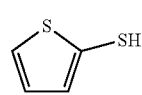

(I-11)

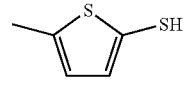

(I-13)

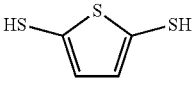

(I-14)

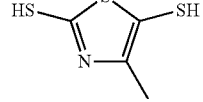

(I-15)

(I-16)

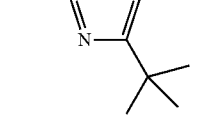

(I-17)

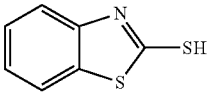

(I-18)

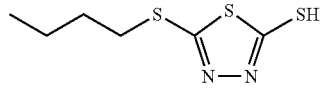

(I-19)

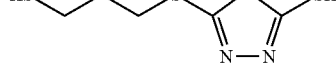

(I-20) 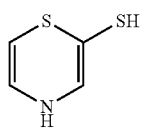

(I-21) 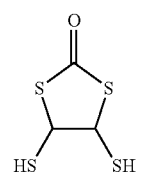

(I-22) 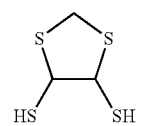

(I-23) 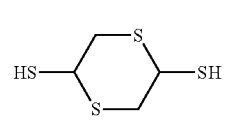

(I-24) 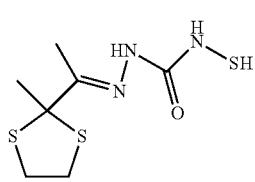

(I-25) 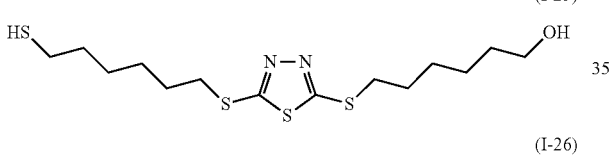

(I-26) 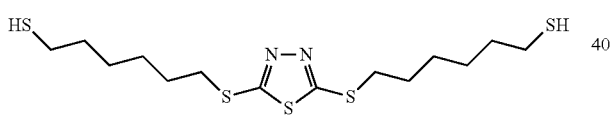

Examples of the sulfur-containing compound include a homopolymer composed of any one of structural units represented by formula (I-27) to formula (I-38), or a copolymer including one or more of these structural units.

A copolymer including one or more of structural units represented by formula (I-27) to formula (I-36) is preferable, and a copolymer including a structural unit represented by formula (I-33) is more preferable.

(I-27) 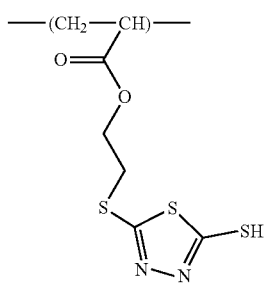

(I-28) 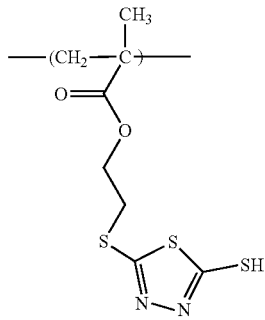

(I-29) 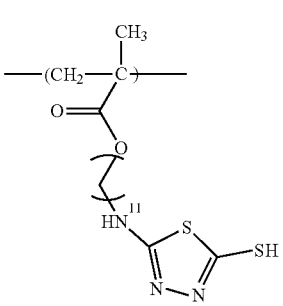

(I-30) 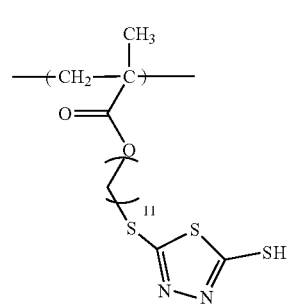

(I-31) 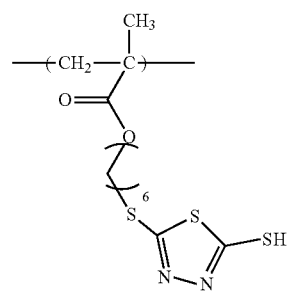

(I-32) 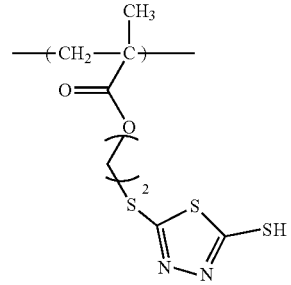

(I-33)
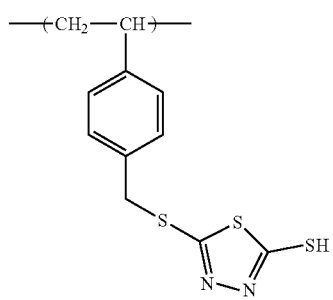
(I-34)
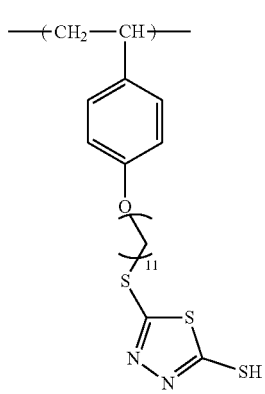
(I-35)
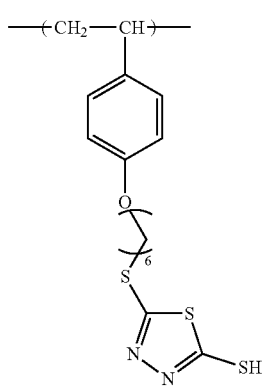
(I-36)
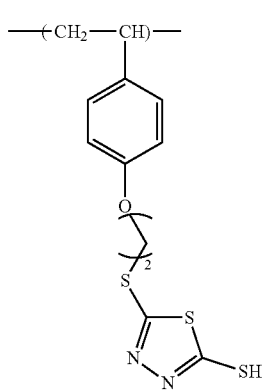
(I-37)
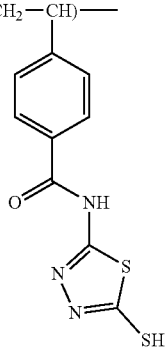
(I-38)
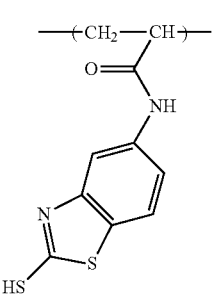
Examples of the copolymer include a copolymer composed of structural units represented by formula (I-39) to formula (I-48). Of these, a polymer including structural units represented by formula (I-39) to formula (I-44) is preferable.
(I-39)
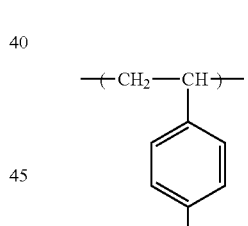
(I-40)
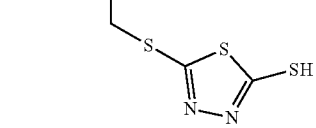
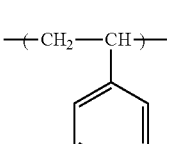

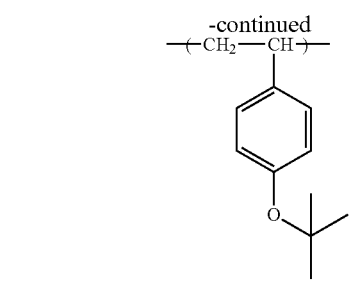
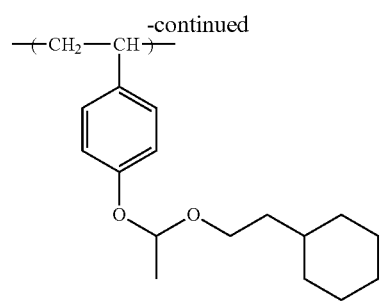
(I-41)
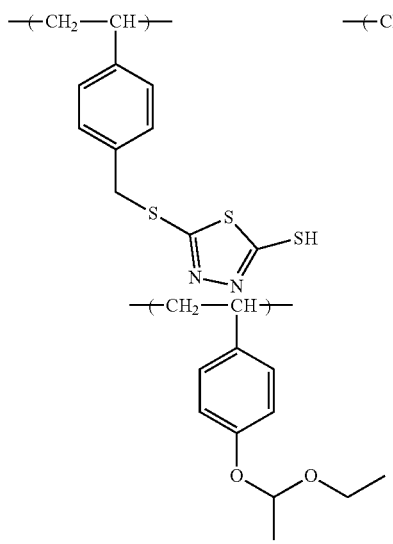
(I-42)
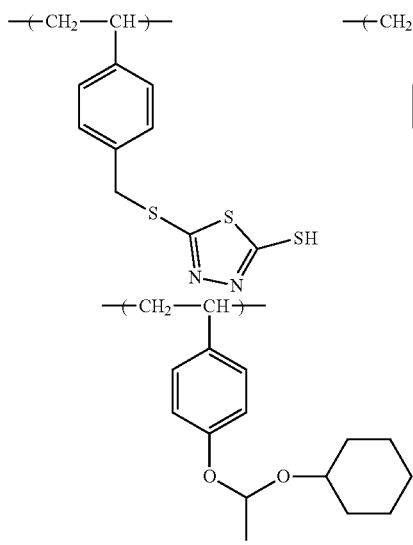
(I-43)
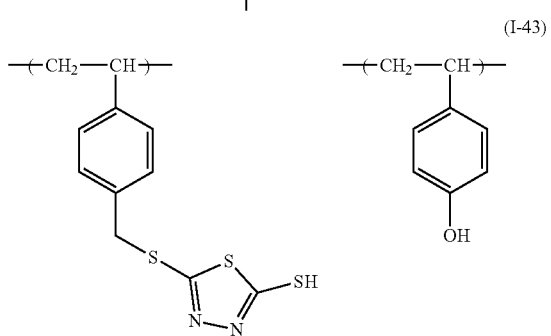
(I-44)
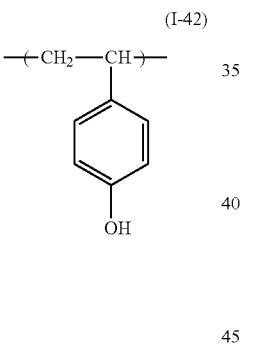
(I-45)
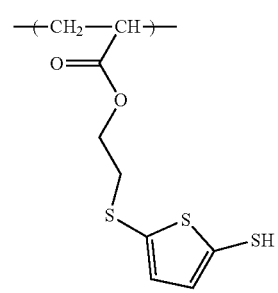
(I-46)
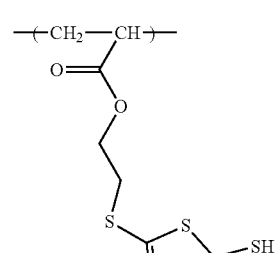
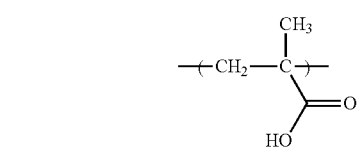

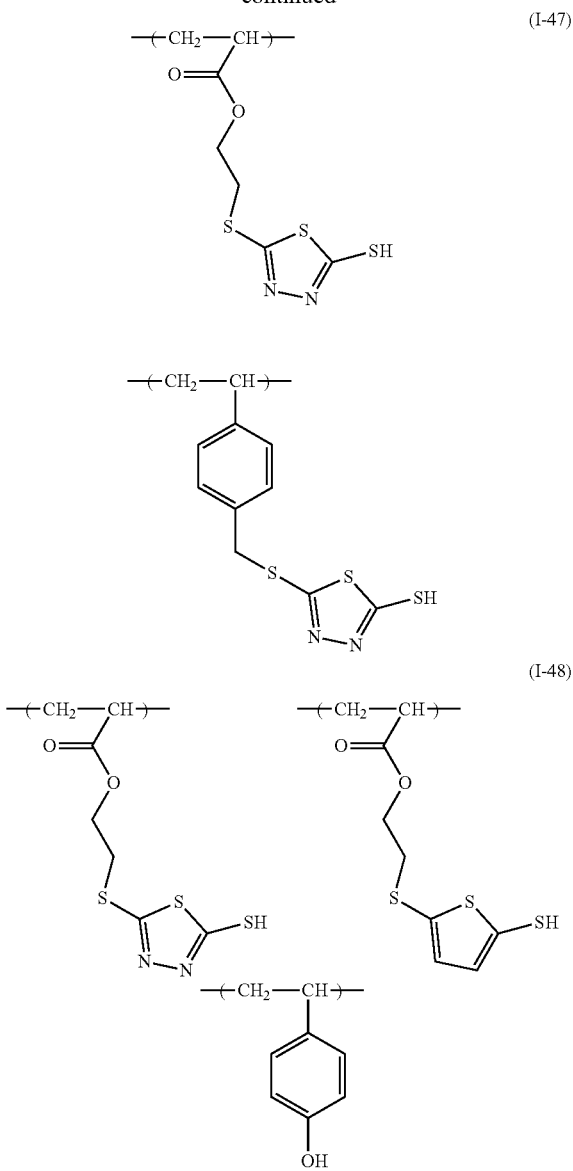

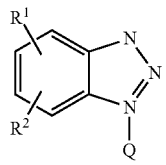

(IX)

wherein, in formula (IX), $R^1$ and $R^2$ each independently represent a hydrogen atom, a hydrocarbon group having 1 to 10 carbon atoms which may have a substituent, a carboxy group, an amino group, a hydroxy group, a cyano group, a formyl group, a sulfonylalkyl group, or a sulfo group, Q represents a hydrogen atom, a hydroxy group, a hydrocarbon group having 1 to 10 carbon atoms which may have a substituent, an aryl group, or —$R^{3x}$—N($R^{4x}$)($R^{5x}$), and the hydrocarbon group may have an amide bond and an ester bond in the structure, $R^{3x}$ represents an alkanediyl group having 1 to 6 carbon atoms, and  represents a bond to a nitrogen atom included in the ring, and $R^{4x}$ and $R^{5x}$ each independently represent a hydrogen atom, a hydroxy group, an alkyl group having 1 to 6 carbon atoms, a hydroxyalkyl group having 1 to 6 carbon atoms, or an alkoxyalkyl group having 1 to 6 carbon atoms.

The hydrocarbon group of $R^1$, $R^2$, and Q may be either an aliphatic hydrocarbon group or an aromatic hydrocarbon group, and may have a saturated and/or unsaturated bond.

The aliphatic hydrocarbon group is preferably an alkyl group, and examples of the alkyl group include a methyl group, an ethyl group, an n-propyl group, an isopropyl group, an n-butyl group, a sec-butyl group, a tert-butyl group, an n-pentyl group, a methylpentyl group, an n-hexyl group, an n-heptyl group and the like.

The aromatic hydrocarbon group is preferably an aryl group, and examples of the aryl group include a phenyl group, a naphthyl group, an anthryl group, a p-methylphenyl group, a p-tert-butylphenyl group, a p-adamantylphenyl group, a tolyl group, a xylyl group, a cumenyl group, a mesityl group, a biphenyl group, a phenanthryl group, a 2,6-diethylphenyl group, and a 2-methyl-6-ethylphenyl group.

Examples of the alkanediyl group of $R^{3x}$ are as mentioned above.

Examples of the substituent which may be possessed by the hydrocarbon group include a hydroxyalkyl group, an alkoxylalkyl group and the like.

Examples of the hydroxyalkyl group include a hydroxymethyl group, a hydroxyethyl group, a dihydroxyethyl group and the like.

Examples of the alkoxylalkyl include a methoxymethyl group, a methoxyethyl group, a dimethoxyethyl group and the like.

When the resist composition of the present invention is applied to a substrate with Cu formed thereon, it is preferable to use a compound in which Q in formula (IX) is represented by **—$R^{3x}$—N($R^{4x}$) ($R^{5x}$). Especially, when at least one of $R^{4x}$ and $R^{5X}$ is an alkyl group having 1 to 6 carbon atoms, a benzotriazole-based compound exhibits poor water solubility, but the compound is preferably used if other components capable of dissolving the compound exist.

When the resist composition of the present invention is applied to a substrate with an inorganic material layer (e.g., The sulfur-containing compound may be synthesized by a known method (e.g., JP 2010-79081 A), or may be an available product on the market. The polymer including the sulfur-containing compound may be an available product on the market (e.g., Bismuthiol (manufactured by Tokyo Chemical Industry Co., Ltd.), or may be synthesized by a known method (e.g., JP 2001-75277 A).

Examples of the aromatic hydroxy compound include phenol, cresol, xylenol, pyrocatechol (=1,2-dihydroxybenzene), tert-butylcatechol, resorcinol, hydroquinone, pyrogallol, 1,2,4-benzenetriol, salicyl alcohol, p-hydroxybenzyl alcohol, o-hydroxybenzyl alcohol, p-hydroxyphenethyl alcohol, p-aminophenol, m-aminophenol, diaminophenol, aminoresorcinol, p-hydroxybenzoic acid, o-hydroxybenzoic acid, 2,4-dihydroxybenzoic acid, 2,5-dihydroxybenzoic acid, 3,4-dihydroxybenzoic acid, 3,5-dihydroxybenzoic acid, gallic acid and the like.

Examples of the benzotriazole-based compound include a compound represented by formula (IX):

a polysilicon film, an amorphous silicon film, etc.), it is preferable to use a compound in which Q in formula (IX) is a water-soluble group. Specifically, Q is preferably a hydrogen atom, an alkyl group having 1 to 3 carbon atoms, a hydroxyalkyl group having 1 to 3 carbon atoms, a hydroxy group or the like. Whereby, anticorrosive properties of the substrate can be more effectively exerted.

Examples of the benzotriazole-based compound include benzotriazole, 5,6-dimethylbenzotriazole, 1-hydroxybenzotriazole, 1-methylbenzotriazole, 1-aminobenzotriazole, 1-phenylbenzotriazole, 1-hydroxymethylbenzotriazole, methyl 1-benzotriazolecarboxylate, 5-benzotriazolecarboxylic acid, 1-methoxy-benzotriazole, 1-(2,2-dihydroxyethyl)-benzotriazole, 1-(2,3-dihydroxypropyl)benzotriazole, or 2,2'-{[(4-methyl-1H-benzotriazol-1-yl)methyl]imino}bisethanol, 2,2'-{[(5-methyl-1H-benzotriazol-1-yl)methyl]imino}bisethanol, 2,2'-{[(4-methyl-1H-benzotriazol-1-yl)methyl]imino}bisethane, or 2,2'-{[(4-methyl-1H-benzotriazol-1-yl)methyl]imino}bispropane which are available on the market from BASF Corporation as "IRGAMET (registered trademark)" series.

Examples of the triazine-based compound include a compound represented by formula (II):

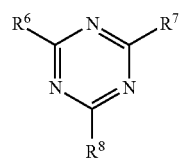

wherein, in formula (II), $R^6$, $R^7$, and $R^8$ each independently represent halogen, a hydrogen atom, a hydroxy group, an amino group, a mercapto group, a hydrocarbon group having 1 to 10 carbon atoms which may be substituted, an alkyloxy group having 1 to 10 carbon atoms which may be substituted, or a hydrocarbon group-substituted amino group having 1 to 10 carbon atoms.

Examples of the halogen atom include a fluorine atom, a chlorine atom, a bromine atom, and an iodine atom.

Examples of the hydrocarbon group and the alkyloxy group include those which are the same as mentioned above.

Examples of the triazine-based compound include 1,3,5-triazine-2,4,6-trithiol and the like.

Examples of the silicon-containing-based compound include a compound represented by formula (IIA):

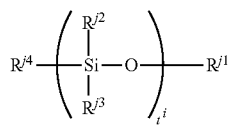

wherein, in formula (IIA), $R^{j1}$ represents an aliphatic hydrocarbon group having 1 to 5 carbon atoms or a mercaptoalkyl group having 1 to 5 carbon atoms, $R^{j2}$ to $R^{j4}$ each independently represent an aliphatic hydrocarbon group having 1 to 5 carbon atoms, an alkoxy group having 1 to 5 carbon atoms, a mercapto group, or a mercaptoalkyl group having 1 to 5 carbon atoms, and at least one of $R^{j2}$ to $R^{j4}$ is a mercapto group or a mercaptoalkyl group having 1 to 5 carbon atoms, and $t^i$ represents an integer of 1 to 10.

Examples of the aliphatic hydrocarbon group include alkyl groups such as a methyl group, an ethyl group, a propyl group, a butyl group, and a pentyl group.

Examples of the alkoxy group include a methoxy group and an ethoxy group.

Examples of the mercaptoalkyl group include a methylmercapto group, an ethylmercapto group, and a propylmercapto group.

$R^{j1}$ is preferably an aliphatic hydrocarbon group having 1 or 2 carbon atoms or a mercaptoalkyl group having 1 to 3 carbon atoms, and more preferably a methyl group or a mercaptopropyl group.

Preferably, $R^{j2}$ to $R^{j4}$ each independently represent an aliphatic hydrocarbon group having 1 or 2 carbon atoms or an alkoxy group having 1 or 2 carbon atoms, and more preferably a methyl group or a methoxy group. At least one of them is preferably a mercapto group or a mercaptoalkyl group having 1 to 3 carbon atoms, and more preferably a mercapto group or a mercaptopropyl group.

$R^{j2}$ and $R^{j3}$ may be the same or different from each other, and are preferably the same from the viewpoint of the productivity.

Examples of the compound represented by formula (IIA) include compounds represented by the following formula (II-1) to formula (II-7).

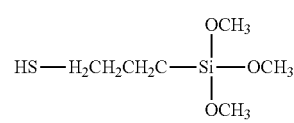

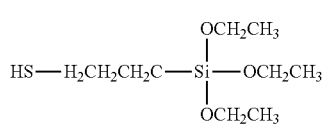

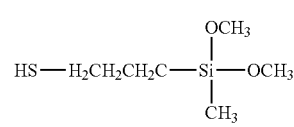

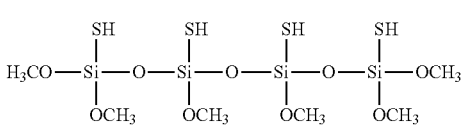

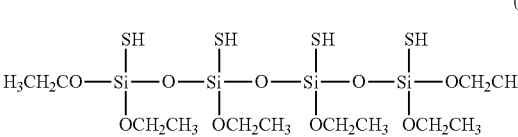

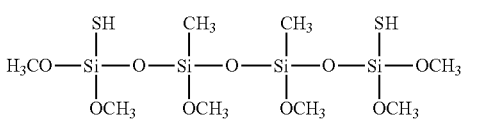

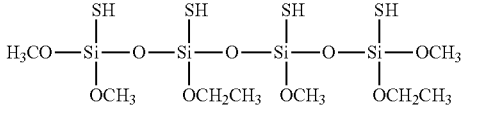

Of these, 3-mercaptopropyltrimethoxysilane or 3-mercaptopropyltriethoxysilane is preferable.

The content of the adhesion improver (E) is preferably 0.001% by mass or more, more preferably 0.002% by mass or more, and still more preferably 0.005% by mass or more, and is preferably 20% by mass or less, more preferably 10% by mass or less, still more preferably 4% by mass or less, yet more preferably 3% by mass or less, and particularly preferably 1% by mass or less, based on the total amount of the solid component of the resist composition. By adjusting the content in this range, it is possible to obtain a resist composition capable of forming a resist pattern with high accuracy and to ensure the adhesion between the resist pattern and the substrate.

<Other Components>

The resist composition of the present invention may also include components other than the components mentioned above (hereinafter sometimes referred to as "other components (F)"), as needed. The other components (F) are not particularly limited and it is possible to use various additives known in the resist field, for example, sensitizers, dissolution inhibitors, surfactants, stabilizers dyes and the like.

<Preparation of Resist Composition>

The resist composition of the present invention can be prepared by mixing a resin (A1) of the present invention, an acid generator (B), a quencher (C), a solvent (D), as well as a resin (A2), a resin (A3), an adhesion improver (E) and other component (F), as needed. The order of mixing these components is any order and is not particularly limited. It is possible to select, as the temperature during mixing, appropriate temperature according to the type of the resins and the solubility of the resins in the solvent (D) from 10 to 40° C. It is possible to select, as the mixing time, appropriate time according to the mixing temperature from 0.5 to 24 hours. The mixing means is not particularly limited and it is possible to use mixing with stirring.

After mixing the respective components, the mixture is preferably filtered through a filter having a pore diameter of about 0.1 to 50 µm.

<Method for Producing Resist Pattern>

The method for producing a resist pattern of the present invention comprises:

(1) a step of applying the resist composition of the present invention on a substrate, (2) a step of drying the applied composition to form a composition layer, (3) a step of exposing the composition layer, and (4) a step of developing the exposed composition layer.

The resist composition can be usually applied on a substrate using a conventionally used apparatus, such as a spin coater. Examples of the substrate include inorganic substrates such as a silicon wafer, and semiconductor devices (e.g., transistors, diodes, etc.) and the like may be formed in advance on the substrate. When using the resist composition of the present invention for formation of bumps, the substrate is preferably a substrate with a conductive material further laminated thereon. Examples of the conductive material include at least one metal selected from the group consisting of gold, copper, nickel, tin, palladium, and silver, or an alloy containing at least one metal selected from the group, and preferably copper or an alloy containing copper.

Before applying the resist composition, the substrate may be washed, and an antireflection film may be formed on the substrate.

The solvent is removed by drying the applied composition to form a composition layer. Drying is performed by evaporating the solvent using a heating device such as a hot plate (so-called "prebake"), or a decompression device. The heating temperature is preferably 50 to 200° C. and the heating time is preferably 30 to 600 seconds. The pressure during drying under reduced pressure is preferably about 1 to $1.0 \times 10^5$ Pa.

The thickness of a film of the composition obtained after drying is preferably 3 to 150 µm, and more preferably 4 to 100 µm.

The composition layer thus obtained is usually exposed using an aligner. It is possible to use, as an exposure source, various exposure sources, for example, light sources capable of emitting light having a wavelength of 345 to 436 nm (g-ray (wavelength of 436 nm), h-ray (wavelength of 405 nm), and i-ray (wavelength of 365 nm)); light sources capable of emitting laser beam in an ultraviolet region such as KrF excimer laser (wavelength of 248 nm), ArF excimer laser (wavelength of 193 nm), and $F_2$ excimer laser (wavelength of 157 nm); an exposure source capable of emitting harmonic laser beam in a far-ultraviolet or vacuum ultra violet region by wavelength-converting laser beam from a solid-state laser source (YAG or semiconductor laser); an exposure source capable of emitting electron beam or extreme ultraviolet light (EUV) and the like. In the present description, such exposure to radiation is sometimes collectively referred to as "exposure". The exposure is usually performed through a mask corresponding to a pattern to be required. When electron beam is used as the exposure source, exposure may be performed by direct writing without using the mask.

The exposed composition layer is subjected to a heat treatment (so-called "post-exposure bake") to promote the deprotection reaction in an acid-labile group. The heating temperature is usually about 50 to 200° C., and preferably about 70 to 150° C. The heating time is usually 40 to 400 seconds, and preferably 50 to 350 seconds.

The heated composition layer is usually developed with a developing solution using a development apparatus. Examples of the developing method include a dipping method, a paddle method, a spraying method, a dynamic dispensing method and the like. The developing temperature is preferably 5 to 60° C. and the developing time is preferably 5 to 600 seconds. It is possible to produce a positive resist pattern or negative resist pattern by selecting the type of the developing solution as follows.

When the positive resist pattern is produced from the resist composition of the present invention, an alkaline developing solution is used as the developing solution. The alkaline developing solution may be various aqueous alkaline solutions used in this field. Examples thereof include aqueous solutions of tetramethylammonium hydroxide and (2-hydroxyethyl)trimethylammonium hydroxide (commonly known as choline). The surfactant may be contained in the alkaline developing solution.

It is preferable that the developed resist pattern is washed with ultrapure water and then water remaining on the substrate and the pattern is removed.

When the negative resist pattern is produced from the resist composition of the present invention, a developing solution containing an organic solvent (hereinafter sometimes referred to as "organic developing solution") is used as the developing solution.

Examples of the organic solvent contained in the organic developing solution include ketone solvents such as 2-hexanone and 2-heptanone; glycol ether ester solvents such as propylene glycol monomethyl ether acetate; ester solvents such as butyl acetate; glycol ether solvents such as propylene glycol monomethyl ether; amide solvents such as N,N-dimethylacetamide; and aromatic hydrocarbon solvents such as anisole.

The content of the organic solvent in the organic developing solution is preferably 90% by mass or more and 100% by mass or less, more preferably 95% by mass or more and 100% by mass or less, and still more preferably the organic developing solution is substantially composed only of the organic solvent.

Particularly, the organic developing solution is preferably a developing solution containing butyl acetate and/or 2-heptanone. The total content of butyl acetate and 2-heptanone in the organic developing solution is preferably 50% by mass or more and 100% by mass or less, more preferably 90% by mass or more and 100% by mass or less, and still more preferably the organic developing solution is substantially composed only of butyl acetate and/or 2-heptanone.

The surfactant may be contained in the organic developing solution. A trace amount of water may be contained in the organic developing solution.

During development, the development may be stopped by replacing by a solvent with the type different from that of the organic developing solution.

The developed resist pattern is preferably washed with a rinsing solution. The rinsing solution is not particularly limited as long as it does not dissolve the resist pattern, and it is possible to use a solution containing an ordinary organic solvent which is preferably an alcohol solvent or an ester solvent.

After washing, the rinsing solution remaining on the substrate and the pattern is preferably removed.

<Applications>

The resist composition of the present invention is useful for production of a thick resist film. For example, it is useful for production of a resist film having a thickness of 1 to 150 μm.

The resist composition of the present invention is useful for production of bumps and rewiring by a plating step. When producing using the resist composition, bumps and rewiring are usually formed by the following procedure. Whereby, it is possible to produce a resist pattern with particularly excellent pattern shape.

First, a conductive material (seed metal) is laminated on a wafer with a semiconductor device formed thereon, thus forming a conductive layer. Then, a resist pattern is formed on the conductive layer by the resist composition of the present invention. Then, using the resist pattern as a template, an electrode material (e.g., Cu, Ni, solder, etc.) is deposited by plating, and the resist pattern and the conductive layer remaining under the resist pattern are removed by etching, thus making it possible to form bumps and rewiring. After removing the conductive layer, those obtained by dissolving the electrode material by a heat treatment, as needed, may be used as bumps.

EXAMPLES

The present invention will be described more specifically by way of Examples. Percentages and parts expressing the contents or amounts used in the Examples are by mass unless otherwise specified.

The weight-average molecular weight is a value determined by gel permeation chromatography under the following conditions:

Equipment: HLC-8120 GPC type (manufactured by TOSOH CORPORATION)

Column: TSKgel Multipore $H_{XL}$-M×3+guardcolumn (manufactured by TOSOH CORPORATION)

Eluent: tetrahydrofuran

Flow rate: 1.0 mL/min

Detector: RI detector

Column temperature: 40° C.

Injection amount: 100 μl

Molecular weight standards: polystyrene standard (manufactured by TOSOH CORPORATION)

Synthesis Example 1 [Synthesis of Resin A1-1]

In a flask, 33.0 parts of a phenol novolak resin (PSM-4326, manufactured by Gun Ei Chemical Industry Co., Ltd.) and 198.0 parts of propylene glycol monomethyl ether acetate were charged and dissolved by raising the temperature to 60° C., followed by cooling to 40° C.

To the mixture thus obtained, 20.0 parts of acetonitrile and 6.71 parts of N,N-dimethyl-4-aminopyridine were added dropwise at 40° C. over 20 minutes, followed by cooling to room temperature. To the mixture thus obtained, 9.77 parts of di-tert-butyl dicarbonate was added dropwise and, after stirring at room temperature, the reaction was performed for 24 hours. Then, the reaction solution was diluted with 99 parts of methyl isobutyl ketone and then washed with 183 parts of an aqueous 2% oxalic acid solution added. After separation, 183 parts of ion-exchanged water was added to the organic layer, and washing and separation were repeated five times, and then the organic layer thus obtained was concentrated. To the concentrate, propylene glycol monomethyl ether acetate was added, followed by concentration to obtain 61.24 parts of a resin solution. The liquid thus obtained is a resin solution in which a hydroxy group of a phenol novolak resin is partially tert-butoxycarbonylated. This resin was analyzed by $^{13}$C-NMR and found that 10.5% of the hydroxy group of the phenol novolak resin was substituted with a tert-butoxycarbonyloxy group. The concentration of the resin solution was measured by a dry weight reduction method and found to be 40.5%. This resin is referred to as a resin A1-1. The resin A1-1 had a weight-average molecular weight of $6.3 \times 10^3$.

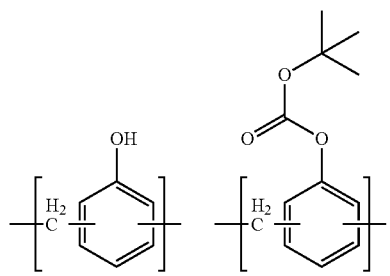

A1-1

Synthesis Example 2 [Synthesis of Resin A1-2]

In a flask, 33.0 parts of a phenol novolak resin (PSM-4326, manufactured by Gun Ei Chemical Industry Co., Ltd.) and 198.0 parts of propylene glycol monomethyl ether acetate were charged and dissolved by raising the temperature to 60° C., followed by cooling to 40° C.

To the mixture thus obtained, 20.0 parts of acetonitrile and 6.71 parts of N,N-dimethyl-4-aminopyridine were added dropwise at 40° C. over 20 minutes, followed by cooling to room temperature. To the mixture thus obtained, 14.98 parts of di-tert-butyl dicarbonate was added dropwise and, after stirring at room temperature, the reaction was performed for 24 hours. Then, the reaction solution was diluted with 99 parts of methyl isobutyl ketone and then washed with 183 parts of an aqueous 2% oxalic acid solution added. After separation, 183 parts of ion-exchanged water was added to the organic layer, and washing and separation were repeated five times, and then the organic layer thus obtained was concentrated. To the concentrate, propylene glycol monomethyl ether acetate was added, followed by concentration to obtain 83.50 parts of a resin solution. The liquid thus obtained is a resin solution in which a hydroxy group of a phenol novolak resin is partially tert-butoxycarbonylated. This resin was analyzed by 13C-NMR and found that 15.3% of the hydroxy group of the phenol novolak resin was substituted with a tert-butoxycarbonyloxy group. The concentration of the resin solution was measured by a dry weight reduction method and found to be 38.2%. This resin is referred to as a resin A1-2. The resin A1-2 had a weight-average molecular weight of $6.5 \times 10^3$.

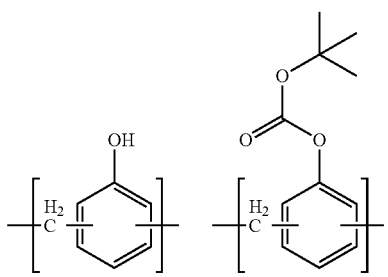

A1-2

Synthesis Example 3 [Synthesis of Resin A1-3]

In a flask, 33.0 parts of a phenol novolak resin (PSM-4326, manufactured by Gun Ei Chemical Industry Co., Ltd.) and 198.0 parts of propylene glycol monomethyl ether acetate were charged and dissolved by raising the temperature to 60° C., followed by cooling to 40° C.

To the mixture thus obtained, 20.0 parts of acetonitrile and 6.71 parts of N,N-dimethyl-4-aminopyridine were added dropwise at 40° C. over 20 minutes, followed by cooling to room temperature. To the mixture thus obtained, 17.98 parts of di-tert-butyl dicarbonate was added dropwise and, after stirring at room temperature, the reaction was performed for 24 hours. Then, the reaction solution was diluted with 99 parts of methyl isobutyl ketone and then washed with 183 parts of an aqueous 2% oxalic acid solution added. After separation, 183 parts of ion-exchanged water was added to the organic layer, and washing and separation were repeated five times, and then the organic layer thus obtained was concentrated. To the concentrate, propylene glycol monomethyl ether acetate was added, followed by concentration to obtain 79.76 parts of a resin solution. The liquid thus obtained is a resin solution in which a hydroxy group of a phenol novolak resin is partially tert-butoxycarbonylated. This resin was analyzed by 13C-NMR and found that 20.1% of the hydroxy group of the phenol novolak resin was substituted with a tert-butoxycarbonyloxy group. The concentration of the resin solution was measured by a dry weight reduction method and found to be 37.9%. This resin is referred to as a resin A1-3. The resin A1-3 had a weight-average molecular weight of $7.1 \times 10^3$.

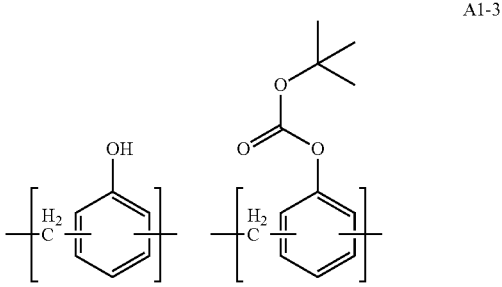

A1-3

Synthesis Example 4 [Synthesis of Resin A1-4]

In a flask, 33.0 parts of a phenol novolak resin (PSM-4326, manufactured by Gun Ei Chemical Industry Co., Ltd.) and 198.0 parts of propylene glycol monomethyl ether acetate were charged and dissolved by raising the temperature to 60° C., followed by cooling to 40° C.

To the mixture thus obtained, 15.28 parts of triethylamine and 8.39 parts of N,N-dimethyl-4-aminopyridine were added dropwise at 40° C. over 20 minutes, followed by cooling to room temperature. To the mixture thus obtained, 38.96 parts of di-tert-butyl dicarbonate was added dropwise at room temperature and, after raising the temperature to 60° C. and stirring at the temperature, the reaction was performed for 8 hours. After cooling, 9.06 parts of acetic acid and 183 parts of ion-exchanged water was added.

Then, the reaction solution was diluted with 99 parts of methyl isobutyl ketone and then washed with 183 parts of an aqueous 2% oxalic acid solution added. After separation, 183 parts of ion-exchanged water was added to the organic layer, and washing and separation were repeated five times, and then the organic layer thus obtained was concentrated. To the concentrate, propylene glycol monomethyl ether acetate was added, followed by concentration to obtain 87.0 parts of a resin solution. The liquid thus obtained is a resin solution in which a hydroxy group of a phenol novolak resin is partially tert-butoxycarbonylated. This resin was analyzed by $^{13}$C-NMR and found that 35.1% of the hydroxy group of the phenol novolak resin was substituted with a tert-butoxycarbonyloxy group. The concentration of the resin solution was measured by a dry weight reduction method and found to be 35.3%. This resin is referred to as a resin A1-4. The resin A1-4 had a weight-average molecular weight of $8.9 \times 10^3$.

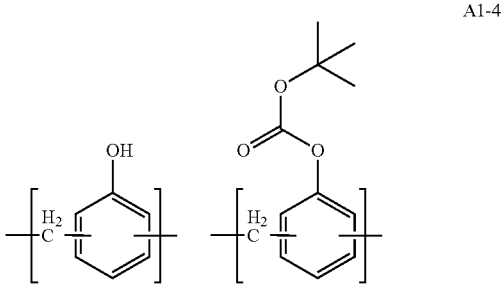

A1-4

Synthesis Example 5 [Synthesis of Resin A2-1]

In a flask, 120 parts of a phenol novolak resin (PSM-4326, manufactured by Gun Ei Chemical Industry Co., Ltd.) and 960 parts of methyl isobutyl ketone were charged and dissolved. The phenol novolak resin solution thus obtained was washed five times with ion-exchanged water, followed by separation. The organic layer thus obtained was concentrated until the amount became 327.3 parts. The concentration of the resin in the resin solution thus obtained was 35.2%.

In a flask, 56.8 parts of the resin solution thus obtained, 76.52 parts of methyl isobutyl ketone, and 0.0036 part of p-toluenesulfonic acid monohydrate were charged. To this mixture, 8.81 parts of ethyl vinyl ether was added dropwise and the reaction was performed at room temperature for 3 hours. To this reaction solution, ion-exchanged water was added and, after stirring and allowing to stand, the organic layer was separated. Washing with ion-exchanged water was further performed four times, i.e., five times in total. Then, the organic layer was taken out and concentrated. Then, propylene glycol monomethyl ether acetate was added for azeotropic removal of water and methyl isobutyl ketone, and then the organic layer was further concentrated to obtain 57.44 parts of a resin solution. The resin solution thus obtained is a resin solution in which a hydroxy group of a phenol novolak resin is partially 1-ethoxyethylated. This resin was analyzed by $^1$H-NMR and found that 53.0% of the hydroxy group of the phenol novolak resin was substituted with 1-ethoxyethyl ether. The concentration of the resin solution was measured by a dry weight reduction method and found to be 45.0%. This resin is referred to as a resin A2-1. The resin A2-1 had a weight-average molecular weight of $7.2 \times 10^3$.

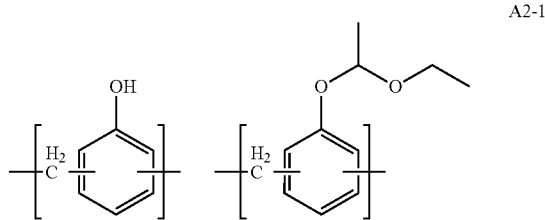

A2-1

Synthesis Example 6 [Synthesis of Resin A2-2]

20 Parts of poly-p-hydroxystyrene (S-4P; manufactured by Maruzen Petrochemical CO, LTD.) was dissolved in 240 parts of methyl isobutyl ketone at room temperature and then concentrated by an evaporator. In a four-necked flask equipped with a reflux condenser, a stirrer, and a thermometer, 0.003 part of the concentrated resin solution and p-toluenesulfonic acid dihydrate were charged. While maintaining the mixture thus obtained at 20 to 25° C., 5.05 parts of ethyl vinyl ether was added dropwise over 10 minutes to the mixture thus obtained. The mixture was stirred at 20 to 25° C. for 2 hours. The reaction mixture thus obtained was diluted with 200 parts of methyl isobutyl ketone, and then washing with ion-exchanged water and separation were performed five times. The organic layer thus obtained was concentrated until the amount became 45 parts using an evaporator and, after adding 150 parts of propylene glycol monomethyl ether acetate, concentration was performed again to obtain 78 parts (solid component of 29%) of a propylene glycol monomethyl ether acetate solution of a resin A2-2. The resin A2-2 had a weight-average molecular weight of $1.16 \times 10^4$. The ratio of the hydroxy group in poly-p-hydroxystyrene to be substituted with an ethoxyethoxy group was 40.9%.

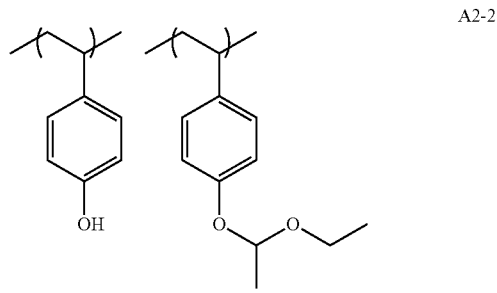

A2-2

Synthesis Example 7 [Synthesis of Resin A3-1]

In a four-necked flask equipped with a stirrer, a reflux condenser, and a thermometer, 413.5 parts of 2,5-xylenol, 103.4 parts of salicylaldehyde, 20.1 parts of p-toluenesulfonic acid, and 826.9 parts of methanol were charged and the temperature was raised to a reflux state, followed by maintaining the temperature for 4 hours. After cooling, 1,320 parts of methyl isobutyl ketone were added and 1,075 parts of the solvent was distilled off under normal pressure. 762.7 Parts of m-cresol and 29.0 parts of 2-tert-butyl-5-methylphenol were added and the temperature was raised to 65° C., and then 678 parts of an aqueous 37% formalin solution was added dropwise over 1.5 hours while adjusting the temperature to 87° C. after completion of the dropwise addition. The temperature of the mixture thus obtained was maintained at 87° C. 10 hours and 1,115 parts of methyl isobutyl ketone was added, followed by washing with ion-exchanged water and further separating three times. To the mixture thus obtained, 500 parts of methyl isobutyl ketone was added and vacuum concentration was carried out until the total amount reached 3,435 parts. To the mixture thus obtained, 3,796 parts of methyl isobutyl ketone and 4,990 parts of n-heptane were added and the temperature was raised to 60° C., followed by stirring for 1 hour. Thereafter, a layer containing the resin, which is the lower layer, was taken out by separation, diluted with 3,500 parts of propylene glycol monomethyl ether acetate and then concentrated to obtain 1,690 parts (solid component of 43%) of a propylene glycol monomethyl ether acetate solution of a resin A3-1. The novolak resin A3-1 had a weight-average molecular weight of $7 \times 10^3$.

Synthesis Example 8 [Synthesis of Resin A4-1]

33.0 Parts of poly-p-hydroxystyrene (S-4P; manufactured by Maruzen Petrochemical CO, LTD.) and 198.0 parts of propylene glycol monomethyl ether acetate were mixed and the temperature was raised to 60° C., followed by dissolution and further cooling to 40° C.

To the mixture thus obtained, 20.0 parts of acetonitrile and 6.71 g of N,N-dimethyl-4-aminopyridine were added dropwise at 40° over 20 minutes, followed by cooling to room temperature. To the mixture thus obtained, 29.97 parts of di-tert-butyl dicarbonate was added dropwise and, after stirring at room temperature, the reaction was performed for 24 hours. Then, the reaction solution was diluted with 99 parts of methyl isobutyl ketone and then washed with 183 parts of an aqueous 2% oxalic acid solution added. After separation, 183 parts of ion-exchanged water was added to the organic layer, and washing and separation were repeated five times, and then the organic layer thus obtained was concentrated. To the concentrate, propylene glycol monomethyl ether acetate was added, followed by concentration to obtain 106.7 parts of a resin solution. The liquid thus obtained is a resin solution in which a hydroxy group of poly-p-hydroxystyrene is partially tert-butoxycarbonylated. This resin was analyzed by $^{13}$C-NMR and found that 36.0% of the hydroxy group of the poly-p-hydroxystyrene was substituted with a tert-butoxycarbonyloxy group. The concentration of the resin solution was measured by a dry weight reduction method and found to be 40.2%. This resin is referred to as a resin A4-1. The resin A4-1 had a weight-average molecular weight of $1.33 \times 10^4$.

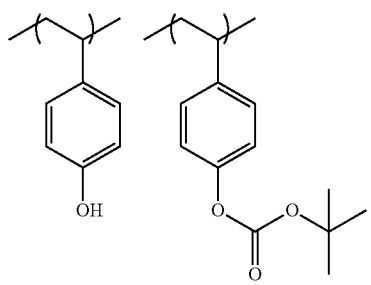

A4-1

<Preparation of Resist Composition>

The respective components were mixed in each amount (parts by mass, parts by mass of the resin represent parts by mass as solid content) shown in Table 1 and dissolved in a solvent (parts by mass of the solvent shown in Table 1 represent parts by mass of the solvent included in the entire composition) and then the mixture was filtered through a fluororesin filter having a pore diameter of 5 μm to prepare resist compositions.

TABLE 1

| Resist composition | Resin (A) | Acid generator (B) | Quencher (C) | Adhesion improver (E) | Solvent (D) |
|---|---|---|---|---|---|
| Composition 1 | A1-1 = 1.35 parts<br>A2-1 = 4.725 parts<br>A3-1 = 7.425 parts | B1 = 0.24 parts | C1 = 0.05 parts | — | D1 = 47 parts |
| Composition 2 | A1-2 = 1.35 parts<br>A2-1 = 4.725 parts<br>A3-1 = 7.425 parts | B1 = 0.24 parts | C1 = 0.05 parts | — | D1 = 47 parts |
| Composition 3 | A1-3 = 1.35 parts<br>A2-1 = 4.725 parts<br>A3-1 = 7.425 parts | B1 = 0.24 parts | C1 = 0.05 parts | — | D1 = 47 parts |
| Composition 4 | A1-1 = 1.35 parts<br>A2-1 = 6.075 parts<br>A3-1 = 6.075 parts | B1 = 0.24 parts | C1 = 0.05 parts | — | D1 = 47 parts |
| Composition 5 | A1-2 = 1.35 parts<br>A2-1 = 6.075 parts<br>A3-1 = 6.075 parts | B1 = 0.24 parts | C1 = 0.05 parts | — | D1 = 47 parts |
| Composition 6 | A1-3 = 1.35 parts<br>A2-1 = 6.075 parts<br>A3-1 = 6.075 parts | B1 = 0.24 parts | C1 = 0.05 parts | — | D1 = 47 parts |
| Composition 7 | A1-4 = 7.425 parts<br>A3-1 = 6.075 parts | B1 = 0.24 parts | C1 = 0.05 parts | — | D1 = 53 parts |
| Composition 8 | A1-1 = 0.675 parts<br>A2-2 = 7.425 parts<br>A3-1 = 5.400 parts | B1 = 0.24 parts | C1 = 0.05 parts | E1 = 0.016 parts | D1 = 22 parts |
| Comparative Composition 1 | A1-1 = 1.35 parts<br>A2-1 = 4.725 parts<br>A3-1 = 7.425 parts | B1 = 0.24 parts | — | — | D1 = 47 parts |
| Comparative Composition 2 | A2-1 = 4.725 parts<br>A3-1 = 8.775 parts | B1 = 0.24 parts | C1 = 0.05 parts | — | D1 = 47 parts |
| Comparative Composition 3 | A4-1 = 1.35 parts<br>A2-1 = 4.725 parts<br>A3-1 = 7.425 parts | B1 = 0.24 parts | C1 = 0.05 parts | — | D1 = 47 parts |
| Comparative Composition 4 | A2-2 = 7.425 parts<br>A3-1 = 6.075 parts | B1 = 0.24 parts | C1 = 0.05 parts | E1 = 0.016 parts | D1 = 22 parts |
| Comparative Composition 5 | A2-1 = 7.425 parts<br>A3-1 = 6.075 parts | B1 = 0.24 parts | C1 = 0.05 parts | E1 = 0.016 parts | D1 = 21 parts |

<Resin>
A1-1: Resin A1-1
A1-2: Resin A1-2
A1-3: Resin A1-3
A1-4: Resin A1-4
A2-1: Resin A2-1
A2-2: Resin A2-2
A3-1: Resin A3-1
A4-1: Resin A4-1

<Acid Generator (B)>
B1: N-hydroxynaphthalimide triflate (NAI-105; manufactured by Midori Kagaku Co., Ltd.)

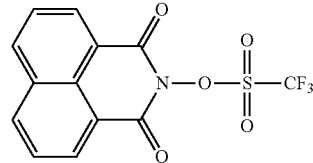 [SMILES: O=C1c2cccc3cccc(c23)C(=O)N1OS(=O)(=O)C(F)(F)F]

<Quencher (C)>
C1: 2,4,5-Triphenylimidazole (manufactured by Tokyo Chemical Industry Co., Ltd.)

<Adhesion Improver>
E1: Bismuthiol (manufactured by Tokyo Chemical Industry Co., Ltd.)

<Solvent>
Propylene glycol monomethyl ether acetate

Examples 1 to 7, Comparative Examples 1 to 3

(Evaluation of Exposure of Resist Composition with i-Ray)

On a 4-inch substrate where copper had been vapor-deposited on a silicon wafer, each of the resist compositions prepared as above was spin-coated so that the thickness of the resulting film became 1.5 μm after pre-baking.

Then, the substrate was subjected to pre-baking on a direct hotplate at 110° C. for 180 seconds to form a composition layer. Using an i-ray stepper (NSR-2005i9C, manufactured by Nikon Corporation, NA=0.5) and a mask for forming a 1:1 line-and-space pattern with (line width of 1 μm), each wafer thus formed with the composition layer was subjected to exposure with the exposure quantity being varied stepwise.

After exposure, each wafer was subjected to post-exposure baking on a hotplate at 120° C. for 60 seconds, and each wafer was subjected to paddle development for 180 seconds with an aqueous 2.38% by mass tetramethylammonium hydroxide solution to obtain resist patterns.

The resist pattern obtained after development was observed by a scanning electron microscope and effective sensitivity was defined as the exposure dose at which a 1:1 line-and-space pattern with a line width of 1 μm was obtained.

<Evaluation of Pattern Shape>

Evaluation of pattern shape: Line patterns with a width of 1 μm obtained in the effective sensitivity were observed by a scanning electron microscope at a magnification of 10,000 times. Line patterns where a top shape and a hemline shape are close to rectangular and satisfactory [FIG. 1(a)] were rated "Good", while line patterns where a top shape is as shown in [FIG. 1(b)] or a taper shape were rated "Bad". The results are shown in Table 2.

<Change Over Time>

The resist composition thus prepared was stored at −5° C. and 40° C. for two weeks, and the above i-ray exposure evaluation of the stored resist composition was performed. The resist composition where the effective sensitivity of the resist composition stored at 40° C. accounts for 90% to 110% of the effective sensitivity of the resist composition stored at −5° C. was rated "Good", while the effective sensitivity of the resist composition stored at 40° C. accounts for less than 90% or more than 110% of the effective sensitivity of the resist composition stored at −5° C. was rated "Bad".

<Evaluation of Plating Resistance>

A wafer with a pattern was fabricated at the effective sensitivity obtained in the above i-ray exposure evaluation, and then immersed in a Cu plating solution for 10 minutes, 30 minutes, and 60 minutes.

The immersed wafer with a pattern was observed by an optical microscope and a line-and-space pattern with a line width of 1 μm was observed.

The wafer where pattern collapse is observed at the immersion time of 10 minutes was rated "D", the wafer where pattern collapse is observed at the immersion time of 30 minutes was rated "C", the wafer where pattern collapse is observed at the immersion time of 60 minutes was rated "B" and the wafer where pattern collapse is not observed at the immersion time of 60 minutes was rated "A".

TABLE 2

|  | Resist composition | Pattern shape | Change over time | Plating resistance |
| --- | --- | --- | --- | --- |
| Example 1 | Composition 1 | Good (a) | Good | C |
| Example 2 | Composition 2 | Good (a) | Good | B |
| Example 3 | Composition 3 | Good (a) | Good | B |
| Example 4 | Composition 4 | Good (a) | Good | B |
| Example 5 | Composition 5 | Good (a) | Good | B |
| Example 6 | Composition 6 | Good (a) | Good | B |
| Example 7 | Composition 7 | Good (a) | Good | A |
| Comparative Example 1 | Comparative Composition 1 | Good (a) | Bad | C |
| Comparative Example 2 | Comparative Composition 2 | Not resolved | — | — |
| Comparative Example 3 | Comparative Composition 3 | Not resolved | — | — |

Example 8, Comparative Examples 4 to 6

(Evaluation of Exposure of Resist Composition with i-Ray)

On a 4-inch substrate where copper had been vapor-deposited on a silicon wafer, each of the resist compositions prepared as above was spin-coated so that the thickness of the resulting film became 6 μm after pre-baking.

Then, the substrate was subjected to pre-baking on a direct hotplate at 110° C. for 180 seconds to form a composition layer. Using an i-ray stepper (NSR-2005i9C, manufactured by Nikon Corporation, NA=0.5) and a mask for forming a 1:1 line-and-space pattern with (line width of 2 μm), each wafer thus formed with the composition layer was subjected to exposure with the exposure quantity being varied stepwise.

After exposure, each wafer was subjected to post-exposure baking on a hotplate at 120° C. for 60 seconds, and each wafer was subjected to paddle development for 180 seconds with an aqueous 2.38% by mass tetramethylammonium hydroxide solution to obtain resist patterns.

The resist pattern obtained after development was observed by a scanning electron microscope and effective sensitivity was defined as the exposure dose at which a 1:1 line-and-space pattern with a line width of 2 μm was obtained.

<Evaluation of Pattern Shape>

Evaluation of pattern shape: Line patterns with a width of 2 μm obtained in the effective sensitivity were observed by a scanning electron microscope at a magnification of 10,000 times. Line patterns where a top shape and a hemline shape are close to rectangular and satisfactory [FIG. 1(a)] were rated "Good", while line patterns where a top shape is as shown in [FIG. 1(b)] or a taper shape were rated "Bad".

<Change Over Time>

The resist composition thus prepared was stored at −5° C. and 40° C. for two weeks, and the above i-ray exposure evaluation of the stored resist composition was performed. The resist composition where the effective sensitivity of the resist composition stored at 40° C. accounts for 90% to 110% of the effective sensitivity of the resist composition stored at −5° C. was rated "Good", while the effective sensitivity of the resist composition stored at 40° C. accounts for less than 90% or more than 110% of the effective sensitivity of the resist composition stored at −5° C. was rated "Bad".

<Evaluation of Plating Resistance>

A wafer with a pattern was fabricated at the effective sensitivity obtained in the above i-ray exposure evaluation, and then immersed in a Cu plating solution for 10 minutes, 30 minutes, and 60 minutes.

The immersed wafer with a pattern was observed by an optical microscope and a line-and-space pattern with a line width of 2 μm was observed.

The wafer where pattern collapse is observed at the immersion time of 10 minutes was rated "D", the wafer where pattern collapse is observed at the immersion time of 30 minutes was rated "C", the wafer where pattern collapse is observed at the immersion time of 60 minutes was rated "B" and the wafer where pattern collapse is not observed at the immersion time of 60 minutes was rated "A".

TABLE 3

|  | Resist composition | Pattern shape | Change over time | Plating resistance |
| --- | --- | --- | --- | --- |
| Example 8 | Composition 8 | Good (a) | Good | A |
| Comparative Example 4 | Comparative Composition 4 | Not resolved | — | — |
| Comparative Example 5 | Comparative Composition 5 | Not resolved | — | — |

INDUSTRIAL APPLICABILITY

According to the resist composition of the present invention, it is possible to produce a resist pattern with small change over time and excellent pattern shape.

The invention claimed is:

1. A resist composition comprising a novolak resin in which a hydroxy group is substituted with a group represented by formula (3), an alkali-soluble resin, an acid generator, a quencher, and a solvent:

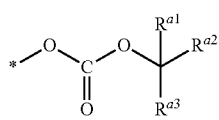
(3A)

wherein, in formula (3), $R^{a10}$ represents a hydrocarbon group having 1 to 20 carbon atoms, and * represents a bond.

2. The resist composition according to claim 1, wherein the novolak resin is a phenol novolak resin.

3. The resist composition according to claim 1, further comprising a resin having a group represented by formula (2):

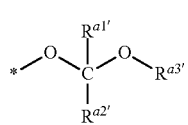
(2)

wherein, in formula (2), $R^{a1'}$ and $R^{a2'}$ each independently represent a hydrogen atom or a hydrocarbon group having 1 to 12 carbon atoms, and $R^{a3'}$ represents a hydrocarbon group having 1 to 20 carbon atoms, or
$R^{a1'}$ represents a hydrogen atom or a hydrocarbon group having 1 to 12 carbon atoms, $R^{a2'}$ and $R^{a3'}$ are bonded to each other to form a heterocyclic group having 2 to 20 carbon atoms together with carbon atoms and oxygen atoms to which $R^{a2'}$ and $R^{a3'}$ are bonded, a methylene group included in the hydrocarbon group having 1 to 12 carbon atoms, the hydrocarbon group having 1 to 20 carbon atoms, and the heterocyclic group having 2 to 20 carbon atoms may be substituted with an oxygen atom or a sulfur atom, and * represents a bond.

4. The resist composition according to claim 3, wherein the resin having a group represented by formula (2) is a resin including a structural unit represented by formula (a1-2):

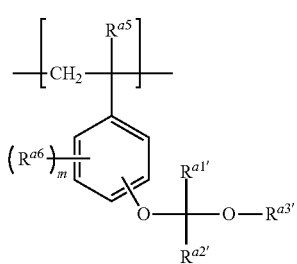
(a1-2)

wherein, in formula (a1-2),
$R^{a1'}$ and $R^{a2'}$ each independently represent a hydrogen atom or a hydrocarbon group having 1 to 12 carbon atoms, $R^{a3'}$ represents a hydrocarbon group having 1 to 20 carbon atoms, or
$R^{a1'}$ represents a hydrogen atom or a hydrocarbon group having 1 to 12 carbon atoms, $R^{2'}$ and $R^3$ are bonded to each other to form a divalent heterocyclic group having 2 to 20 carbon atoms together with carbon atoms and oxygen atoms to which $R^{a2'}$ and $R^{a3'}$ are bonded, a methylene group included in the hydrocarbon group having 1 to 12 carbon atoms, the hydrocarbon group having 1 to 20 carbon atoms, and the heterocyclic group having 2 to 20 carbon atoms may be substituted with an oxygen atom or a sulfur atom,
$R^{a5}$ represents a hydrogen atom or a methyl group,
$R^{a6}$ represents an alkyl group having 1 to 6 carbon atoms or an alkoxy group having 1 to 6 carbon atoms, and
m represents an integer of 0 to 4, and when m is 2 or more, a plurality of $R^{a6}$ may be the same or different from each other.

5. The resist composition according to claim 3, wherein the resin having a group represented by formula (2) is a novolak resin and a hydroxy group of the novolak resin is substituted with a group represented by formula (2).

6. A method for producing a resist pattern, which comprises:
(1) a step of applying the resist composition according to claim 1 on a substrate,
(2) a step of drying the applied composition to form a composition layer,
(3) a step of exposing the composition layer, and
(4) a step of developing the exposed composition layer.

7. The resist composition according to claim 1, wherein the acid generator is a compound having a group represented by formula (B1):

$$\underset{*}{\overset{*}{\underset{}{\sum}}}N-O-\underset{\underset{O}{\overset{O}{\|}}}{\overset{}{S}}-R^{b1} \quad (B1)$$

wherein, in formula (B1), $R^{b1}$ represents a hydrocarbon group having 1 to 18 carbon atoms which may have a fluorine atom, and a methylene group included in the hydrocarbon group may be substituted with an oxygen atom or a carbonyl group, and
* represents a bond.

8. The resist composition according to claim 7, wherein the acid generator is a compound represented by formula (b1), formula (b2), or formula (b3):

$$(R^{b12'})_2 \underset{}{\overset{O}{\underset{O}{\bigcirc}}} Wb^1 \underset{}{\overset{O}{\underset{O}{\bigcirc}}} N-O-\underset{\underset{O}{\overset{O}{\|}}}{\overset{}{S}}-R^{b1} \quad (b1)$$

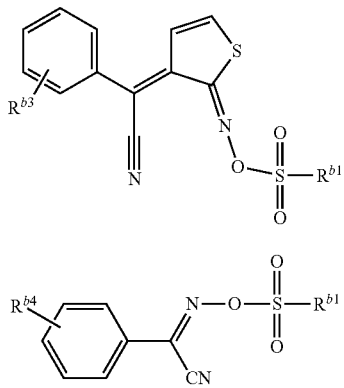
(b2)

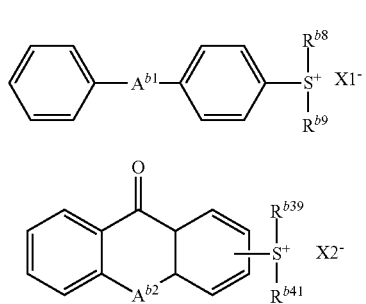
(b3)

wherein, in formula (b1) to formula (b3), $R^{b1}$ is the same as defined in claim 7, $R^{b12'}$, $R^{b3}$, and $R^{b4}$ each independently represent a hydrogen atom, an alkyl group having 1 to 8 carbon atoms, or an alkoxy group having 1 to 8 carbon atoms, ring $Wb^1$ represents an aromatic hydrocarbon ring having 6 to 14 carbon atoms or an aromatic heterocyclic ring having 6 to 14 carbon atoms, and x represents an integer of 0 to 2, and when x is 2, a plurality of $R^{b12'}$ may be the same or different.

9. The resist composition according to claim 1, wherein the acid generator is a compound represented by formula (b8) or formula (b9):

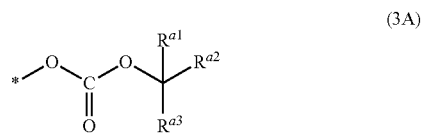
(b8)

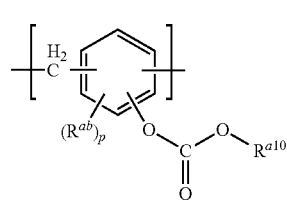
(b9)

wherein, in formula (b8) and formula (b9), $A^{b1}$ and $A^{b2}$ each independently represent an oxygen atom or a sulfur atom, $R^{b8}$, $R^{b9}$, $R^{b10}$ and $R^{b11}$ each independently represent an alkyl group having 1 to 10 carbon atoms or an aromatic hydrocarbon group having 6 to 12 carbon atoms, and $X1^-$ and $X2^-$ represent an organic anion.

10. The resist composition according to claim 1, wherein the quencher is a compound represented by formula (C1) or formula (C2):

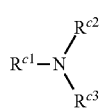
(C1)

wherein, in formula (C1), $R^{c1}$, $R^{c2}$ and $R^{c3}$ each independently represent a hydrogen atom, an alkyl group having 1 to 6 carbon atoms, an alicyclic hydrocarbon group having 5 to 10 carbon atoms, or an aromatic hydrocarbon group having 6 to 10 carbon atoms, a hydrogen atom included in the alkyl group and the alicyclic hydrocarbon group may be substituted with a hydroxy group, an amino group, or an alkoxy group having 1 to 6 carbon atoms, and a hydrogen atom included in the aromatic hydrocarbon group may be substituted with an alkyl group having 1 to 6 carbon atoms, an alkoxy group having 1 to 6 carbon atoms, or an alicyclic hydrocarbon group having 5 to 10 carbon atoms;

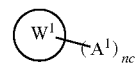
(C2)

wherein, in formula (C2), ring $W^1$ represents a heterocyclic ring having a nitrogen atom as a ring-constituting atom, or a benzene ring having a substituted or unsubstituted amino group, and the heterocyclic ring and the benzene ring may have at least one selected from the group consisting of a hydroxy group and an alkyl group having 1 to 4 carbon atoms, $A^1$ represents a phenyl group or a naphthyl group, and nc represents 2 or 3 and a plurality of $A^1$ may be the same or different.

11. The resist composition according to claim 1, wherein the quencher is a basic nitrogen-containing organic compound.

12. The resist composition according to claim 1, wherein the group represented by formula (3) is a group represented by formula (3A):

(3A)

*—O—C(=O)—O—C($R^{a1}$)($R^{a2}$)($R^{a3}$)

wherein, in formula (3A), $R^{a1}$, $R^{a2}$ and $R^{a3}$ each independently represent an alkyl group having 1 to 8 carbon atoms or an alicyclic hydrocarbon group having 3 to 20 carbon atoms, or $R^{a1}$ and $R^{a2}$ may be bonded to each other to form an alicyclic hydrocarbon group having 3 to 20 carbon atoms together with carbon atoms to which $R^{a1}$ and $R^{a2}$ are bonded, $R^{a3}$ represents an alkyl group having 1 to 8 carbon atoms or an alicyclic hydrocarbon group having 3 to 20 carbon atoms, and * represents a bond.

13. The resist composition according to claim 1, wherein the novolak resin in which a hydroxy group is substituted with a group represented by formula (3) is a resin including a structural unit represented by formula (a3):

(a3)

wherein, in formula (a3),

R$^{10}$ represents a hydrocarbon group having 1 to 20 carbon atoms,

R$^{ab}$ represents a hydroxy group, an alkyl group having 1 to 6 carbon atoms or an alkoxy group having 1 to 6 carbon atoms, and p represents an integer of 0 to 3, and when p is 2 or more, a plurality of R$^{ab}$ may be the same or different from each other.

14. The resist composition according to claim 1, wherein the novolak resin in which a hydroxy group is substituted with a group represented by formula (3) is a resin including a structural unit represented by formula (a3A):

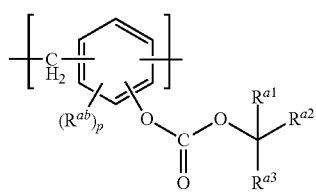

(a3A)

wherein, in formula (a3A),

R$^{a1}$, R$^{a2}$, and R$^{a3}$ each independently represent an alkyl group having 1 to 8 carbon atoms or an alicyclic hydrocarbon group having 3 to 20 carbon atoms, or R$^{a1}$ and R$^{a2}$ and R$^{a2}$ may be bonded to each other to form an alicyclic hydrocarbon group having 3 to 20 carbon atoms together with carbon atoms to which R$^{a1}$ and R$^{a2}$ are bonded, R$^{a3}$ represents an alkyl group having 1 to 8 carbon atoms or an alicyclic hydrocarbon group having 3 to 20 carbon atoms, R$^{ab}$ represents a hydroxy group, an alkyl group having 1 to 6 carbon atoms or an alkoxy group having 1 to 6 carbon atoms, and p represents an integer of 0 to 3, and when p is 2 or more, a plurality of R$^{ab}$ may be the same or different from each other.

15. The resist composition according to claim 1, wherein the alkali-soluble resin is a novolak resin.

\* \* \* \* \*